(12) United States Patent
Dwyer et al.

(10) Patent No.: US 7,702,137 B2
(45) Date of Patent: Apr. 20, 2010

(54) ANATOMICAL VISUALIZATION AND MEASUREMENT SYSTEM

(75) Inventors: Jeff Dwyer, Dublin, NH (US); David Chen, Wrentham, MA (US); M. Weston Chapman, Hanover, NH (US)

(73) Assignee: M2S, Inc., West Lebanon, NH (US)

( * ) Notice: Subject to any disclaimer, the term of this patent is extended or adjusted under 35 U.S.C. 154(b) by 1069 days.

(21) Appl. No.: 11/296,748

(22) Filed: Dec. 7, 2005

(65) Prior Publication Data

US 2007/0014451 A1 Jan. 18, 2007

Related U.S. Application Data

(63) Continuation-in-part of application No. 10/985,199, filed on Nov. 10, 2004, now Pat. No. 7,197,170.

(60) Provisional application No. 60/633,759, filed on Dec. 7, 2004.

(51) Int. Cl.
*G06K 9/00* (2006.01)
(52) U.S. Cl. ....................... 382/128; 382/131
(58) Field of Classification Search ................. 382/128, 382/130–133; 600/117, 407, 587
See application file for complete search history.

(56) References Cited

U.S. PATENT DOCUMENTS

| | | |
|---|---|---|
| 4,722,056 A | 1/1988 | Roberts et al. |
| 4,729,098 A | 3/1988 | Cline et al. |
| 4,882,679 A | 11/1989 | Tuy et al. |
| 4,922,909 A | 5/1990 | Little et al. |
| 4,945,478 A | 7/1990 | Merickel et al. |
| 4,965,844 A | 10/1990 | Oka et al. |
| 4,985,855 A | 1/1991 | Aldrich et al. |
| 4,989,083 A | 1/1991 | Eino |
| 5,005,559 A | 4/1991 | Blanco et al. |
| 5,151,856 A | 9/1992 | Halmann et al. |
| 5,153,721 A | 10/1992 | Eino et al. |
| 5,179,638 A | 1/1993 | Dawson et al. |
| 5,230,623 A | 7/1993 | Guthrie et al. |
| 5,231,483 A | 7/1993 | Sieber et al. |
| 5,255,352 A | 10/1993 | Falk |
| 5,261,404 A | 11/1993 | Mick et al. |
| 5,274,551 A | 12/1993 | Corby, Jr. |

(Continued)

OTHER PUBLICATIONS

Wahle et al. ("Determination of the Absolute Axial Orientation Intracoronary Ultrasound Images in Fusion with Biplane Angiography," IEEE, Published on Sep. 1998, pp. 153-156).*

(Continued)

*Primary Examiner*—Duy M Dang
(74) *Attorney, Agent, or Firm*—Pandiscio & Pandiscio

(57) ABSTRACT

A method for determining the degree of twist to be manually introduced into an implant which is to be positioned in the aorta and adjacent iliac branches so as to achieve an effective degree of twist when the implant is positioned in the anatomy, the method comprising:
  identifying the effective degree of twist desired for the implant;
  determining the Native Iliac Rotation of a patient; and
  subtracting the Native Iliac Rotation of a patient from the effective degree of twist desired for the implant so as to determine the degree of twist to be manually introduced into the implant.

6 Claims, 46 Drawing Sheets

U.S. PATENT DOCUMENTS

| | | | |
|---|---|---|---|
| 5,291,889 A | 3/1994 | Kenet et al. |
| 5,295,199 A | 3/1994 | Shino |
| 5,297,215 A | 3/1994 | Yamagishi |
| 5,316,023 A | 5/1994 | Palmaz et al. |
| 5,319,551 A | 6/1994 | Sekiguchi et al. |
| 5,321,520 A | 6/1994 | Inga et al. |
| 5,329,310 A | 7/1994 | Liljegren et al. |
| 5,361,763 A | 11/1994 | Kao et al. |
| 5,363,476 A | 11/1994 | Kurashige et al. |
| 5,378,915 A | 1/1995 | Hines et al. |
| 5,383,454 A | 1/1995 | Bucholz |
| 5,384,594 A | 1/1995 | Sieber et al. |
| 5,398,684 A | 3/1995 | Hardy |
| 5,417,210 A | 5/1995 | Funda et al. |
| 5,423,315 A | 6/1995 | Margosian et al. |
| 5,447,154 A | 9/1995 | Cinquin et al. |
| 5,448,687 A | 9/1995 | Hoogerhyde et al. |
| 5,461,706 A | 10/1995 | Trow et al. |
| 5,491,510 A | 2/1996 | Gove |
| 5,493,595 A | 2/1996 | Schoolman |
| 5,497,452 A | 3/1996 | Shimizu et al. |
| 5,511,153 A | 4/1996 | Azarbayejani et al. |
| 5,526,812 A | 6/1996 | Dumoulin et al. |
| 5,526,814 A | 6/1996 | Cline et al. |
| 5,531,227 A | 7/1996 | Schneider |
| 5,537,638 A | 7/1996 | Morita et al. |
| 5,558,619 A | 9/1996 | Kami et al. |
| 5,575,817 A | 11/1996 | Martin |
| 5,704,897 A | 1/1998 | Truppe |
| 5,765,561 A | 6/1998 | Chen et al. |
| 5,776,050 A | 7/1998 | Chen et al. |
| 5,825,908 A | 10/1998 | Pieper et al. |
| 5,873,822 A | 2/1999 | Ferre et al. |
| 6,162,246 A | 12/2000 | Barone |
| 6,241,657 B1 | 6/2001 | Chen et al. |
| 6,612,980 B2 | 9/2003 | Chen et al. |
| 6,702,736 B2 | 3/2004 | Chen et al. |
| 7,149,353 B2 | 12/2006 | Siegel et al. |
| 7,194,117 B2 * | 3/2007 | Kaufman et al. ............ 382/128 |
| 2002/0007108 A1 | 1/2002 | Chen et al. |
| 2003/0018235 A1 | 1/2003 | Chen et al. |
| 2003/0028438 A1 | 2/2003 | Smukowski |
| 2004/0133074 A1 | 7/2004 | Chen et al. |
| 2004/0193006 A1 | 9/2004 | Chen et al. |
| 2005/0044541 A1 | 2/2005 | Parthasarathy et al. |
| 2005/0273628 A1 | 12/2005 | Onischuk |

OTHER PUBLICATIONS

Inaoka et al., Knowledge-Based Approach for Recognizing 3-D Pulmonary Structure, Proceedings of the Annual International Conference of the IEEE Engineering in Medicine and Biology Society, Nov. 1988, pp. 1363-1364, vol. 3.

Robb et al., Interactive Display and Analysis of 3-D Medical Images, IEEE Transactions on Medical Imaging, Sep. 1989, pp. 217-226, vol. 8, No. 3.

Peifer et al., Visualization of the Abdominal Aorta Using Three-Dimensional Computer Models Reconstructed from MR Images, Proceedings of the First Conference on Visualization in Biomedical Computing, May 1990, pp. 252-257.

Merchant et al., Semi-Automatic Morphological Measurement of 2-D and 3-D Microvascular Images, Proceedings ICIP-94, IEEE International Conference on Image Processing, Nov. 1994, pp. 416-420, vol. 1.

Kawata et al., Three-Dimensional Imaging of Blood Vessels Using Cone-Beam CT, IEEE Comput. Soc. Press, Proceedings ICIP-94, Nov. 16, 1994, pp. 140-144, vol. 2.

Klein et al., Identifying Vascular Features With Orientation Specific Filters and B-Spline Snakes, IEEE Comput. Soc. Press, Computers in Cardiology, 1994, pp. 113-116.

Chen et al., Left Ventricle Global Motion and Shape from CT Volumetric Data, IEEE, Apr. 1993, pp. V-101 to V-104 (reprint).

Vanroden, Don't Look Now, But a Body Has Been Found in the Basement of the Cummings Hall, Dartmouth Thayer School of Engineering Directions, a periodical published by the Trustees of Dartmouth College, Fall 1993, pp. 30-36, vol. 8, No. 1, Hanover, New Hampshire.

Roberts et al., A Frameless stereotaxic integration of computerized tomographic imaging and the operating microscope, J. Neurosurg., Oct. 1986, pp. 545-549, vol. 65.

Weisburn et al., An interactive graphics editor for 3D surgical simulation, SPIE vol. 626 Medicine XIV/PACS IV, 1986, pp. 483-490.

Shalev et al., Pseudo-3D Imaging with the DICOM-8, SPIE vol. 555 Medical Imaging and Instrumentation '85, 1985, pp. 63-66.

Fowler, Computers May Drive Revolution in Neurosurgery Techniques, Washington Post, Science, Aug. 15, 1994.

Applicants', IRA Magaziner Demo (See TM), displayed Jun. 1993 (24 Minutes).

* cited by examiner

ML1 - Tue, May 30, 1995 10:17 PM

| | | | | |
|---|---|---|---|---|
| ⑧ ← # of vertices | | ⑥ ← # of polygons | | |
| -.5 | .5 | .5 | → X,Y,Z Coordinates of vertex $V_1$ |
| -.5 | -.5 | .5 | → X,Y,Z Coordinates of vertex $V_2$ |
| .5 | -.5 | .5 | → X,Y,Z Coordinates of vertex $V_3$ |
| .5 | .5 | .5 | → X,Y,Z Coordinates of vertex $V_4$ |
| -.5 | .5 | -.5 | → X,Y,Z Coordinates of vertex $V_5$ |
| -.5 | -.5 | -.5 | → X,Y,Z Coordinates of vertex $V_6$ |
| .5 | -.5 | .5 | → X,Y,Z Coordinates of vertex $V_7$ |
| .5 | .5 | -.5 | → X,Y,Z Coordinates of vertex $V_8$ | vertex information face information:

| 4 | 5 | 6 | 7 | 8 |
| 4 | 8 | 7 | 3 | 4 |
| 4 | 2 | 3 | 7 | 6 |
| 4 | 6 | 5 | 1 | 2 |
| 4 | 1 | 5 | 8 | 4 |
| ④ | 3 | 2 | 1 |

↑ # of vertices for a given face

↑ vertices defining a given face

FIG. 8

CUMULATIVE SUM TABLE (LENGTHS)

| INDEX | SUM OF LENGTHS |
|---|---|
| $c_0$ | 0 |
| $c_1$ | 1.5 |
| $c_2$ | 2 |
| $c_3$ | 4 |
| ⋮ | ⋮ |

CUMULATIVE SUM TABLE (VOLUME)

| INDEX | SUM OF VOLUMES |
|---|---|
| $c_0$ | 1.5 |
| $c_1$ | 4 |
| $c_2$ | 5.2 |
| $c_3$ | 6 |
| ⋮ | ⋮ |

Preview 2.0-style Virtual Graft

MSVG after docking of contralateral limb

MSVG before docking of contralateral limb

Yellow Zone represents 'oversizing'

☐ Add Parts to Graft Order                                    ☒

GORE EXCLUDER Device (US) Product Listing

Trunk-Ipslateral Binar Component        Contralateral Leg Component
23x12x16       PCT231216 [0]            12x10.0   PCC121080 [0]
23x12x18       PCT231218 [0]            12x12.0   PCC121280 [0]
23x14.5x16     PCT231416 [0]            12x14.0   PCC121480 [0]
23x14.5x18     PCT231418 [0]            14.5x10.0 PCC141080 [0]
26x12x16       PCT261216 [0]            14.5x12.0 PCC141280 [0]
26x12x18       PCT261218 [0]            14.5x14.0 PCC141480 [0]
26x14.5x16     PCT261416 [0]            16x9.5    PCC161080 [0]
26x14.5x18     PCT261418 [0]            16x11.5   PCC161280 [0]
28.5x12x16     PCT281216 [0]            16x13.5   PCC161480 [0]
28.5x12x18     PCT281218 [0]            18x9.5    PCC181080 [0]
28.5x14.5x16   PCT281416 [0]            18x11.5   PCC181280 [0]
28.5x14.5x18   PCT281418 [0]            18x13.5   PCC181480 [0]
                                        20x9.5    PCC201080 [0]
                                        20x11.5   PCC201280 [0]
                                        20z13.5   PCC201480 [0]

Iliac Extender Component                Aortic Extender Component
10x7.0 PCL 161807  [0]                  23x3.3 PCA238380   [0]
12x7.0 PCL 161207  [0]                  16x3.3 PCA268380   [0]
14.5x7.0 PCL 161407 [0]                 28.5x3.3 PCA288380 [0]

Introducer Sheaths
12x30.0 PG123080 [0]
18x30.0 PG183080 [0]

[ Cancel ]   [ Continue>> ]

Preview 2.1 Product Listing

FIG. 39 resultant Virtual Graft ™

"Twist Lines"

The difference between Preview 2.2 (L) and 2.3 (R) Twisteroo. Both grafts are rotated 0 degrees, in an anatomy with a 53 degree Native Iliac Rotation.

ANATOMICAL VISUALIZATION AND MEASUREMENT SYSTEM

REFERENCE TO PENDING PRIOR PATENT APPLICATIONS

This patent application:

(1) is a continuation-in-part of prior U.S. patent application Ser. No. 10/985,199, filed Nov. 10, 2004, now U.S. Pat. No. 7,197,170, by Jeff Dwyer et al. for ANATOMICAL VISUALIZATION AND MEASUREMENT SYSTEM; and (2) claims benefit of prior U.S. Patent Application Ser. No. 60/633,759, filed Dec. 7, 2004 by Jeff Dwyer et al. for ANATOMICAL VISUALIZATION AND MEASUREMENT SYSTEM.

The two above-identified patent applications are hereby incorporated herein by reference.

FIELD OF THE INVENTION

This invention relates to medical apparatus in general, and more particularly to anatomical visualization and measurement systems.

BACKGROUND OF THE INVENTION

Many medical procedures must be carried out at an interior anatomical site which is normally hidden from the view of the physician. In these situations, the physician typically uses some sort of scanning device to examine the patient's anatomy at the interior site prior to, and in preparation for, conducting the actual medical procedure. Such scanning devices typically include CT scanners, MRI devices, X-ray machines, ultrasound devices and the like, and essentially serve to provide the physician with some sort of visualization of the patient's interior anatomical structure prior to commencing the actual medical procedure. The physician can then use this information to plan the medical procedure in advance, taking into account patient-specific anatomical structure.

In addition to the foregoing, the physician can also use the information obtained from such preliminary scanning to more precisely identify the location of selected structures (e.g., tumors and the like) which may themselves be located within the interior of internal organs or other internal body structures. As a result, the physician can then more easily "zero in" on such selected structures during the subsequent medical procedure.

Furthermore, in many cases, the anatomical structures of interest to the physician may be quite small and/or difficult to identify with the naked eye. In these situations, preliminary scanning of the patient's interior anatomical structure using high resolution scanning devices can help the physician locate various structures of interest during the subsequent medical procedure.

In addition to the foregoing, scanning devices of the sort described above are frequently also used in purely diagnostic procedures. For example, scanning devices of the sort described above might be used to look for stenosis in a blood vessel, or the buildup of plaque in a blood vessel, or a thinning of the aorta wall, etc.

In general, scanning devices of the sort described above tend to generate two-dimensional (i.e., "2-D") images of the patient's anatomical structure. In many cases, the scanning devices are adapted to provide a set of 2-D images, with each 2-D image in the set being related to every other 2-D image in the set according to some pre-determined relationship. For example, CT scanners typically generate a series of 2-D images, with each 2-D image corresponding to a specific plane or "slice" taken through the patient's anatomical structure. Furthermore, with many scanning devices, the angle and spacing between adjacent image planes or slices is very well defined, e.g., each image plane or slice may be set parallel to every other image plane or slice, and adjacent image planes or slices may be spaced a pre-determined distance apart. By way of example, the parallel image planes might be set 1 mm apart.

In a system of the sort just described, the physician can view each 2-D image individually and, by viewing a series of 2-D images in proper sequence, can mentally generate a three-dimensional (i.e., "3-D") impression of the patient's interior anatomical structure.

Some scanning devices include, as part of their basic system, associated computer hardware and software for building a 3-D database of the patient's scanned anatomical structure using a plurality of the aforementioned 2-D images. For example, some CT and MRI scanners include such associated computer hardware and software as part of their basic system. Alternatively, such associated computer hardware and software may be provided independently of the scanning devices, as a sort of "add-on" to the system; in this case, the data from the scanned 2-D images is fed from the scanning device to the associated computer hardware and software in a separate step. In either case, a trained operator using such apparatus can create a set of scanned 2-D images, assemble the data from these scanned 2-D images into a 3-D database of the scanned anatomical structure, and then generate various additional images of the scanned anatomical structure using the 3-D database. This feature has been found to be a very powerful tool, since it essentially permits a physician to view the patient's scanned anatomical structure from a wide variety of different viewing positions. As a result, the physician's understanding of the patient's scanned anatomical structure is generally greatly enhanced.

In addition, scanning systems of the sort described above often include hardware and/or software tools to allow measurements to be made of the patient's scanned anatomical structure. By way of example, many of these systems let a physician overlay lines on an image of the patient's anatomical structure, and then calculate the length of these lines so as to indicate the size of the structure being viewed.

While the 2-D slice images generated by the aforementioned scanning devices, and/or the 3-D database images generated by the aforementioned associated computer hardware and software, are generally of great benefit to physicians, certain significant limitations still exist.

For one thing, with current systems, each scanned 2-D slice image is displayed as a separate and distinct image, and each image generated from the 3-D database is displayed as a separate and distinct image. Unfortunately, physicians can sometimes have difficulty correlating what they see on one image with what they see on another image. By way of example but not limitation, physicians can sometimes have difficulty correlating what they see on a particular scanned 2-D slice image with what they see on a particular image generated from the 3-D database.

For another thing, in many situations a physician may be viewing images of a patient's scanned anatomical structure in preparation for conducting a subsequent medical procedure in which a prosthetic device must be fitted in the patient. In these situations it can be relatively difficult and/or time-consuming for the physician to accurately measure and record all of the anatomical dimensions needed for proper sizing of the prosthetic device to the patient. By way of example, in certain situations a patient may develop an abdominal aortic aneurysm ("AAA") in the vicinity of the aorta's iliac branching, and repair or replacement of the affected vascular structure with a prosthetic device may be indicated. In this case it is extremely important for the physician to determine, prior to commencing the procedure, accurate length and cross-sectional dimensions for each affected portion of blood vessel so as to ensure proper sizing of the appropriate prosthetic device to the patient. Unfortunately, it can be difficult and/or impossible to make accurate anatomical measurements with existing visualization systems. This has proven to be particularly true when dealing with anatomical structures which extend along a tortuous path and/or which have a complex and varied branching structure, e.g., blood vessels.

Furthermore, in many cases it may be desirable to provide a physician with a particular oblique view of a specified portion of a patient's anatomical structure. For example, it may be desirable to provide a physician with a view taken perpendicular to the length of a blood vessel, with that view being taken at a very specific location along that blood vessel. Such a view might be desired for comprehensional and/or measurement purposes. Unfortunately, it can be difficult and/or impossible to accurately generate such a view using existing visualization systems.

In addition to the foregoing, in many situations a physician may be interested in accurately calculating a volume associated with a specific part of a patient's anatomy. By way of example but not limitation, a physician might wish to track the volume of a thrombus in an aorta over time, or the size of a tumor during chemotherapy, etc. Unfortunately, it can be difficult and/or impossible to accurately make such a calculation using existing visualization systems.

Also, in many situations a physician may be interested in modeling how a particular endoluminal prosthesis will deploy in the patient's anatomy. Unfortunately, current visualization systems do not provide simple and effective features for providing such modeling.

OBJECTS OF THE INVENTION

Accordingly, one object of the present invention is to provide an improved anatomical visualization and measurement system for visualizing and measuring anatomical structures.

Another object of the present invention is to provide an improved anatomical visualization and measurement system wherein a scanned 2-D slice image can be appropriately combined with an image generated from a 3-D database so as to create a single composite image.

Another object of the present invention is to provide an improved anatomical visualization and measurement system wherein a marker can be placed onto a 2-D slice image displayed on a screen, and this marker will be automatically incorporated, as appropriate, into a 3-D computer model maintained by the system, as well as into any other 2-D slice image data maintained by the system.

Still another object of the present invention is to provide an improved anatomical visualization and measurement system wherein a margin of pre-determined size can be associated with a marker of the sort described above, and further wherein the margin will be automatically incorporated into the 3-D computer model, and into any other 2-D slice image data, in association with that marker.

Yet another object of the present invention is to provide an improved anatomical visualization and measurement system wherein the periphery of objects contained in a 3-D computer model maintained by the system can be automatically identified in any 2-D slice image data maintained by the system, and further wherein the periphery of such objects can be highlighted as appropriate in 2-D slice images displayed by the system.

Another object of the present invention is to provide an improved anatomical visualization and measurement system wherein patient-specific anatomical dimensions such as length and/or cross-sectional dimensions can be quickly, easily and accurately determined.

Still another object of the present invention is to provide an improved anatomical visualization and measurement system which is particularly well adapted to determine patient-specific anatomical dimensions for structures which have a tortuous and/or branching configuration, e.g., blood vessels.

And another object of the present invention is to provide an improved anatomical visualization and measurement system wherein an appropriate set of scanned 2-D images can be assembled into a 3-D database, information regarding patient-specific anatomical structures can be segmented from the information contained in this 3-D database, and this segmented information can then be used to determine anatomical features such as a centerline for the anatomical structure which has been segmented.

Still another object of the present invention is to provide an improved anatomical visualization and measurement system which is able to easily and accurately present a physician with a particular oblique view of a specified portion of a patient's anatomical structure, e.g., a view taken perpendicular to the length of a blood vessel, with that view being taken at a very specific location along that blood vessel.

Another object of the present invention is to provide an improved anatomical visualization and measurement system wherein patient-specific anatomical volumes can be quickly, easily and accurately determined.

And another object of the present invention is to provide an improved anatomical visualization and measurement system wherein an appropriate set of scanned 2-D images can be assembled into a 3-D database, information regarding patient-specific anatomical structures can be segmented from the information contained in this 3-D database, and this segmented information can then be used to calculate desired patient-specific anatomical volumes.

Another object of the present invention is to provide an improved method for visualizing and measuring anatomical structures.

And another object of the present invention is to provide an improved method wherein patient-specific anatomical dimensions such as length and/or cross-sectional dimensions can be quickly, easily and accurately determined.

Still another object of the present invention is to provide an improved method wherein an appropriate set of scanned 2-D images can be assembled into a 3-D database, information regarding patient-specific anatomical structures can be segmented from the information contained in this 3-D database, and this segmented information can then be used to determine anatomical features such as a centerline for the anatomical structure which has been segmented.

And another object of the present invention is to provide a method for easily and accurately presenting a physician with a particular oblique view of a specified portion of a patient's anatomical structure, e.g., a view taken perpendicular to the length of a blood vessel, with that view being taken at a very specific location along that blood vessel.

Yet another object of the present invention is to provide an improved method for quickly, easily and accurately determining patient-specific anatomical volumes.

And another object of the present invention is to provide an improved system for modeling how a particular endoluminal prosthesis will deploy in the patient's anatomy.

SUMMARY OF THE INVENTION

These and other objects are addressed by the present invention, which comprises an anatomical visualization and measurement system comprising a first database which comprises a plurality of 2-D slice images generated by scanning an anatomical structure. These 2-D slice images are stored in a first data format. A second database is also provided which comprises a 3-D computer model of the scanned anatomical structure. This 3-D computer model comprises a first software object which is representative of the scanned anatomical structure and which is defined by a 3-D geometry database.

In one embodiment of the present invention, means are provided for selecting a particular 2-D slice image from the first database. Means are also provided for inserting a second software object into the 3-D computer model so as to augment the 3-D computer model. The second software object is also defined by a 3-D geometry database, and includes a planar surface. In this embodiment of the invention, the second software object is inserted into the 3-D computer model at the position which corresponds to the position of the selected 2-D slice image relative to the scanned anatomical structure. Means for texture mapping the specific 2-D slice image onto the planar surface of the second software object are also provided. Means are also provided for displaying an image of the augmented 3-D computer model so as to simultaneously provide a view of both the first software object and the specific 2-D slice image which has been texture mapped onto the planar surface of the second software object.

In another embodiment of the invention, the system comprises a first database which comprises a plurality of 2-D slice images generated by scanning an anatomical structure. These 2-D slice images are stored in a first data format. A second database is also provided which comprises a 3-D computer model of the scanned anatomical structure. This 3-D computer model comprises a first software object which is representative of the scanned anatomical structure and which is defined by a 3-D geometry database. In this second embodiment of the invention, means are also provided for inserting a second software object into the 3-D computer model so as to augment the 3-D computer model. The second software object is also defined by a 3-D geometry database, and includes a planar surface. Furthermore, means are also provided for determining the specific 2-D slice image which corresponds to the position of the planar surface of the second software object which has been inserted into the augmented 3-D computer model. In this embodiment of the invention, means are also provided for texture mapping the specific 2-D slice image corresponding to the position of that planar surface onto the planar surface of the second software object. In this embodiment of the invention, display means are also provided for displaying an image of the augmented 3-D computer model to a physician so as to simultaneously provide a view of the first software object and the specific 2-D slice image which has been texture mapped onto the planar surface of the second software object.

In each of the foregoing embodiments of the present invention, the 3-D geometry database may comprise a surface model.

Likewise, the system may further comprise means for inserting a marker into the first database, whereby the marker will be automatically incorporated into the second database, and further wherein the marker will be automatically displayed where appropriate in any image displayed by the system.

Also, the system may further comprise a margin of predetermined size associated with the aforementioned marker.

Additionally, the system may further comprise means for automatically identifying the periphery of any objects contained in the second database and for identifying the corresponding data points in the first database, whereby the periphery of such objects can be highlighted as appropriate in any image displayed by the system.

Often, the scanned structure will comprise an interior anatomical structure.

In yet another form of the present invention, the visualization and measurement system may incorporate means for determining patient-specific anatomical dimensions, such as length and/or cross-sectional dimensions, using appropriate scanned 2-D image data. More particularly, the visualization and measurement system may include means for assembling an appropriate set of scanned 2-D images into a 3-D database, means for segmenting information regarding patient-specific anatomical structures from the information contained in the 3-D database, means for determining from this segmented information anatomical features such as a centerline for the anatomical structure which has been segmented, means for specifying a measurement to be made based on the determined anatomical feature, and means for calculating the measurements so specified.

In a more particular form of the present invention, the visualization and measurement system is particularly well adapted to determine patient-specific anatomical dimensions for structures which have a tortuous and/or branching configuration, e.g., blood vessels. In this form of the invention, the visualization and measurement system is adapted to facilitate (1) assembling an appropriate set of scanned 2-D images into a 3-D database; (2) segmenting the volumetric data contained in the 3-D database into a set of 3-D locations corresponding to the specific anatomical structure to be measured; (3) specifying, for each branching structure contained within the specific anatomical structure of interest, a branch line in the volumetric data set that uniquely indicates that branch structure, with the branch line being specified by selecting appropriate start and end locations on two of the set of scanned 2-D images; (4) calculating, for each branching structure contained within the specific anatomical structure of interest, a centroid path in the volumetric data set for that branching structure, with the centroid path being determined by calculating, for each scanned 2-D image corresponding to the branch line, the centroid for the branch structure contained in that particular scanned 2-D image; (5) applying a curve-fitting algorithm to the centroid paths determined above so as to supply data for any portions of the anatomical structure which may lie between the aforementioned branch lines, and for "smoothing out" any noise that may occur in the system; and (6) applying known techniques to the resulting space curves so as to determine the desired anatomical dimensions.

In still another form of the present invention, the visualization and measurement system may incorporate means for easily and accurately presenting a physician with a particular oblique view of a specified portion of a patient's anatomical structure, e.g., a view taken perpendicular to a blood vessel, at a very specific location along that blood vessel.

In another form of the present invention, the visualization and measurement system may incorporate means for more accurately measuring the dimensions of an anatomical structure by utilizing one or more oblique views taken along the length of that anatomical structure.

In yet another form of the present invention, the visualization and measurement system may incorporate means for determining patient-specific anatomical volumes using appropriate scanned 2-D image data. More particularly, the visualization and measurement system may include means for assembling an appropriate set of scanned 2-D images into a 3-D database, means for segmenting information regarding patient-specific anatomical structures from the information contained in the 3-D database, means for determining from this segmented information anatomical volumes from the anatomical structure which has been segmented, means for specifying a structure of interest, and means for calculating the volume of the specified structure.

The present invention also comprises an improved method for visualizing and measuring anatomical structures.

The present invention also comprises a method for calculating patient-specific anatomical dimensions using appropriate scanned 2-D image data. In one form of the present invention, the method comprises the steps of (1) assembling an appropriate set of scanned 2-D images into a 3-D database; (2) segmenting information regarding patient-specific anatomical structures from the information contained in the 3-D database, (3) determining for this segmented information anatomical features such as a centerline for the anatomical structure which has been segmented; (4) specifying a measurement to be made based on the determined anatomical feature; and (5) calculating the measurement so specified.

The present invention also comprises a method for easily and accurately presenting a physician with a particular oblique view of a specified portion of a patient's anatomical structure, e.g., a view taken perpendicular to a blood vessel, at a very specific location along that blood vessel.

The present invention also comprises a method for calculating patient-specific anatomical volumes using appropriate scanned 2-D image data. In one form of the present invention, the method comprises the steps of (1) assembling an appropriate set of scanned 2-D images into a 3-D database; (2) segmenting information regarding patient-specific anatomical structures from the information contained in the 3-D database, (3) determining from this segmented information volumes for the anatomical structure which has been segmented, (4) specifying a structure of interest, and (5) calculating the volume of the specified structure.

In another form of the invention, there is provided a computer-based visualization system for visualizing anatomical structure and a graft implant which is to be deployed adjacent the anatomical structure, comprising:

a 3-D computer model of the anatomical structure which is to be visualized, said 3-D computer model comprising at least one first software object, wherein said at least one first software object corresponds to the anatomical structure which is to be visualized;

a database of second software objects, wherein at least one of said second software objects corresponds to a graft implant which is to be deployed adjacent the anatomical structure;

selection apparatus for permitting a user to select said at least one of said second software objects;

registration apparatus for positioning said selected at least one of said second software objects into said 3-D computer model so as to create an augmented 3-D computer model, with said selected at least one of said second software objects being positioned in said augmented 3-D computer model in proper registration with said at least one first software object contained in said augmented 3-D model; and processing apparatus for generating an image of said augmented 3-D computer model so as to simultaneously provide a view of said at least one first software object and said selected at least one second software object.

In another form of the invention, there is provided a method for visualizing anatomical structure and a graft implant which is to be deployed adjacent the anatomical structure, comprising:

providing a 3-D computer model of the anatomical structure which is to be visualized, said 3-D computer model comprising at least one first software object, wherein said at least one first software object corresponds to the anatomical structure which is to be visualized;

providing a database of second software objects, wherein at least one of said second software objects corresponds to a graft implant which is to be deployed adjacent the anatomical structure;

selecting said at least one of said second software objects;

positioning said selected at least one of said second software objects into said 3-D computer model so as to create an augmented 3-D computer model, with said selected at least one of said second software objects being positioned in said augmented 3-D computer model in proper registration with said at least one first software object contained in said augmented 3-D model; and generating an image of said augmented 3-D computer model so as to simultaneously provide a view of said at least one first software object and said selected at least one second software object.

In another form of the invention, there is provided a visualization system comprising:

a first database comprising a plurality of 2-D slice images generated by scanning an anatomical structure, said 2-D slice images being stored in a first data format;

a second database comprising a 3-D computer model of said scanned anatomical structure, said 3-D computer model comprising at least one first software object, said at least one first software object being defined by a 3-D geometry database;

insertion apparatus for selectively inserting a second software object into said 3-D computer model so as to augment said 3-D computer model, said second software object being defined by a 3-D geometry database and including a planar surface;

determining apparatus for determining the specific 2-D slice image associated with the position of said planar surface of said second software object when said second software object is inserted within said augmented 3-D computer model;

texture mapping apparatus for texture mapping said specific 2-D slice image onto said planar surface of said second software object when said second software object is inserted within said augmented 3-D computer model;

a third database of third software objects, wherein at least one of said third software objects corresponds to a graft implant which is to be deployed adjacent the scanned anatomical structure;

selection apparatus for permitting a user to select said at least one of said third software objects;

registration apparatus for selectively positioning said selected at least one of said third software objects into said augmented 3-D computer model, with said selected at least one of said third software objects being positioned in said augmented 3-D computer model in proper registration with said at least one first software object contained in said augmented 3-D model; and display apparatus for displaying an image of said augmented 3-D computer model so as to simultaneously provide a view of said (i) first software object; (ii) said specific 2-D slice image texture mapped onto said planar surface of said second software object when said second software object is inserted within said augmented 3-D computer model; and (iii) said at least one of said third software objects when said at least on one of said third software objects is positioned within said augmented 3-D computer model.

In another form of the invention, there is provided a method for visualizing structure, comprising:

providing a first database comprising a plurality of 2-D slice images generated by scanning an anatomical structure, said 2-D slice images being stored in a first data format;

providing a second database comprising a 3-D computer model of said scanned anatomical structure, said 3-D computer model comprising at least one first software object, said at least one first software object being defined by a 3-D geometry database;

providing insertion apparatus for selectively inserting a second software object into said 3-D computer model so as to augment said 3-D computer model, said second software object being defined by a 3-D geometry database and including a planar surface;

providing determining apparatus for determining the specific 2-D slice image associated with the position of said planar surface of said second software object when said second software object is inserted within said augmented 3-D computer model;

providing texture mapping apparatus for texture mapping said specific 2-D slice image onto said planar surface of said second software object when said second software object is inserted within said augmented 3-D computer model;

providing a third database of third software objects, wherein at least one of said third software objects corresponds to a graft implant which is to be deployed adjacent the scanned anatomical structure;

selecting said at least one of said third software objects;

positioning said selected at least one of said third software objects into said augmented 3-D computer model, with said selected at least one of said third software objects being positioned in said augmented 3-D computer model in proper registration with said at least one first software object contained in said augmented 3-D model; and displaying an image of said augmented 3-D computer model so as to simultaneously provide a view of (i) said first software object; (ii) said at least one of said third software objects; and (iii) said specific 2-D slice image texture mapped onto said planar surface of said second software object when said second software object is inserted within said augmented 3-D computer model.

In another preferred form of the invention, there is provided a method for determining the degree of twist to be manually introduced into an implant which is to be positioned in the aorta and adjacent iliac branches so as to achieve an effective degree of twist when the implant is positioned in the anatomy, the method comprising:

identifying the effective degree of twist desired for the implant;

determining the Native Iliac Rotation of a patient; and subtracting the Native Iliac Rotation of a patient from the effective degree of twist desired for the implant so as to determine the degree of twist to be manually introduced into the implant.

In another preferred form of the invention, there is provided a method for determining the degree and location of twist to be manually introduced into an implant which is to be positioned in the aorta and adjacent iliac branches so as to achieve an effective degree of twist when the implant is positioned in the anatomy, the method comprising:

identifying the effective degree of twist desired for the implant;

determining the Native Iliac Rotation of a patient;

subtracting the Native Iliac Rotation of a patient from the effective degree of twist desired for the implant so as to determine the degree of twist to be manually introduced into the implant;

identifying at least one control point intermediate the two ends of the implant, and dividing the total length of the implant equally across the number of control points so as to yield a plurality of equal length graft segments; and distributing the degree of twist to be manually introduced into the implant equally across each of the graft segments.

In another preferred form of the invention, there is provided a method for determining the Native Iliac Rotation of a patient, the method comprising:

determining a left iliac centerline;

determining a right iliac centerline;

choosing a left iliac point on the left iliac centerline;

choosing a right iliac point on the right iliac centerline; and determining the line extending between the left iliac point and the right iliac point and expressing the Native Iliac Rotation as a function of the line position relative to the coronal plane of the patient.

In another preferred form of the invention, there is provided an apparatus for determining the degree of twist to be manually introduced into an implant which is to be positioned in the aorta and adjacent iliac branches so as to achieve an effective degree of twist when the implant is positioned in the anatomy, the apparatus comprising:

apparatus for specifying the effective degree of twist desired for the implant;

apparatus for determining the Native Iliac Rotation of a patient; and apparatus for subtracting the Native Iliac Rotation of a patient from the effective degree of twist desired for the implant so as to determine the degree of twist to be manually introduced into the implant.

In another preferred form of the invention, there is provided an apparatus for determining the degree and location of twist to be manually introduced into an implant which is to be positioned in the aorta and adjacent iliac branches so as to achieve an effective degree of twist when the implant is positioned in the anatomy, the apparatus comprising:

apparatus for specifying the effective degree of twist desired for the implant;

apparatus for determining the Native Iliac Rotation of a patient;

apparatus for subtracting the Native Iliac Rotation of a patient from the effective degree of twist desired for the implant so as to determine the degree of twist to be manually introduced into the implant;

apparatus for specifying at least one control point intermediate the two ends of the implant, and dividing the total length of the implant equally across the number of control points so as to yield a plurality of equal length graft segments; and apparatus for specifying the degree of twist to be manually introduced into the implant equally across each of the graft segments.

In another preferred form of the invention, there is provided an apparatus for determining the Native Iliac Rotation of a patient, the apparatus comprising:

apparatus for determining a left iliac centerline;

apparatus for determining a right iliac centerline;

apparatus for choosing a left iliac point on the left iliac centerline;

apparatus for choosing a right iliac point on the right iliac centerline; and apparatus for determining the line extending between the left iliac point and the right iliac point and expressing the Native Iliac Rotation as a function of the line position relative to the coronal plane of the patient.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 8 illustrates the data file format of the polygonal surface model for the simple unit cube shown in FIG. 7;

FIG. 39 is a schematic representation of a Manufacturer Specific Virtual Graft (MSVG) Product Listing;

DETAILED DESCRIPTION OF THE PREFERRED EMBODIMENT

Basic System

Figure 1:
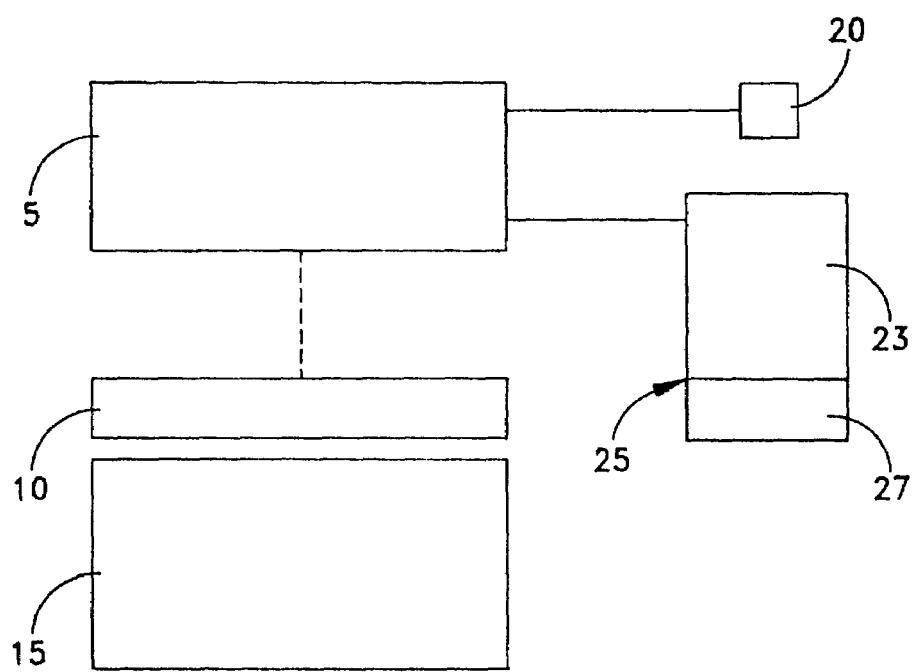
FIG. 1 is a schematic view showing a scanning device for generating a set of 2-D images of the anatomy of a patient.

Looking first at FIG. 1, a scanning device 5 is shown as it scans the interior anatomical structure of a patient 10, as that patient 10 lies on a scanning platform 15.

Scanning device 5 is of the sort adapted to generate scanning data corresponding to a series of 2-D images, where each 2-D image corresponds to a specific viewing plane or "slice" taken through the patient's body. Furthermore, scanning device 5 is adapted so that the angle and spacing between adjacent image planes or slices can be very well defined, e.g., each image plane or slice may be set parallel to every other image plane or slice, and adjacent image planes or slices may be spaced a pre-determined distance apart. By way of example, the parallel image planes might be set 1 mm apart.

The scanning data obtained by scanning device 5 can be displayed as a 2-D slice image on a display 20, and/or it can be stored in its 2-D slice image data form in a first section 23 of a data storage device or medium 25. Furthermore, additional information associated with the scanning data (e.g., patient name, age, etc.) can be stored in a second section 27 of data storage device or medium 25.

By way of example, scanning device 5 might comprise a CT scanner of the sort manufactured by GE Medical Systems of Milwaukee, Wis.

Figure 2:
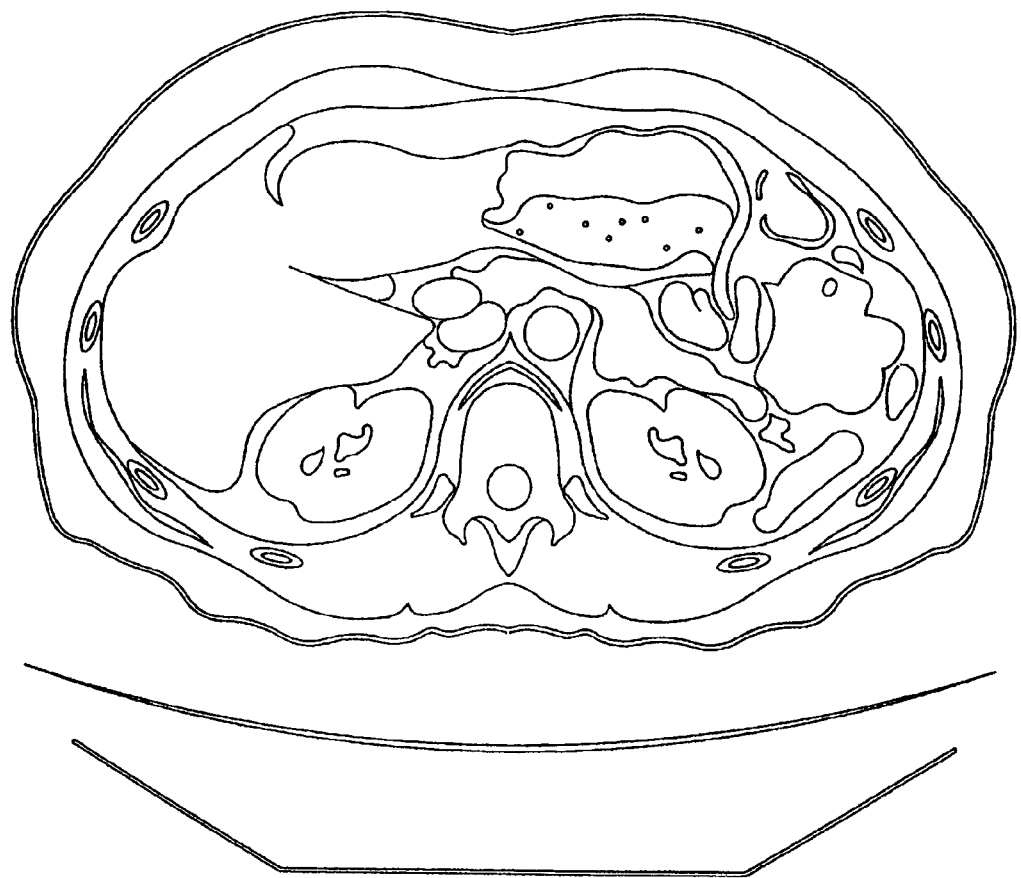
FIG. 2 is a 2-D slice image corresponding to an axial slice taken through the abdomen of an individual.

By way of further example, a 2-D slice image of the sort generated by scanning device 5 and displayed on display 20 might comprise the 2-D slice image shown in FIG. 2. In the particular example shown in FIG. 2, the 2-D slice image shown corresponds to an axial slice taken through an individual's abdomen and showing, among other things, that individual's liver.

Scanning device 5 may format its scanning data in any one of a number of different data structures. By way of example, scanning device 5 might format its scanning data in the particular data format used by a CT scanner of the sort manufactured by GE Medical Systems of Milwaukee, Wis. More specifically, with such a scanning device, the scanning data is generally held as a series of data "frames", where each data frame corresponds to a particular 2-D slice image taken through the patient's body. Furthermore, within each data frame, the scanning data is generally organized so as to represent the scanned anatomical structure at a particular location within that 2-D slice image. Such a data structure is fairly common for scanning devices of the sort associated with the present invention. However, it should be appreciated that the present invention is not dependent on the particular data format utilized by scanning device 5. For the purposes of the present invention, the scanning data provided by scanning device 5 can be formatted in almost any desired data structure, so long as that data structure is well defined, whereby the scanning data can be retrieved and utilized as will hereinafter be disclosed in further detail.

Figure 3:
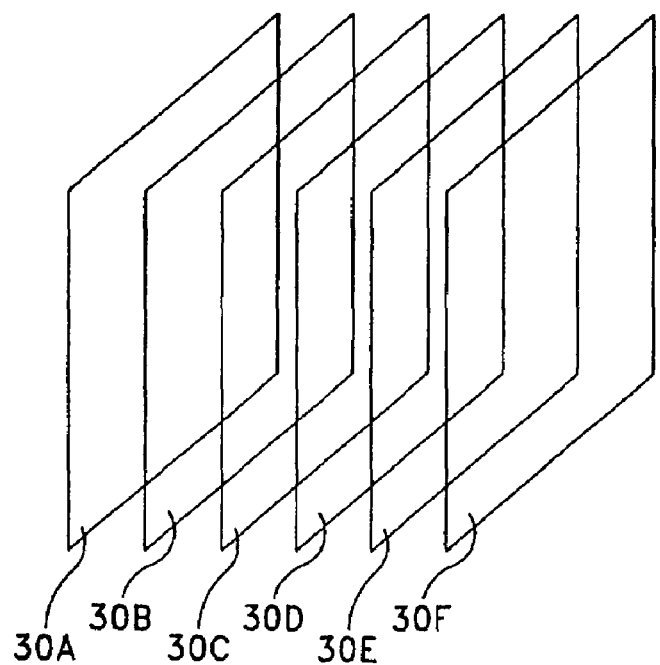
FIG. 3 shows a series of data frames corresponding to 2-D slice images arranged in a parallel array.
Figure 4:
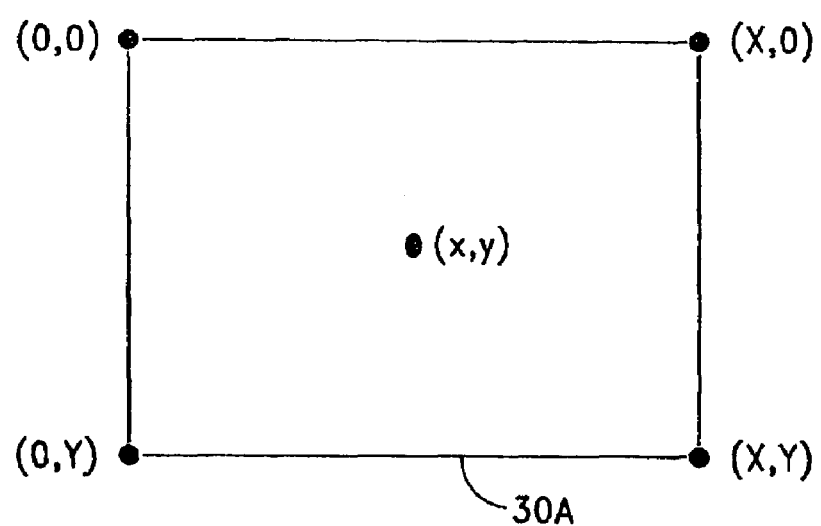
FIG. 4 is a schematic view showing the scanning data contained within an exemplary data frame.

For purposes of illustrating the present invention, it can be convenient to think of the scanning data generated by scanning device 5 as being organized in the data structures schematically illustrated in FIGS. 3 and 4.

More particularly, in FIG. 3, a series of data frames 30A, 30B, 30C, etc. are shown arranged in a parallel array. Each of these data frames 30A, 30B, 30C, etc. corresponds to a particular 2-D slice image taken through the patient's body by scanning device 5, where the 2-D slice images are taken parallel to one another. In addition, adjacent image planes or slices are spaced apart by a constant, pre-determined distance, e.g., 1 mm. It will be appreciated that data frames 30A, 30B, 30C, etc. collectively form a volumetric data set which is representative of the patient's scanned anatomical structure.

Furthermore, in FIG. 4, the scanning data contained within an exemplary data frame 30A is shown represented in an X-Y coordinate scheme so as to quickly and easily identify the scanned anatomical structure disposed at a particular location within that 2-D slice image. Typically, the scanning data relating to a particular X-Y coordinate represents an image intensity value. This image intensity value generally reflects some attribute of the specific anatomical structure being scanned, e.g., the tissue density.

As noted above, the scanning data generated by scanning device 5 is stored in its 2-D slice image data form in first section 23 of data storage device or medium 25, with the scanning data being stored in a particular data format as determined by the manufacturer of scanning device 5.

Figure 5:
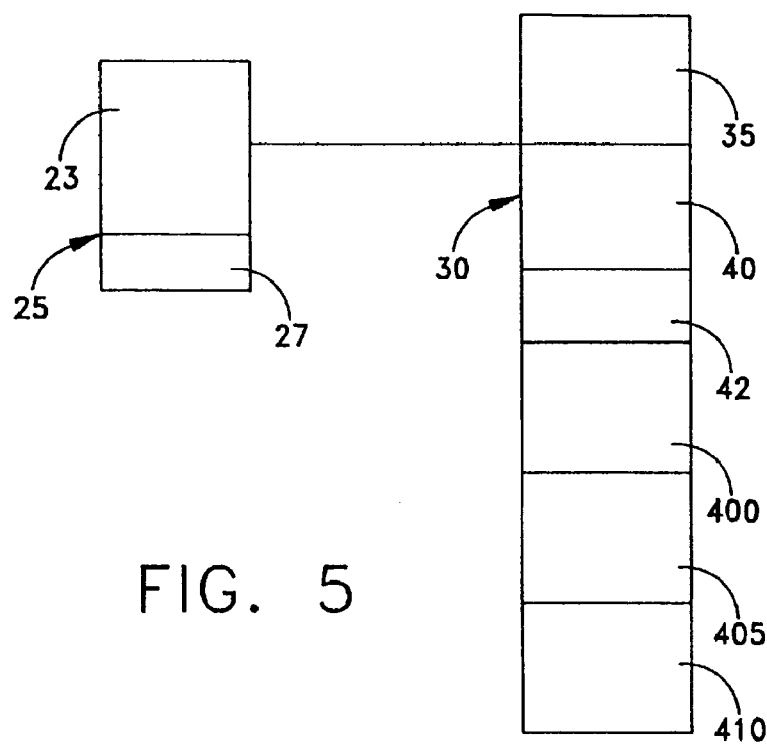
FIG. 5 shows scanning data stored in a first storage device or medium being retrieved, processed and then stored again in a second data storage device or medium.

In accordance with the present invention, and looking now at FIG. 5, the scanning data stored in first section 23 of data storage device or medium 25 is retrieved, processed and then stored again in a data storage device or medium 30.

More particularly, the scanning data stored in first section 23 of data storage device or medium 25 is retrieved and processed so as to convert the scanning data generated by scanning device 5 from its 2-D slice image data form into a 3-D computer model of the patient's anatomical structure. This 3-D computer model is then stored in a first section 35 of data storage device or medium 30.

In addition, the scanning data stored in first section 23 of data storage device or medium 25 is retrieved and processed as necessary so as to convert the scanning data into a preferred data format for the 2-D slice image data. The 2-D slice image data is then stored in this preferred data format in second section 40 of data storage device or medium 30.

Furthermore, the additional information associated with the scanning data (e.g., patient name, age, etc.) which was previously stored in second section 27 of data storage device or medium 25 can be stored in a third section 42 of data storage device or medium 30.

In accordance with the present invention, once the 3-D computer model has been stored in first section 35 of data storage device or medium 30, and the 2-D slice image data has been stored in a preferred data format in second section 40 of data storage device or medium 30, a physician can then use an appropriately programmed computer to access the 3-D computer model stored in first section 35 of data storage device or medium 30, and/or the 2-D slice image data stored in second section 40 of data storage device or medium 30, to generate desired patient-specific images.

Figure 6:
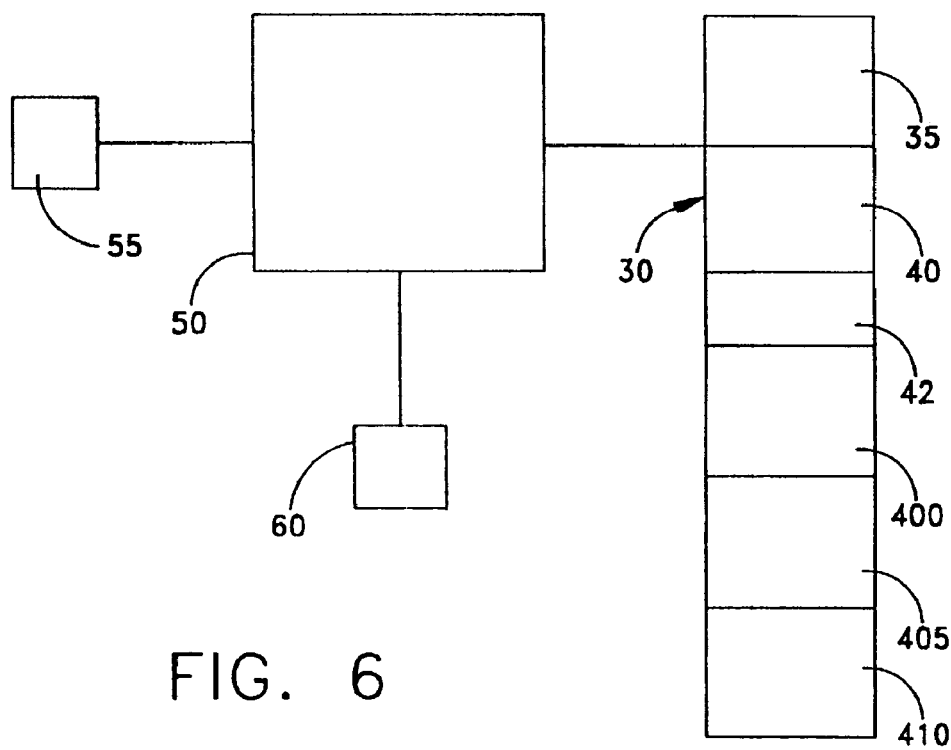
FIG. 6 is a schematic view of a system for retrieving and viewing scanning data.

More particularly, and looking now at FIG. 6, once the 3-D computer model has been stored in first section 35 of data storage device or medium 30, and the 2-D slice image data has been stored in a preferred data format in second section 40 of data storage device or medium 30, a physician can use an appropriately programmed computer 50, operated by input devices 55, to access the 3-D computer model stored in first section 35 of data storage device or medium 30, and/or the 2-D slice image data stored in second section 40 of data storage device or medium 30, so as to generate the desired patient-specific images and display those images on a display 60.

To this end, it will be appreciated that the specific data structure used to store the 3-D computer model in first section 35 of data storage device or medium 30, and the specific data structure used to store the 2-D slice image data in second section 40 of data storage device or medium 30, will depend on the specific nature of computer 50 and on the particular operating system and application software being run on computer 50.

Figure 7:
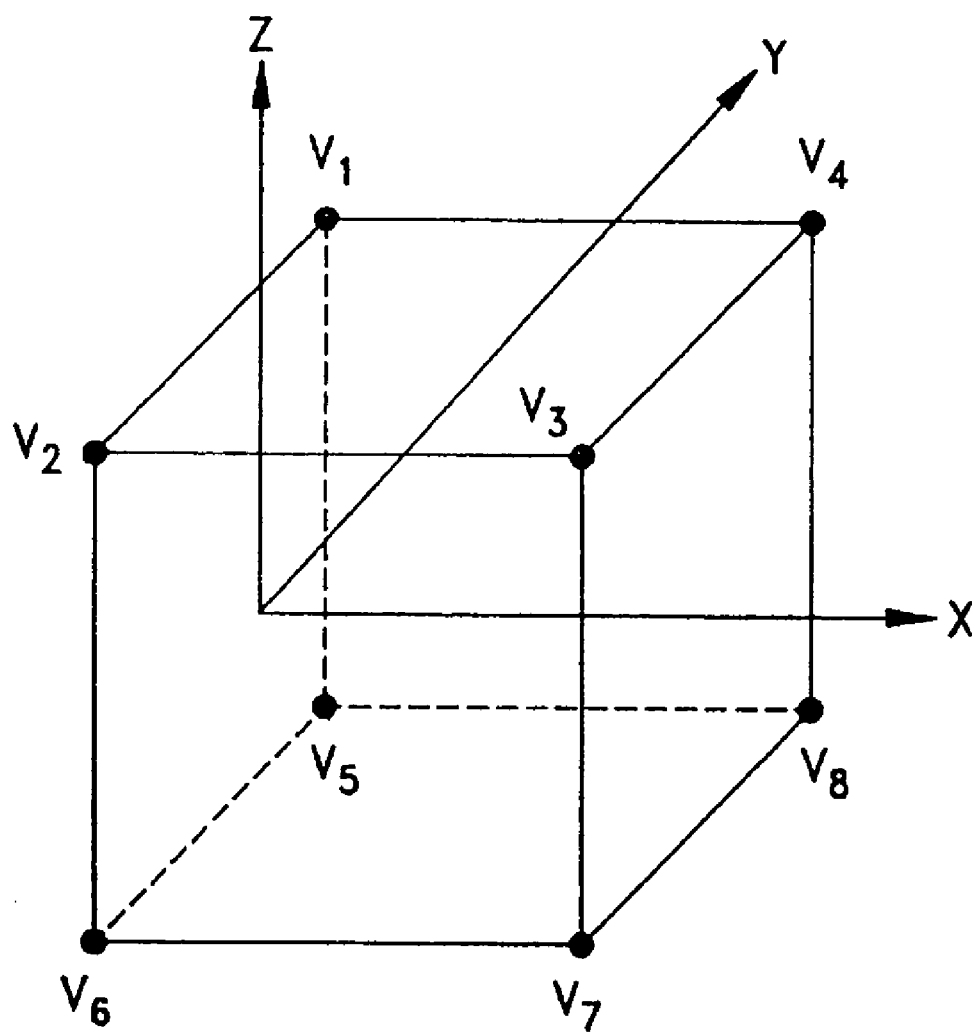
FIG. 7 is a schematic view of a unit cube for use in defining polygonal surface models.
Figure 9A:
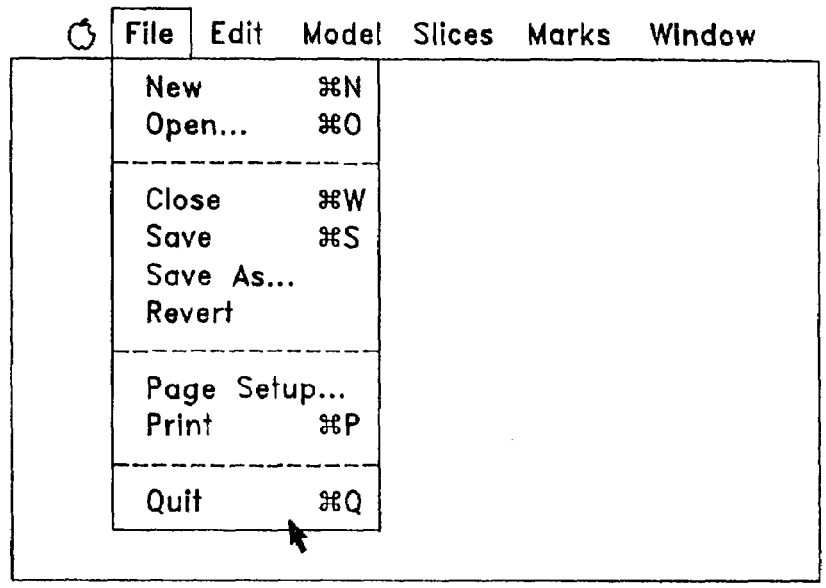
FIGS. 9A-9F illustrate a variety of menu choices which may be utilized in connection with the present invention.
Figure 9B:
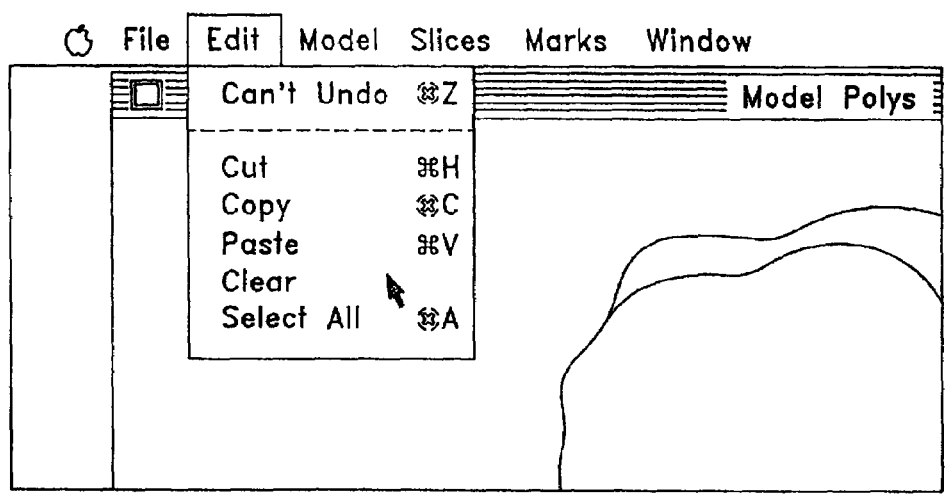
Figure 9C:
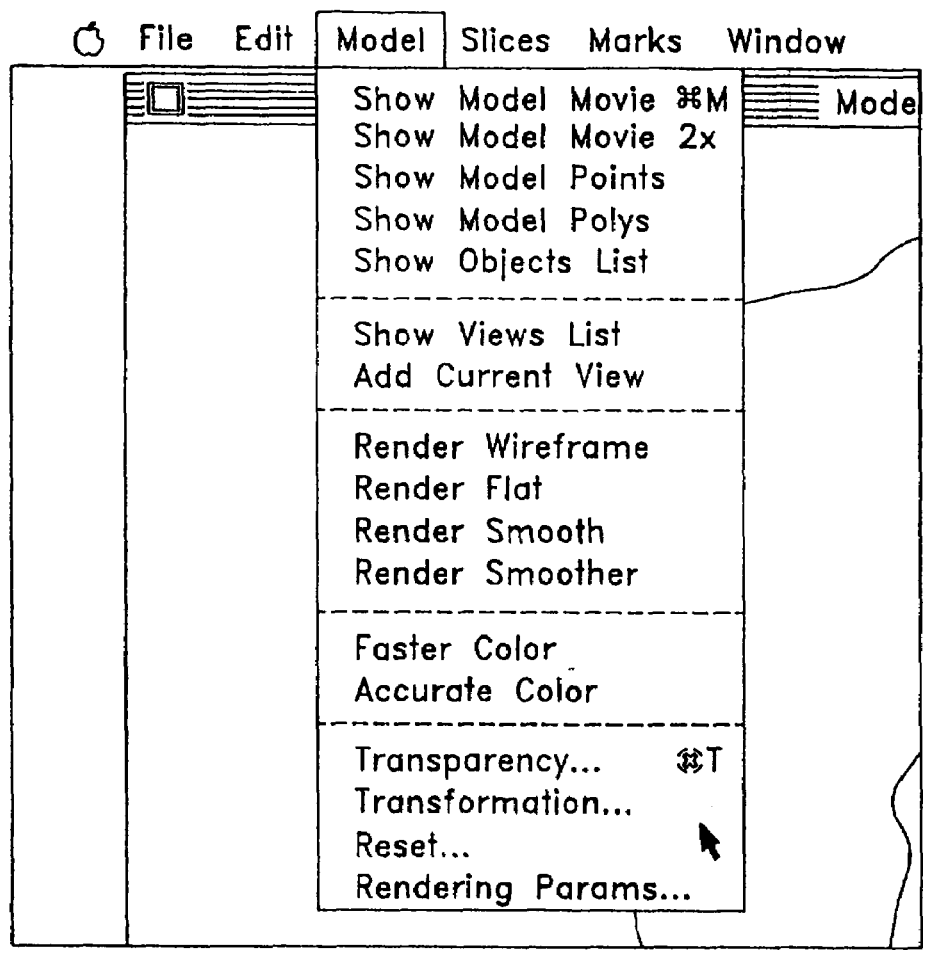
Figure 9D:
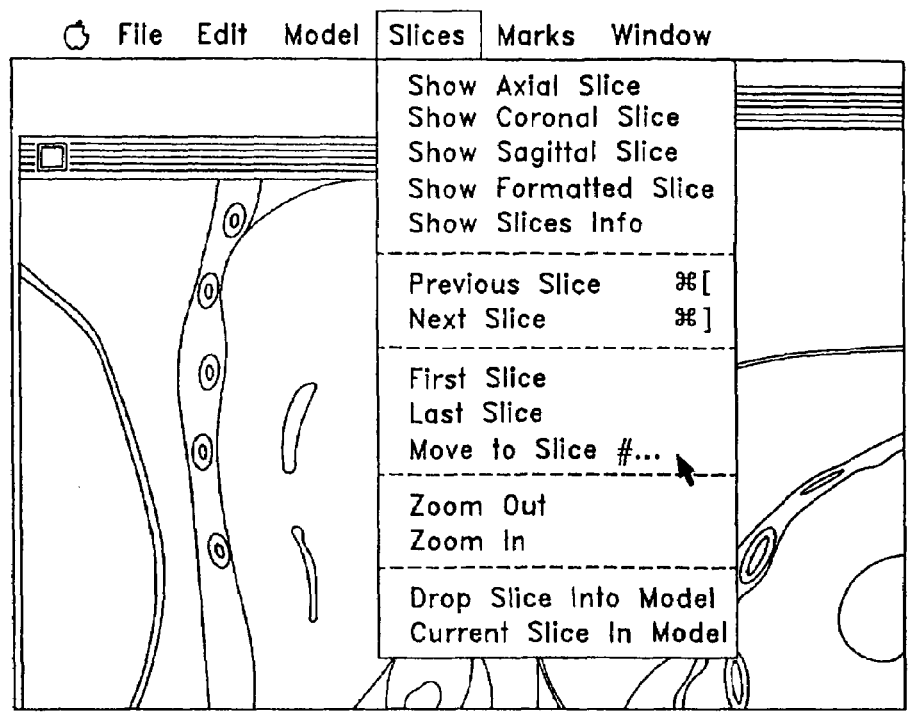
Figure 9E:
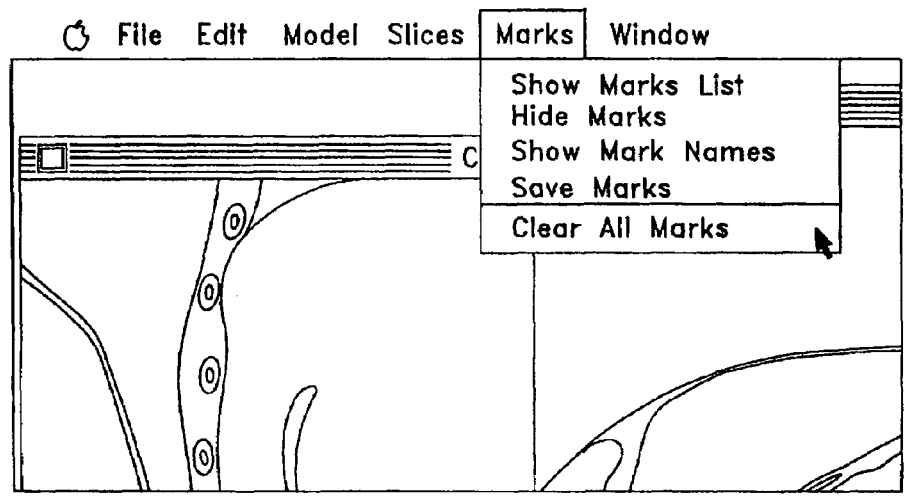
Figure 9F:
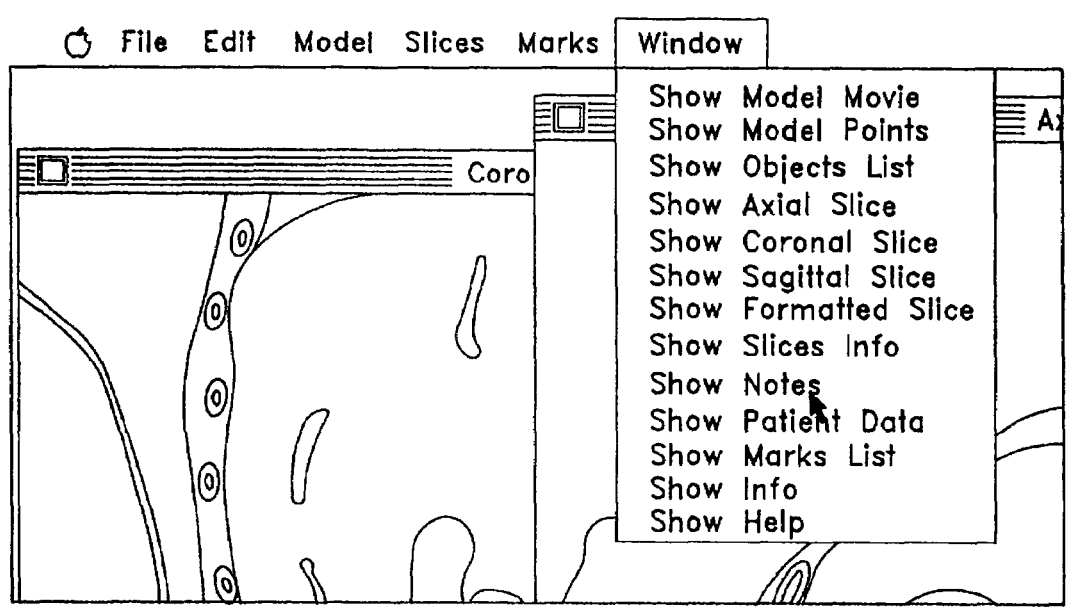

In general, however, the 3-D computer model contained in first section 35 of data storage device or medium 30 is preferably structured as a collection of software objects, with each software object being defined by a polygonal surface model of the sort well known in the art. By way of example, a scanned anatomical structure such as a human liver might be modeled as three distinct software objects, with the outer surface of the general mass of the liver being one software object, the outer surface of the vascular structure of the liver being a second software object, and the outer surface of a tumor located in the liver being a third software object. By way of further example, FIGS. 7 and 8 illustrate a typical manner of defining a software object by a polygonal surface model. In particular, FIG. 7 illustrates the vertices of a unit cube set in an X-Y-Z coordinate system, and FIG. 8 illustrates the data file format of the polygonal surface model for this simple unit cube. As is well known in the art, more complex shapes such as human anatomical structure can be expressed in corresponding terms.

Furthermore, the 3-D computer model contained in first section 35 of data storage device or medium 30 is created by analyzing the 2-D slice image data stored in first section 23 of data storage device or medium 25 using techniques well known in the art. For example, the 2-D slice image data stored in first section 23 of data storage device or medium 25 might be processed using the well known "Marching Cubes" algorithm, which is a so-called "brute force" surface construction algorithm that extracts isodensity surfaces from a volumetric data set, producing from one to five triangles within voxels that contain the surface. Alternatively, the 2-D slice image data stored in first section 23 of data storage device or medium 25 might be processed into the 3-D computer model stored in first section 35 of data storage device or medium 30 by some other appropriate modeling algorithm so as to yield the desired 3-D computer model which is stored in first section 35 of data storage device or medium 30.

As noted above, the specific data structure used to store the 2-D slice image data in second section 40 of data storage device or medium 30 will also depend on the specific nature of computer 50 and on the particular operating system and application software being run on computer 50.

In general, however, the 2-D slice image data contained in second section 40 of data storage device or medium 30 is preferably structured as a series of data "frames", where each data frame corresponds to a particular 2-D slice image taken through the patient's body, and where the scanning data within each data frame is organized so as to represent the scanned anatomical structure at a particular location within that 2-D slice image.

In the present invention, it is preferred that computer 50 comprise a Power PC-based, Macintosh operating system ("Mac OS") type of computer, e.g. a Power PC Macintosh 8100/80 of the sort manufactured by Apple Computer, Inc. of Cupertino, Calif. In addition, it is preferred that computer 50 be running Macintosh operating system software, e.g. Mac OS Ver. 7.5.1, such that computer 50 can readily access a 3-D computer model formatted in Apple's well-known Quick-Draw 3D data format and display images generated from that 3D computer model, and such that computer 50 can readily access and display 2-D images formatted in Apple's well-known QuickTime image data format. Input devices 55 preferably comprise the usual computer input devices associated with a Power PC-based, Macintosh operating system computer, e.g., input devices 55 preferably comprise a keyboard, a mouse, etc.

In view of the foregoing, in the present invention it is also preferred that the 3-D computer model contained in first section 35 of data storage device or medium 30 be formatted in Apple's QuickDraw 3D data format, whereby the Mac OS computer 50 can quickly and easily access the 3-D computer model contained in first section 35 of data storage device or medium 30 and display images generated from that 3-D computer model on display 60.

In view of the foregoing, in the present invention it is also preferred that the 2-D slice image data contained in second section 40 of data storage device or medium 30 be formatted in Apple's QuickTime image data format. In this way computer 50 can quickly and easily display the scanned 2-D slice images obtained by scanning device 5. It will be appreciated that, to the extent that scanning device 5 happens to format its scanning data in the preferred QuickTime image data format, no reformatting of the 2-D slice image data will be necessary prior to storing the 2-D slice image data in second section 40 of data storage device or medium 30. However, to the extent that scanning device 5 happens to format its scanning data in a different data structure, reformatting of the 2-D slice image data will be necessary so as to put it into the preferred Quick-Time image data format. Such image data reformatting is of the sort well known in the art.

As a result of the foregoing, it will be seen that a physician operating computer 50 through input devices 55 can generate a desired image from the 3-D computer model contained within first section 35 of data storage device or medium 30. In particular, the physician can use input devices 55 to (1) open a window on display 60, (2) instruct the computer as to the desired angle of view, (3) generate the corresponding image of the scanned anatomical structure from the desired angle of view, using the 3-D computer model contained within first section 35 of data storage device or medium 30, and (4) display that image in the open window on display 60.

In addition, a physician operating computer 50 through input devices 55 can display a desired 2-D slice image from the 2-D slice image data contained within second section 40 of data storage device or medium 30. In particular, the physician can use input devices 55 to (1) open a window on display 60, (2) select a particular 2-D slice image contained within second section 40 of data storage device or medium 30, and (3) display that slice image in the open window on display 60.

More particularly, and looking now at FIGS. 9A-9F, computer 50 is preferably programmed so as to provide a variety of pre-determined menu choices which may be selected by the physician operating computer 50 via input devices 55.

Figure 10:
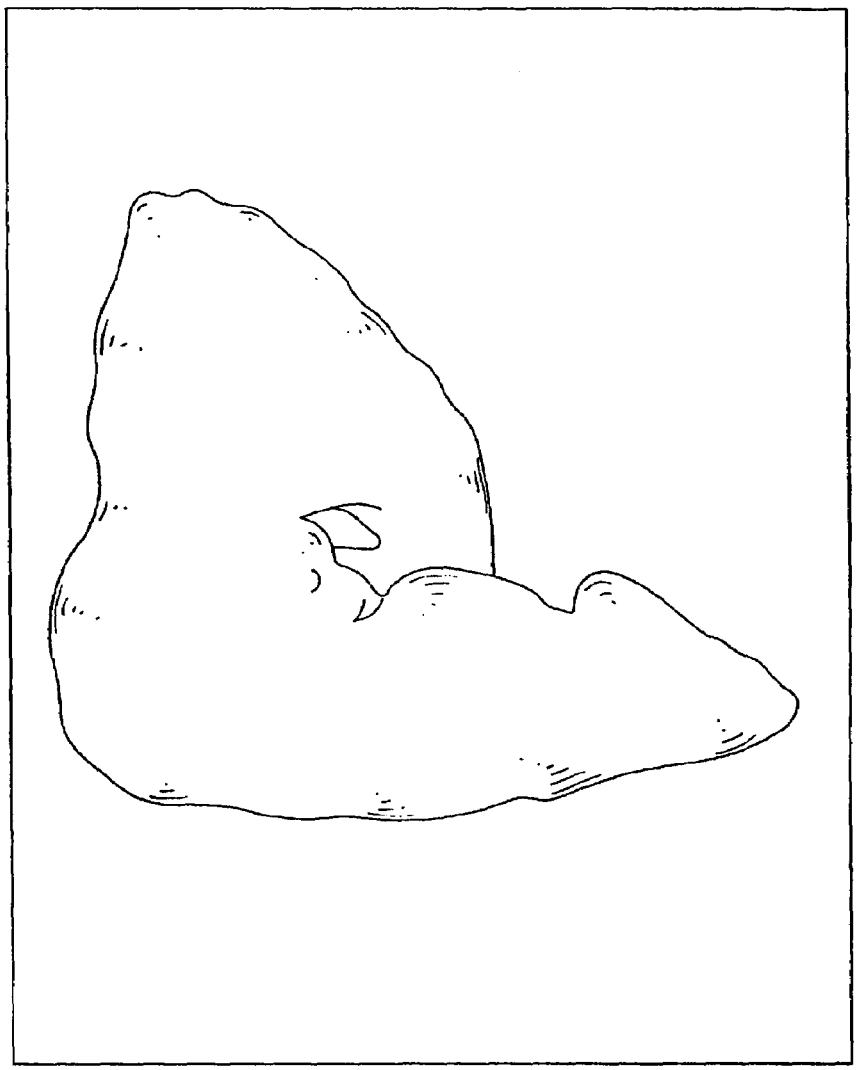
FIG. 10 illustrates an image drawn to a window using the data contained in the 3-D computer model associated with the present invention.

Thus, for example, if the physician wishes to produce a desired image from the 3-D computer model contained within first section 35 of data storage device or medium 30, the physician uses input devices 55 to invoke the command to display the 3-D computer model; the software then creates a window to display the image, it renders an image from the 3-D computer model contained within first section 35 of data storage device or medium 30, and then displays that image in the open window on display 60. By way of example, FIG. 10 illustrates an image drawn to a window using the data contained in the 3-D computer model stored in first section 35 of data storage device or medium 30. The physician can use input devices 55 to instruct the image rendering software as to the specific angle of view desired. In particular, computer 50 is preferably programmed so that the physician can depress a mouse key and then drag on the object so as to rotate the object into the desired angle of view. Additionally, computer 50 is preferably programmed so that the physician can also use the keyboard and mouse to move the view closer in or further out, or to translate the object side to side or up and down relative to the image plane. Programming to effect such computer operation is of the sort well known in the art.

Figure 11:
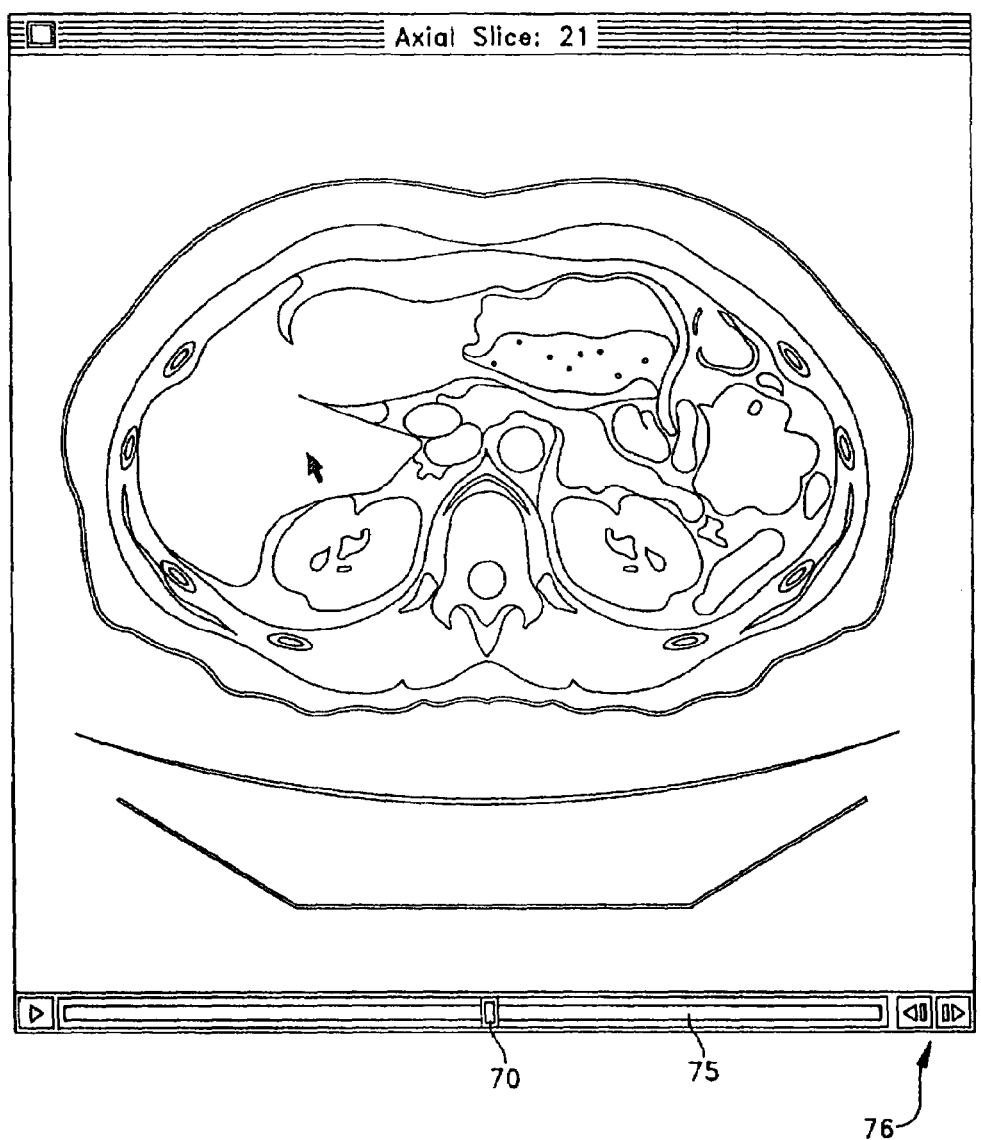
FIG. 11 illustrates a 2-D slice image drawn to a window in accordance with the present invention.

In a similar manner, the physician can use menu choices such as those shown in FIGS. 9A-9F to open a window on the display 60 and then to display in that window a desired 2-D slice image from second section 40 of data storage device or medium 30. Computer 50 is programmed so that the physician can select between different slice images by means of input devices 55. By way of example, FIG. 11 illustrates a 2-D slice image drawn to a window by the operating system using the data contained in second section 40 of data storage device or medium 30. In this case, computer 50 is programmed so that, by dragging icon 70 back and forth along slider 75, the physician can "leaf" back and forth through the collection of axial slices, i.e., in the example of FIG. 11, in which axial slice #21 is displayed, dragging icon 70 to the left might cause axial slice #20 to be displayed, and dragging icon 70 to the right might cause axial slice #22 to be displayed. Additionally, computer 50 is preferably programmed so that the physician can also step the image from the current slice number to a previous or following slice number by using menu commands or by clicking the mouse cursor on the single step icons 76 set at the right side of slider 75. Computer 50 is preferably also programmed so that menu commands are provided to change the slice window display directly to the first or last slice image in the 2-D slice image set, or to change the slice window display to a user-specified slice number. Programming to effect such computer operation is of the sort well known in the art.

Figure 12:
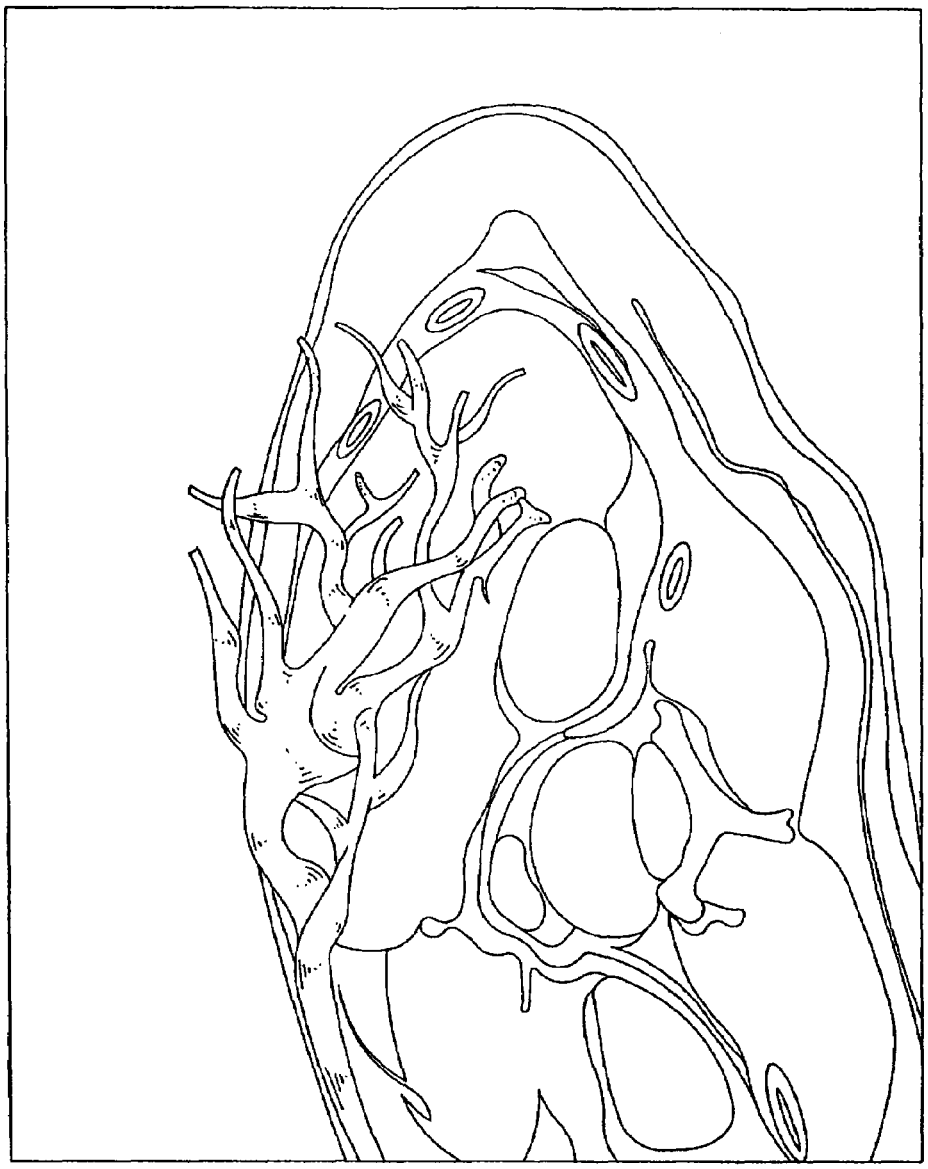
FIG. 12 illustrates a composite image formed from information contained in both the 3-D computer model and the 2-D slice image data structure.

As a consequence of using the aforementioned hardware and software architecture (i.e., the Macintosh computer, the Mac OS, the Apple QuickDraw 3D data format and software, and the Apple QuickTime image data format and software, or some equivalent hardware and software), it is possible to insert an additional software object into the 3-D computer model contained within first section 35 of data storage device or medium 30. In particular, it is possible to insert an additional software object having a "blank" planar surface into the 3-D computer model. Furthermore, using the computer's image rendering software, it is possible to texture map a 2-D slice image from second section 40 of data storage device or medium 30 onto the blank planar surface of the inserted software object. Most significantly, since the 3-D computer model is created out of the same scanning data as the 2-D slice images, it is possible to determine the specific 2-D slice image which corresponds to a given position of the blank planar surface within the 3-D computer model. Accordingly, with the present invention, when an image is generated from the 3-D computer model, both 3-D model structure and 2-D slice image structure can be simultaneously displayed in proper registration with one another, thereby providing a single composite image of the two separate images. See, for example, FIG. 12, which shows such a composite image. Again, computer 50 is programmed so that the physician can use input devices 55 to instruct the operating system's image rendering software as to where the aforementioned "additional" software object is to be inserted into the model and as to the particular angle of view desired. Programming to effect such computer operation is of the sort well known in the art.

Additionally, computer 50 is also programmed so that (1) the physician can use input devices 55 to select a particular 2-D slice image from the second section 40 of data storage device or medium 30, and (2) the computer will then automatically insert the aforementioned additional software object into the 3-D computer model so that the object's "blank" planar surface is located at the position which corresponds to the position of the selected 2-D slice image relative to the scanned anatomical structure. Again, programming to effect such computer operation is of the sort well known in the art.

In the foregoing description of the present invention, the 2-D slice image data generated by scanning device 5 has generally been discussed in the context of the standard "axial" slice images normally generated by scanning devices of the type associated with this invention. However, it is to be appreciated that the present invention is also adapted to utilize sagittal and/or coronal 2-D slice images. Furthermore, it is also to be appreciated that the present invention is adapted to utilize oblique slice images of the type hereinafter described.

Figure 13:
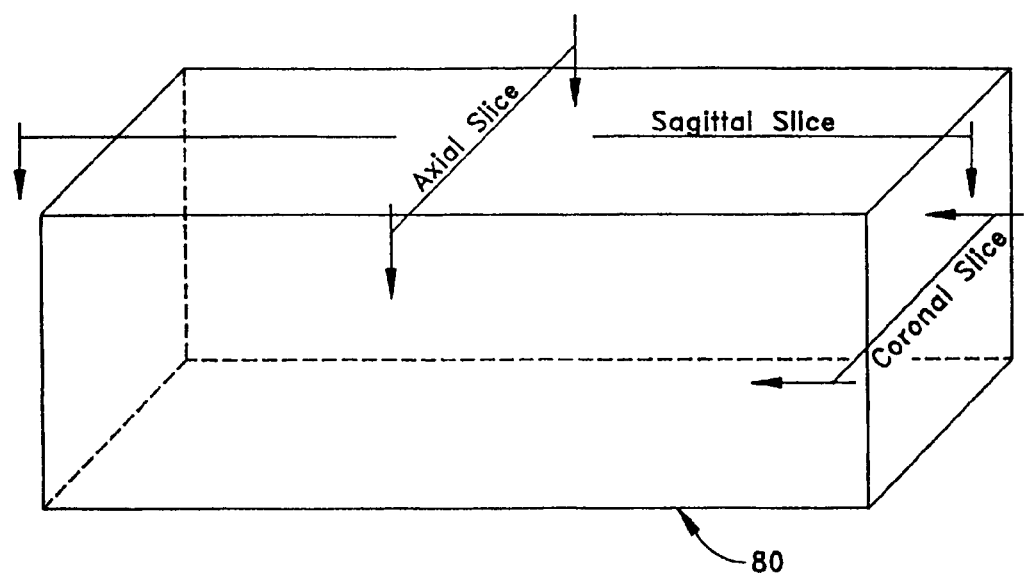
FIG. 13 is a schematic illustration showing the relationship between axial slices, sagittal slices and coronal slices.

More particularly, and looking next at FIG. 13, the relative orientation of axial, sagittal and coronal slice images are shown in the context of a schematic view of a human body 80. Scanning device 5 will normally generate axial slice image data when scanning a patent. In addition, in many cases scanning device 5 will also assemble the axial slice data into a 3-D database (i.e., a volumetric data set) of the scanned anatomical structure, and then use this 3-D database to generate a corresponding set of sagittal and/or coronal 2-D slice images. In the event that scanning device 5 does not have the capability of generating the aforementioned sagittal and/or coronal 2-D slice images, such sagittal and/or coronal 2-D slice images may be generated from a set of the axial 2-D images in a subsequent operation, using computer hardware and software of the sort well known in the art. Alternatively, if desired, computer 50 may be programmed to render such sagittal and/or coronal 2-D slices "on the fly" from the 2-D slice image data contained in second section 40 of data storage device or medium 30.

Figure 14:
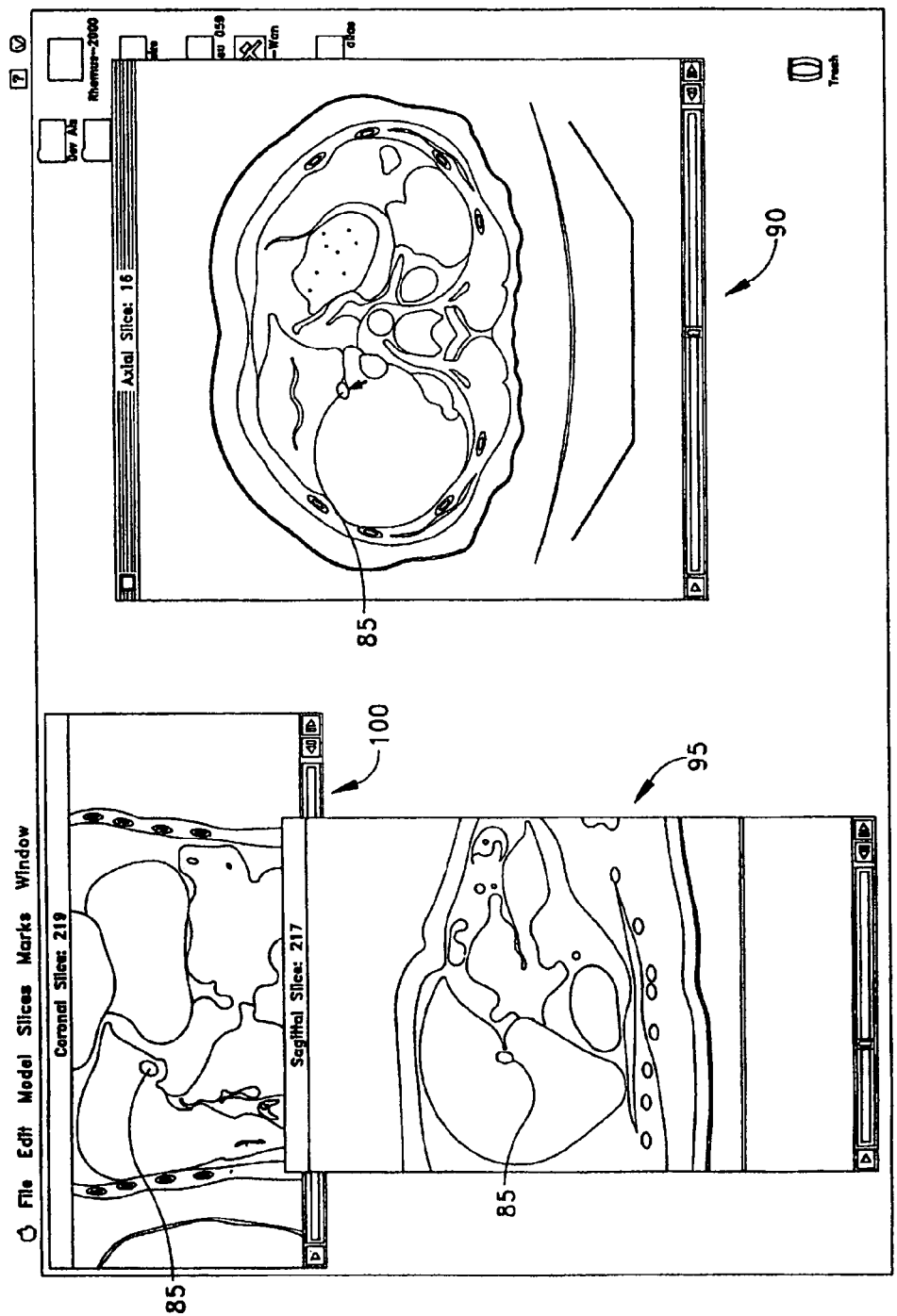
FIG. 14 illustrates three different images being displayed on a computer screen at the same time, with a marker being incorporated into each of the images.

In connection with the present invention, the sagittal and coronal 2-D slice image data may be stored with the axial slice image data in second section 40 of data storage device or medium 30. Preferably these sagittal and coronal slice images are stored in exactly the same data format as the 2-D axial slice images, whereby they may be easily accessed by computer 50 and displayed on display 60 in the same manner as has been previously discussed in connection with axial 2-D slice images. As a result, axial, sagittal and coronal 2-D slice images can be displayed on display 60, either individually or simultaneously in separate windows, in the manner shown in FIG. 14. Furthermore, when generating a composite image of the sort shown in FIG. 12 (i.e., an image generated from both the 3-D computer model contained in first section 35 of data storage device or medium 30 and a 2-D slice image contained in second section 40 of data storage device or medium 30), the composite image can be created using axial, sagittal or coronal 2-D slice images, as preferred.

It is also to be appreciated that the system of the present invention is also configured so as to generate and utilize oblique 2-D slice image data in place of the axial, sagittal and coronal slice image data described above. More particularly, computer 50 is programmed so that a physician can use input devices 55 to specify the location of the oblique 2-D slice image desired, and then computer 50 generates that 2-D slice image from the volumetric data set present in second section 40 of data storage device or medium 30 (i.e., from the collection of 2-D slice images contained in second section 40 of data storage device or medium 30).

It should be appreciated that data storage device or medium 30 can comprise conventional storage media (e.g., a hard disk, a CD ROM, a tape cartridge, etc.), which can be located either on-site or at a remote location linked via appropriate data transfer means.

Markers and Margins

In a further aspect of the present invention, computer 50 is programmed so that a physician can display a specific 2-D slice image in a window opened on display 60, place a marker into that specific 2-D slice image using a mouse or other input device 55, and then have that marker automatically incorporated into both (i) the 3-D computer model contained in first section 35 of data storage device or medium 30, and (ii) any appropriate 2-D slice image data contained in second section 40 of data storage device or medium 30. As a result, when images are thereafter generated from the 3-D computer model contained in first section 35 of data storage device or medium 30, and/or from the 2-D slice image data contained in second section 40 of data storage device or medium 30, these subsequent images will automatically display the marker where appropriate. See, for example, FIG. 14, which shows one such marker 85 displayed in its appropriate location in each of the three displayed 2-D slice images, i.e., in axial slice image 90, sagittal slice image 95, and coronal slice image 100. It is to be appreciated that it is also possible for marker 85 to be displayed where appropriate in an image generated from the 3-D computer model contained in first section 35 of data storage device or medium 30; see, for example, FIG. 15, which shows such a marker 85 being displayed in the image.

Figure 15:
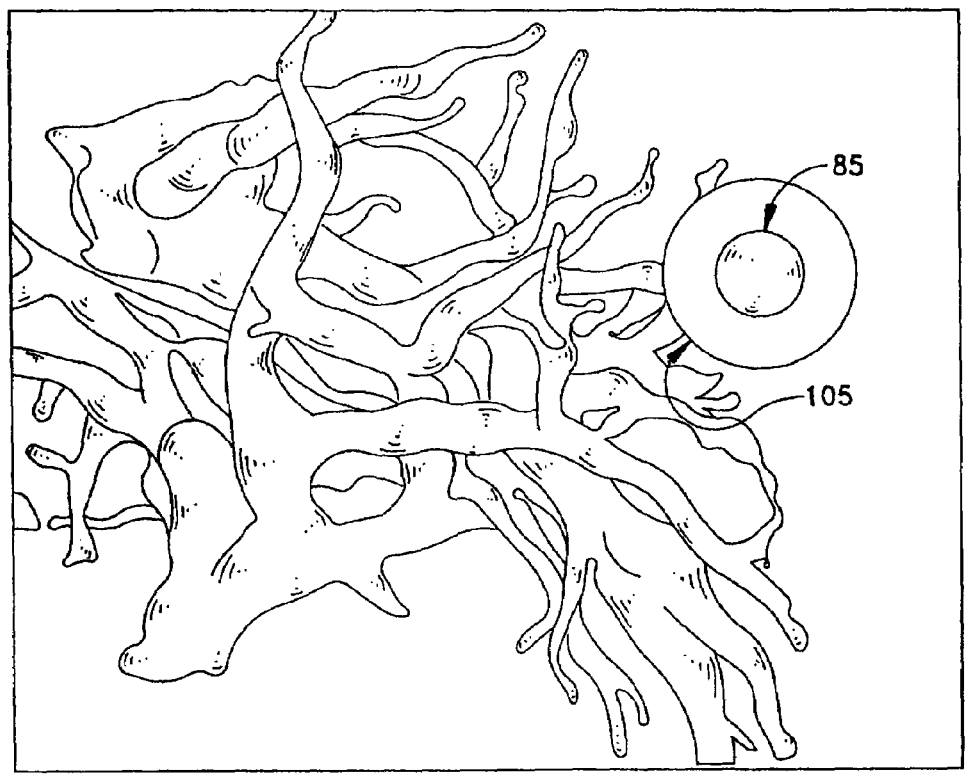
FIG. 15 illustrates a marker shown in an image generated from the 3-D computer model, with the marker being surrounded by a margin of pre-determined size.

In yet another aspect of the present invention, computer 50 is programmed so that a physician can generate a "margin" of some predetermined size around such a marker. Thus, for example, in FIG. 15, a margin 105 has been placed around marker 85. In this respect it is to be appreciated that margin 105 will appear as a 3-dimensional spherical shape around marker 85, just as marker 85 appears as a 3-dimensional shape, since the view of FIG. 15 is generated from the 3-D computer model contained in first section 35 of data storage device or medium 30. Alternatively, where marker 85 and margin 105 are displayed in the context of 2-D slice images, the marker and margin will appear as simple circles. Margin 105 can be used by a physician to determine certain spatial relationships in the context of the anatomical structure being displayed on the computer.

Peripheral Highlighting

Figure 16:
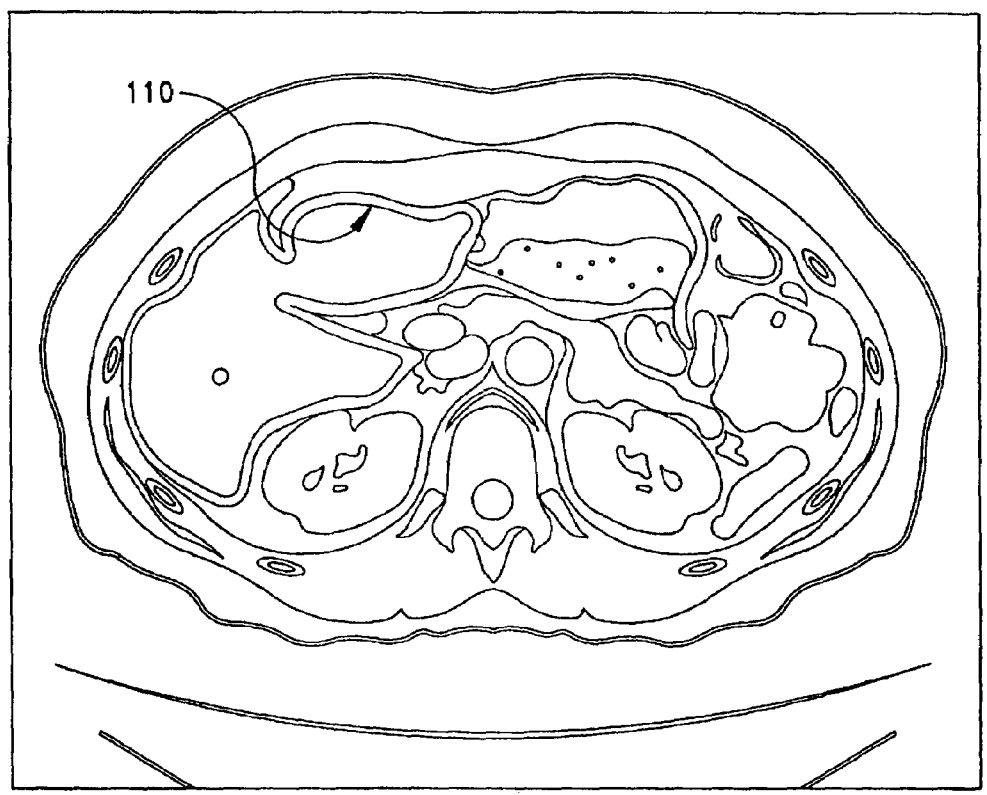
FIG. 16 illustrates a 2-D slice image, wherein the periphery of an object has been automatically highlighted by the system.

It is also to be appreciated that, inasmuch as the 3-D computer model contained in first section 35 of data storage device or medium 30 constitutes a plurality of software objects defined by polygonal surface models, it is possible to identify the periphery of any such objects in any corresponding 2-D slice image data contained in second section 40 of data storage device or medium 30. As a result, it is possible to highlight the periphery of any such object in any 2-D slice images displayed on display 60. Thus, in another aspect of the invention, computer 50 is programmed so that a physician can select one or more anatomical structures using an input device 55, and the computer will then highlight the periphery of that structure in any corresponding 2-D slice images displayed on display 60. See, for example, FIG. 16, where a boundary 110 is shown outlining the periphery of an object 115 displayed in a 2-D slice image.

Other Modifications of the Basic System

Furthermore, while in the foregoing description the present invention has been described in the context of an anatomical visualization system being used by a physician, it is also to be appreciated that the system could be used in conjunction with inanimate objects being viewed by a non-physician, e.g., the system could be used to visualize substantially any object for which a 3-D computer model and a collection of 2-D slice image data can be assembled.

It is also anticipated that one might replace the polygonal surface model discussed above with some other type of surface model. Thus, as used herein, the term "surface model" is intended to include polygonal surface models, parametric surface models such as B-spline surface models, quadrilateral meshes, etc.

Centerline Calculations

In yet another form of the present invention, the visualization and measurement system may incorporate means for determining patient-specific anatomical dimensions using appropriate scanned 2-D image data.

For purposes of illustration but not limitation, this aspect of the present invention will be discussed in the context of measuring a patient's vascular structure in the region of the aortic/iliac branching. By way of further example, such measurement might be conducted in the course of repairing an aortic aneurysm through installation of a vascular prosthesis.

Figure 17:
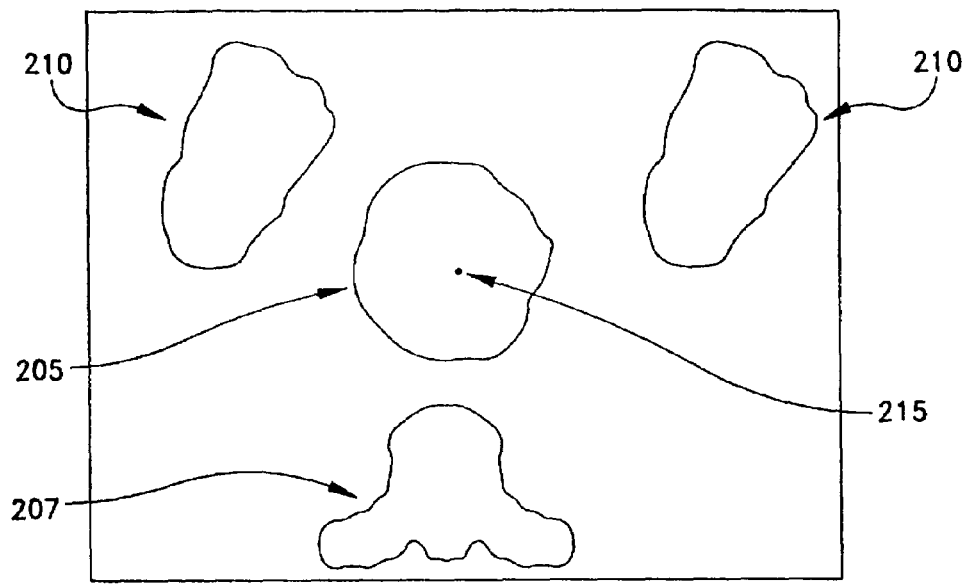
FIG. 17 is a schematic illustration showing various anatomical structures on a 2-D slice image, where that 2-D slice image has been taken axially through the abdomen of a patient, at a location above the aortic/iliac branching.
Figure 18:
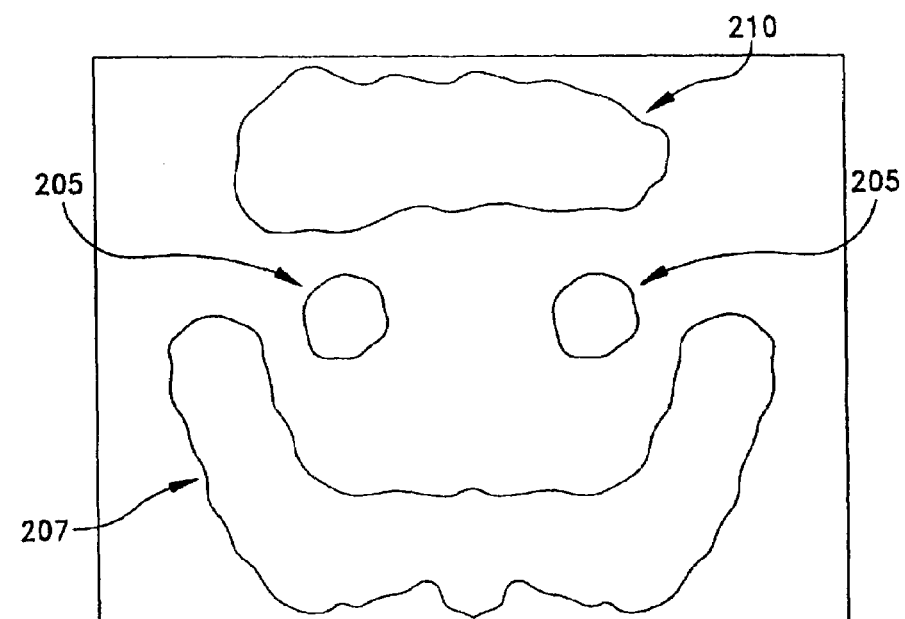
FIG. 18 is a schematic illustration showing various anatomical structures on another 2-D slice image, where that 2-D slice image has been taken through the abdomen of the same patient, at a location below the aortic/iliac branching.

More particularly, using the aforementioned scanning device 5, a set of 2-D slice images is first generated, where each 2-D slice image corresponds to a specific viewing plane or "slice" taken through the patient's body. As noted above, on these 2-D slice images, different types of tissue are typically represented by different image intensities. By way of example, FIG. 17 illustrates a 2-D slice image 200 taken through the abdomen of a patient, at a location above the aortic/iliac branching; FIG. 18 illustrates a 2-D slice image 202 taken through the abdomen of the same patient, at a location below the aortic/iliac branching. In these images, vascular tissue might be shown at 205, bone at 207, other tissue at 210, etc. An appropriate set of these 2-D slice images is assembled into a 3-D database so as to provide a volumetric data set corresponding to the anatomical structure of the patient. Referring back to the system illustrated in FIG. 6, the set of 2-D slice images making up this 3-D database might be stored in second section 40 of data storage device or medium 30. In this respect it is also to be appreciated that the 3-D database being referred to now is not the same as the 3-D computer model contained in first section 35 of data storage device or medium 30; rather, the 3-D database being referred to now is simply a volumetric data set made up of the series of 2-D slice images contained in second section 40 of data storage device or medium 30.

Next, using the appropriately programmed computer 50, the patient-specific volumetric data set (formed out of the collection of 2-D slice images contained in the 3-D database) is segmented so as to highlight the anatomical structure of interest.

This is preferably effected as follows. On the computer's display 60, the user is presented with 2-D slice images from the 3-D database, which images are preferably stored in second section 40 of data storage device or medium 30. As noted above, each of these 2-D images corresponds to a specific viewing plane or "slice" taken through the patient's body; or, stated slightly differently, each of these 2-D images essentially represents a plane cutting through the patient-specific volumetric data set contained in the 3-D database. As also discussed above, with each of these 2-D slice images, the different types of tissue will generally be represented by different image intensities. Using one or more of the input devices 55, e.g., a mouse, the user (who might or might not be a physician) selects a particular 2-D slice image for viewing on display 60, e.g., "slice image #155". The user then uses one or more of the input devices 55 to select one or more points located within the anatomical structure of interest. For convenience, such user-selected points can be referred to as "seeds". See, for example, FIG. 17, where a seed point 215 has been selected within the interior of vascular tissue 205 so as to identify blood. The user also uses one or more of the input devices 55 to specify a range of image intensities that appear to correspond to the anatomical structure of interest in the volumetric data set, e.g., blood within the interior of a blood vessel.

Figure 17A:
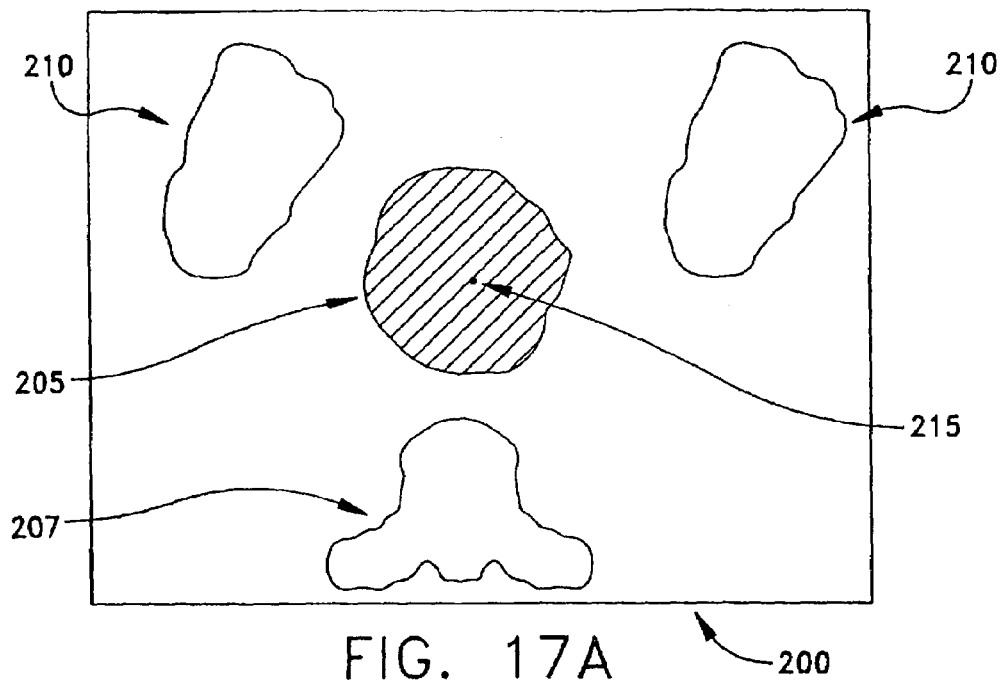
FIGS. 17A and 18A are schematic illustrations like those of FIGS. 17 and 18, respectively, except that segmentation has been performed in the 3-D database so as to highlight the patient's vascular structure.
Figure 18A:
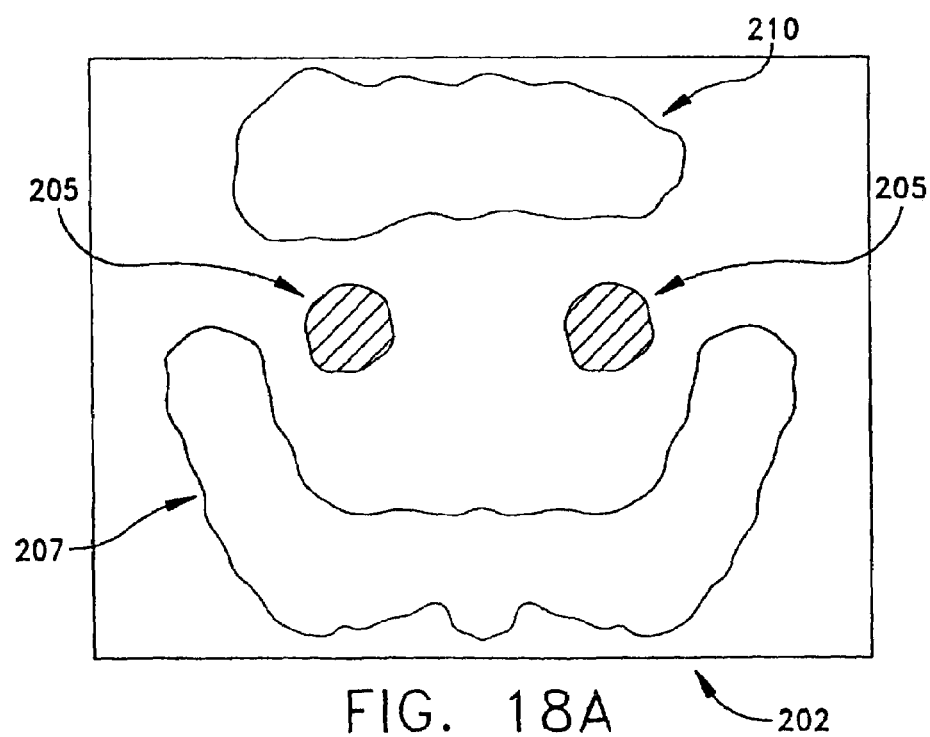

In accordance with the present invention, the appropriately programmed computer 50 then applies a segmentation algorithm of the sort well known in the art to segment out related structure within the patient-specific 3-D database. Preferably computer 50 is programmed to apply a 3-D connected component search through the volumetric data set contained in second section 40 of data storage device or medium 30 so as to determine the set of volumetric samples that are (i) within the range specified for blood, and which (ii) can be connected along a connected path back to one of the seeds, where each of the locations along the path is also within the range specified for blood. The result of this 3-D connected component search is a set of 3-D locations in the volumetric data set which correspond to blood flowing through the blood vessel. For the purposes of the present illustration, this set of 3-D locations can be characterized as the "blood region". The segmented anatomical structure (i.e., the blood in the blood region) can then be highlighted or otherwise identified on each of the 2-D slice images. See, for example, FIGS. 17A and 18A, where the segmented blood region in vascular tissue 205 has been cross-hatched to represent such highlighting.

Next, the branches in the segmented anatomical structure are identified. For example, and looking now at FIG. 19, in the present illustration dealing with vascular structure in the region of the aortic/iliac branching, the aorta and the two iliac branches would be separately identified.

This is done in the following manner. For each of the vessel segments that are part of the branching structure of interest, the user specifies a branch line in the volumetric data set that uniquely indicates that vessel segment. This is accomplished by using one or more of the input devices 55 to select, for each branch line, an appropriate "start" location on one of the 2-D slice images contained within second section 40 of data storage device or medium 30, and an appropriate "end" location on another one of the 2-D slice images contained within second section 40 of data storage device or medium 30. It should be appreciated that these branch lines do not need to cover the entire length of interest of the vessel and, in practice, will tend to stop somewhat short of the junction where various branches converge with one another. At the same time, however, for improved accuracy of modeling the branching structure, the branch lines should extend close to the bifurcation point.

For each of the vessel branches, the start and end locations are used to subdivide the blood region as follows: the region for that vessel branch is the set of locations within the blood region that are between the start plane and the end plane, where the start plane for each vessel branch is the 2-D image plane passing through the start location for the corresponding branch line, and the end plane for each vessel branch is the 2-D image plane passing through the end location for each vessel branch.

Figure 19:
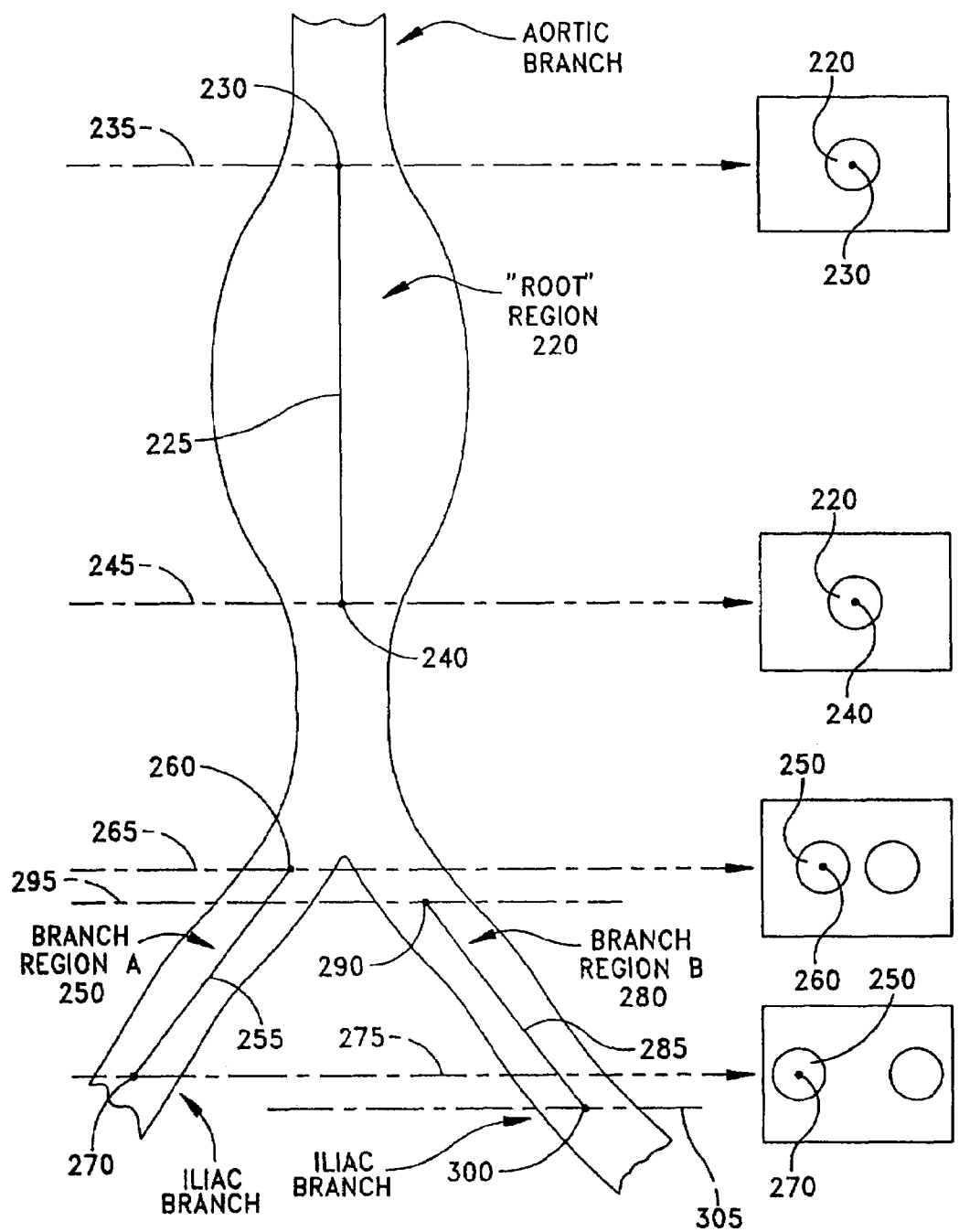
FIG. 19 is a schematic illustration showing that same patient's vascular structure in the region about the aortic/iliac branching, with branch lines having been specified for the patient's aorta and two iliac branches.

Although the invention could be used for a more complex branching structure through obvious extensions, it is useful to consider a vessel branch structure consisting of just three vessel segments coming together at a branch point, e.g., a vessel branch structure such as the aortic/iliac branching shown in FIG. 19. In this case, the user would designate one vessel region as the root region (e.g., the aortic region 220 defined by a branch line 225 having a start location 230 contained in a start plane 235, and an end location 240 contained in an end plane 245) and the other vessel regions as branch region A (e.g., the iliac region 250 defined by a branch line 255 having a start location 260 contained in a start plane 265, and an end location 270 contained in an end plane 275), and branch region B (e.g., the iliac region 280 defined by a branch line 285 having a start location 290 contained in a start plane 295, and an end location 300 contained in an end plane 305), respectively.

Figure 20:
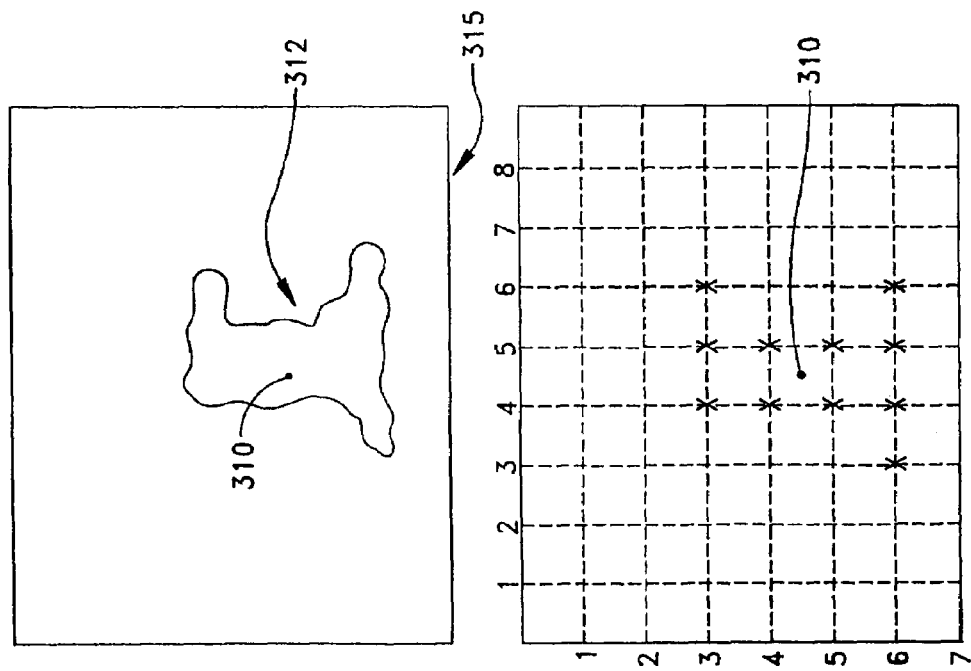
FIG. 20 is a schematic illustration showing how the centroid is calculated for the branch structure contained in a particular scanned 2-D image.

For each of the vessel regions determined in the previous step, a centroid path is then calculated. This is accomplished in the following manner. First, at intervals along the vessel line corresponding to the volumetric location of each of the original 2-D slice images contained in second section 40 of data storage device or medium 30, the centroid of the vessel region in that particular 2-D slice image is calculated. This is done by averaging the image coordinates of all locations in that 2-D slice image that are within the vessel region so as to yield a centroid point. See, for example, FIG. 20, which schematically illustrates the manner of calculating the centroid 310 for a representative vessel region 312 in a representative 2-D slice image 315.

Figure 21:
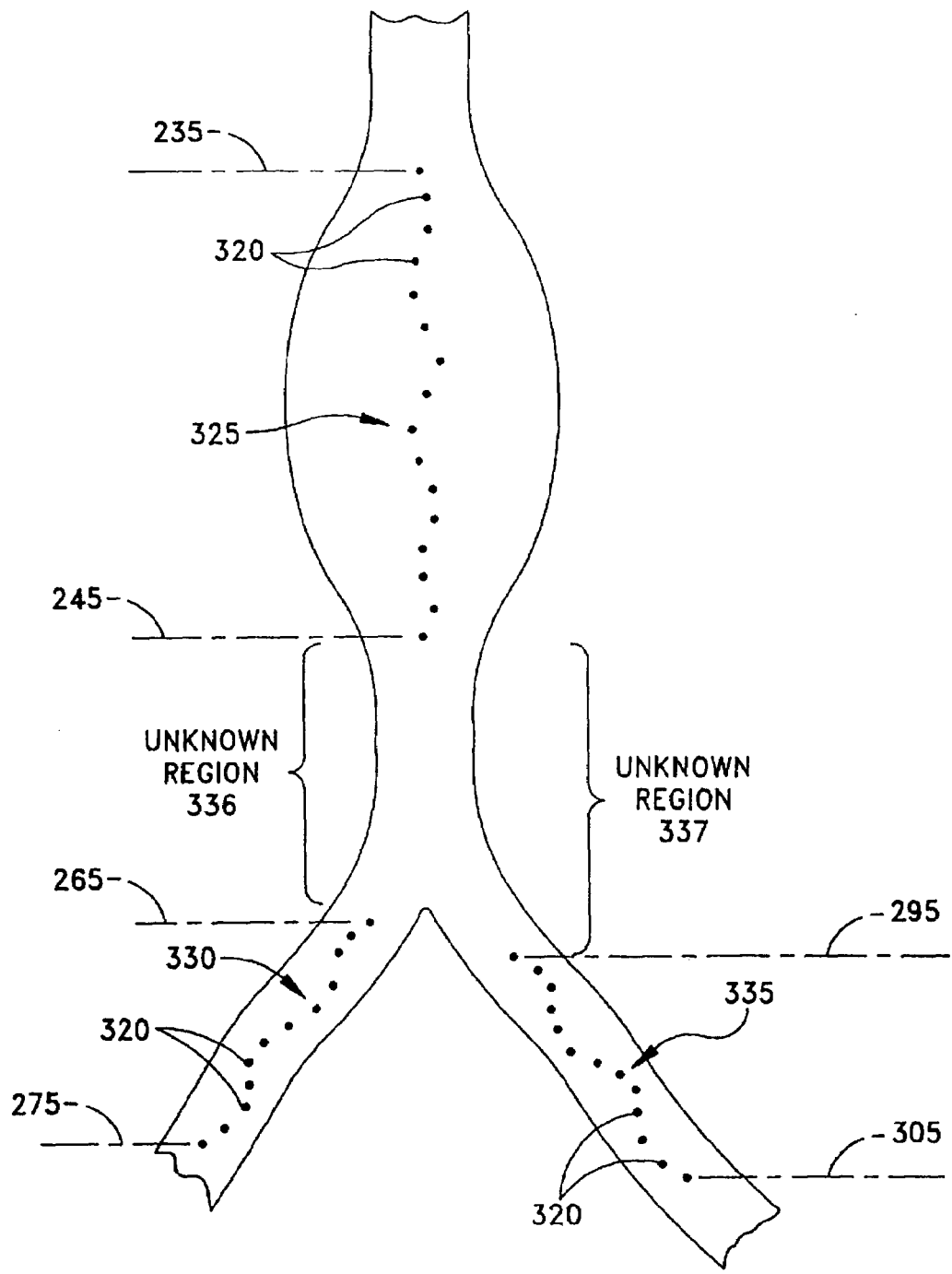
FIG. 21 is a schematic illustration showing the tortuous centroid path calculated for each of the respective branch lines shown in FIG. 19.

The centroid path for each vessel region is then established by the collective set of centroid points located along that vessel segment in three-dimensional space. The tortuous path corresponding to the root region is called the root centroid path and the tortuous paths corresponding to branch regions A and B are called branch centroid path A and branch centroid path B, respectively. See, for example, FIG. 21, which shows a plurality of centroids 320, a root centroid path generally indicated at 325, a branch centroid path A generally indicated at 330, and a branch centroid path B generally indicated at 335, all shown in the context of a vessel branch structure such as the aortic/iliac branching example discussed above. It is to be appreciated that no centroids will be defined in the "unknown" region 336 bounded by the end plane 245 and the start plane 265, and the "unknown" region 337 bounded by the end plane 245 and the start plane 295.

The system is programmed so that it will then apply a curve-fitting algorithm to the tortuous centroid paths determined above so as to supply estimated data for any portions of the anatomical structure which may lie between the aforementioned branch lines, and for "smoothing out" any noise that may occur in the system.

Figure 22:
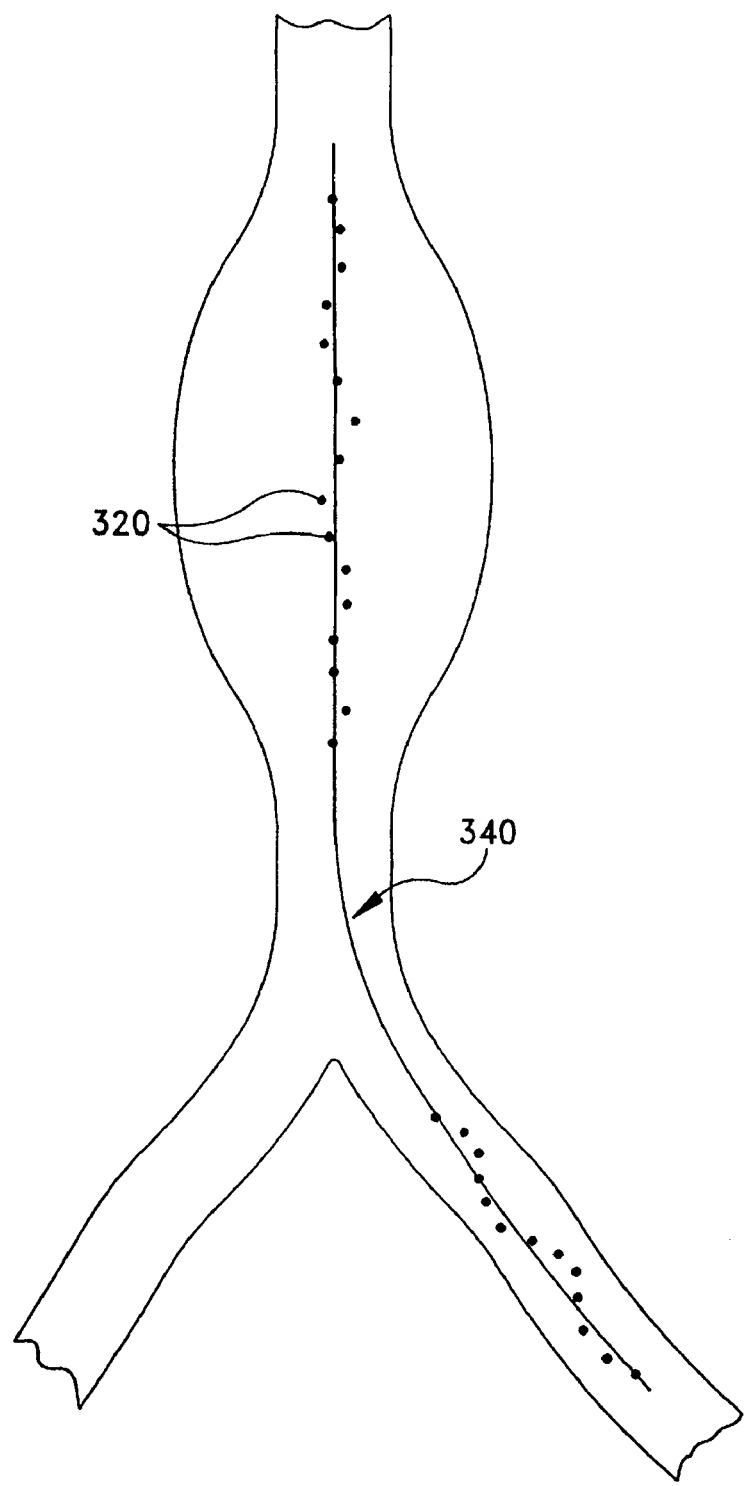
FIG. 22 is a schematic illustration showing the space curve determined by applying a curve-fitting algorithm to two of the centroid paths shown in FIG. 21, whereby the structure between the branch lines is filled out and the centroid data "smoothed" through a "best fit" interpolation technique.

This is preferably done through a spline fitting algorithm effected in the following manner. First, two new paths are created, by concatenating the points in the root centroid path 325 with the points in each of the two branch centroid paths 330 and 335, so as to create a path root-A and a path root-B. These two new paths are then used as the input to a spline fitting routine which selects the coefficients for a piecewise polynomial space curve that best approximates the points along the path in a least-squares sense. The number of pieces of the approximation and the order of polynomial may be varied by the user. The resulting curves may be called spline-root-A and spline-root-B. See, for example, FIG. 22, which illustrates the spline-root-B, generally indicated at 340.

Through numerical integration, the distance along the two splines (i.e., spline-root-A and spline-root-B) can then be calculated using standard, well-known techniques, and the result can be presented to the user. These calculations can be used for a variety of purposes, e.g., to help determine the appropriate size of a vascular prosthesis to be used in repairing an aneurysm at the aortic/iliac junction.

In addition, using well established mathematical techniques, at any point along the spline paths, a tangent vector and a perpendicular plane can be readily determined either by direct calculation or by definition in those cases where direct calculation would be undefined. By calculating the distance from the spline path to the points in the volumetric data set corresponding to the vessel branch region that are within an epsilon distance of the perpendicular plane, the shape of the vessel at that point can be determined, and the radius of a circle that best fits the cross-sectional area of the vessel at that point can also be readily calculated. Again, this result can be used to help determine that desired graft shape.

Figure 23:
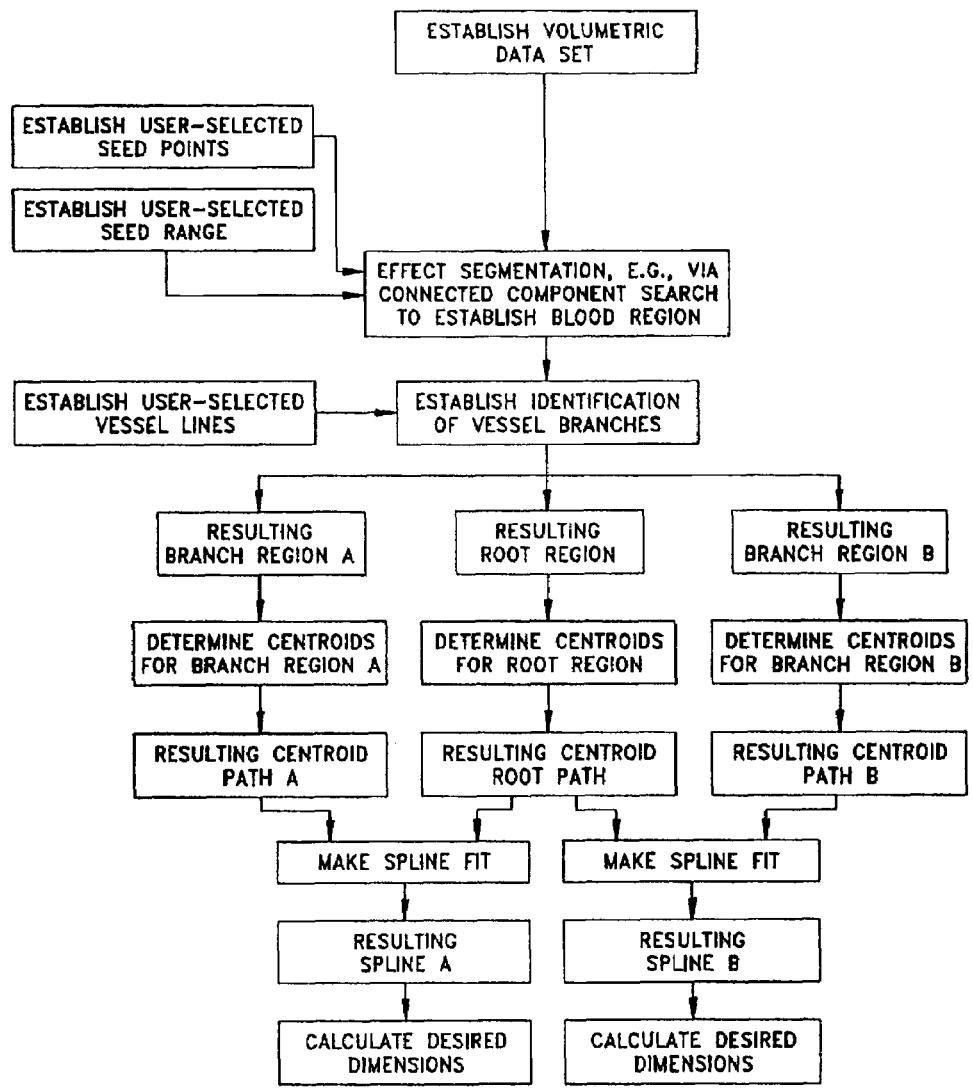
FIG. 23 is a flow chart illustrating how patient-specific anatomical dimensions can be determined from scanned 2-D image data in accordance with the present invention.

FIG. 23 is a flow chart illustrating how patient-specific anatomical dimensions can be determined from scanned 2-D data in accordance with the present invention.

In addition to the foregoing, it is possible to use the centerline derived above to generate additional views for the observer, and/or to make further anatomical calculations and measurements.

Oblique Slices Derived from the Centerline

Among other things, it is possible to use the centerline derived above to construct a series of oblique slices through the volumetric data set (which volumetric data set is formed out of the assembled scanned 2-D slice images contained in second section 40 of data storage device or medium 30) such that the reconstructed oblique slices are disposed perpendicular to the centerline.

More particularly, oblique slices per se are generally well known in the art, to the extent that such oblique slices are arbitrary planar resamplings of the volumetric data set. However, the utility of these arbitrary oblique slices is limited for many applications, since there is no explicit, well-defined relationship between their position and anatomical structures of interest. By way of example, in the case of blood vessels, oblique slices taken perpendicular to the length of the blood vessel are of particular importance to the physician. However, when generating oblique slices using traditional techniques (e.g., by pointing with an input device 55 while viewing the display 60), it is very difficult for the physician to specify the oblique slice which is truly perpendicular to the blood vessel at a specified point. This problem is avoided with the present invention, which utilizes the centerline as derived above to generate the set of oblique slices lying perpendicular to the blood vessel. This set of oblique slices derived from the centerline is preferably stored in a fourth section 400 of data storage device or medium 30 (FIGS. 5 and 6).

In general, one way to think about generating any oblique slice is to consider a four-sided polygon that is placed in the space defined by the volumetric data set. This polygon is then scan converted to resample the axial images so as to generate the oblique slice desired. As used herein, the term "scan converted" is intended to refer to the well-known techniques of subdividing a polygon into regularly spaced intervals on a rectangular grid.

Figure 24:
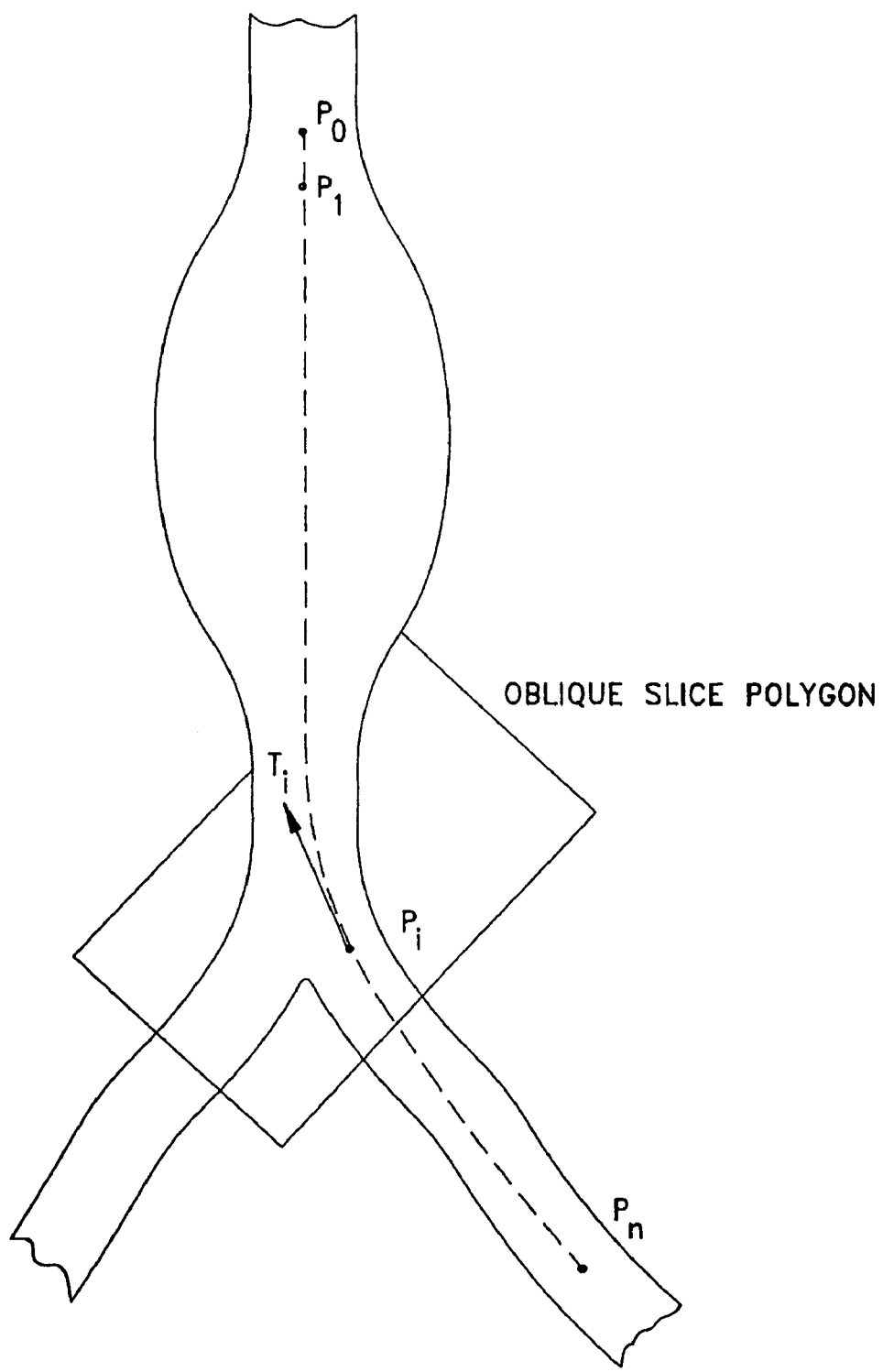
FIG. 24 is a schematic view showing an oblique slice polygon disposed perpendicular to the centerline of a blood vessel.

In the present invention a programmable computer is used to generate the specific set of oblique slices that is defined by the centerline derived above. This is accomplished as follows. First, the centerline is divided into n increments. This can be done with points $P_0, P_1, \ldots, P_n$, as shown in FIG. 24. A line $T_i$ is then derived for each of the points $P_i$, where $T_i$ is the tangent line at that point $P_i$. Finally a series of oblique slices are produced by constructing a series of four-sided polygons, each of which is centered at $P_i$ and normal to $T_i$. The locations of the corners of the polygon are selected such that the resulting image orientation is as close as possible to a pre-selected image orientation (e.g., axial). These four-sided polygons are then scan converted as described above so as to provide the set of oblique slice images lying perpendicular to the centerline. As noted above, this set of oblique slice images is stored in fourth section 400 of data storage device or medium 30. At the same time, the corner locations of each four-sided polygon associated with each oblique slice image is also stored in fourth section 400 of data storage device or medium 30, whereby the precise location of each oblique slice image within the volumetric data set is established.

As a result of the foregoing, the oblique slice images stored in fourth section 400 of data storage device or medium 30 is available to be accessed by computer 50 in exactly the same manner as the 2-D axial slice images stored in second section 40 of data storage device or medium 30.

Furthermore, once the aforementioned oblique slices have been derived from the centerline, these oblique slices can then be used for a variety of additional purposes.

Measuring Diameters Along the Centerline

As noted above, the oblique slice images derived from the centerline can be accessed by computer 50 from fourth section 400 of data storage device or medium 30. The physician can then use input devices 55 to instruct computer 50 to access the oblique slice at a particular location along the blood vessel and measure the diameter of the same. In particular, the physician can use input devices 55 to access the particular oblique slice desired and then lay down two diametrically-opposed marks so as to define the diameter of the blood vessel; the computer is adapted in ways well known in the art to then calculate the distance between the two marks. In this respect it should be appreciated that since the aforementioned oblique slice images are, by definition, taken perpendicular to the blood vessel at each point along the blood vessel, the blood vessel diameters so measured will tend be much more accurate than diameters calculated solely off axial slice images, and/or off coronal and/or sagittal and/or "standard", non-centerline-derived oblique slice images.

Measuring Distances with Cumulative Sum Table

It has also been found that it can be advantageous to store the incremental distances between the centerline points $P_1, P_2, \ldots, P_n$, in a cumulative sum table in which the first entry, $C_0$, is 0; the second entry, $C_1$, is the distance between $P_1$ and $P_0$ (i.e., $C_1=P_1-P_0$) ; the third entry $C_2=C_1+(P_2-P_1)$ ; etc. Thus, the centerline distance between any two points $P_i$ and $P_j$ is simply $D_{ij}=C_i-C_j$.

Figures 25, 26:
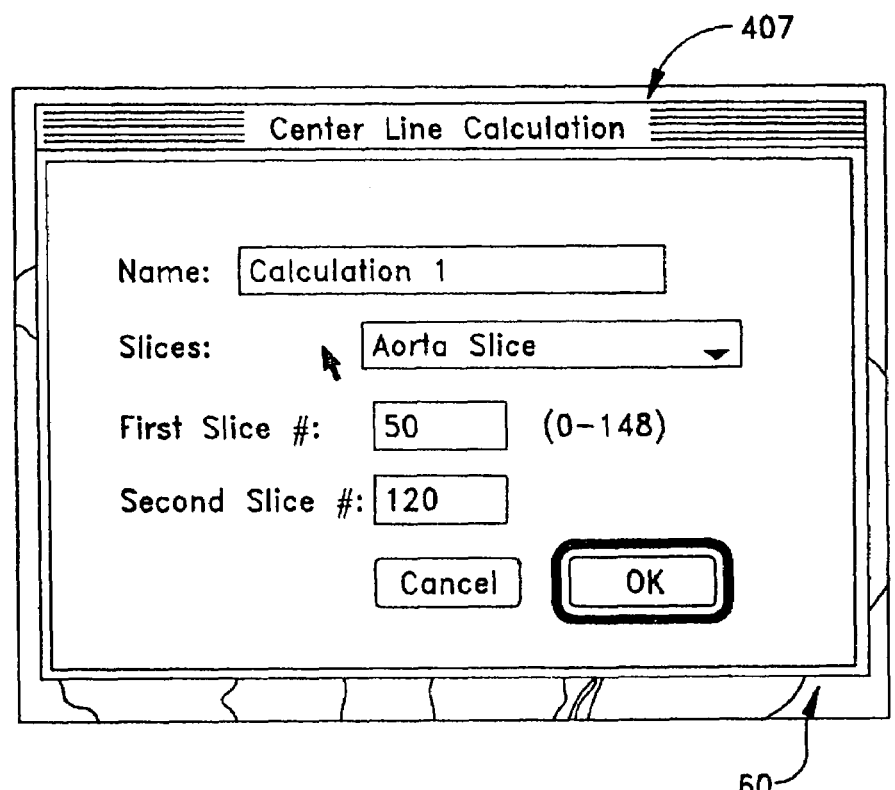
FIG. 25 is a cumulative sum table for calculating lengths along an anatomical structure.
FIG. 26 illustrates a centerline length calculation dialogue box drawn to a window in a display.

In the present invention, the cumulative sum table can be of the sort shown in FIG. 25. This cumulative sum table is preferably stored in a fifth section 405 of data storage device or medium 30. Computer 50 is also programmed so that the user interface presents a centerline length calculation dialogue box 407 (FIG. 26) to the physician on display 60, by which the physician can specify (using input devices 55) two oblique slice images which are the end points of the length which is to be determined. Computer 50 is programmed so that it will then determine the length between the two chosen oblique slices by calculating the difference in their positions from the cumulative sum table.

Figure 27:
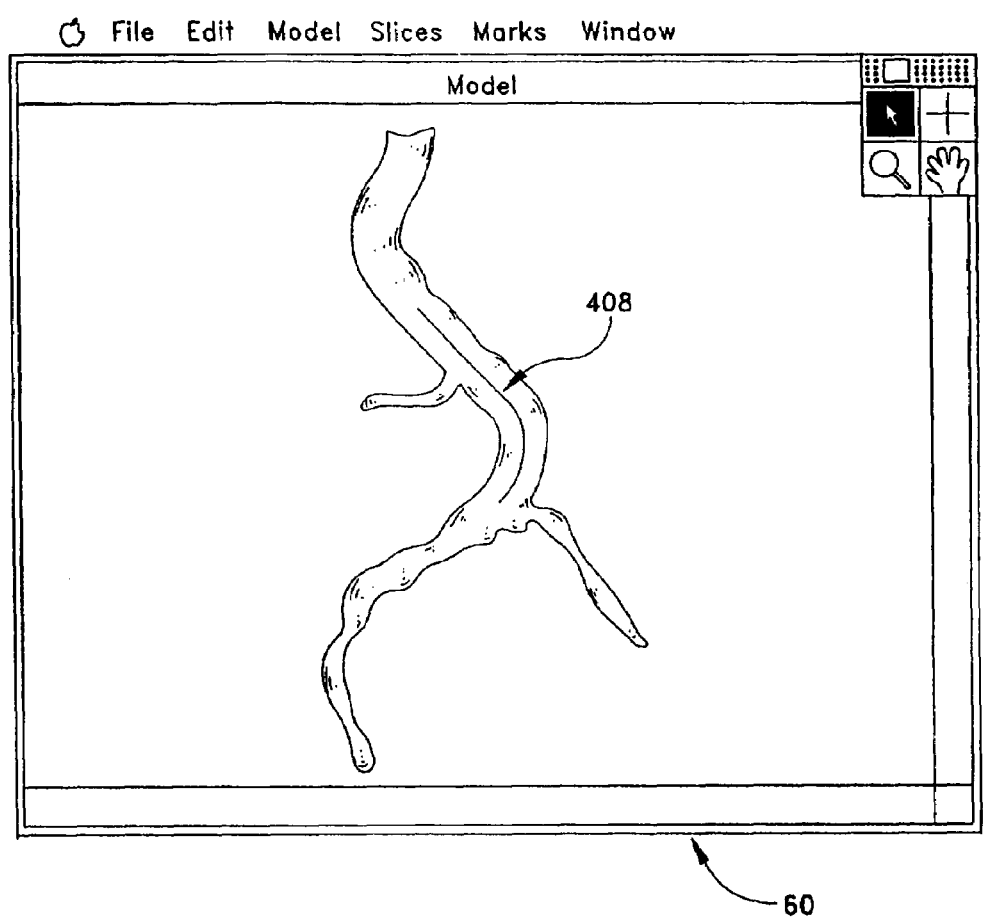
FIG. 27 illustrates a 3-D graphical icon which has been inserted into the 3-D model and which is visible on the display so as to show the portion of the centerline which has been specified by the physician for a length calculation.

Computer 50 is also programmed so that a 3-D graphical icon 408 (FIG. 27) is inserted into the 3-D model contained in first section 35 of data storage device or medium 30. This icon represents the portion of the vessel centerline which has been specified by the physician via the two oblique slice images which represent the length end points.

Calculating Volumes Using a Cumulative Sum Table

A cumulative sum table can also be used to calculate volumes with respect to an anatomical structure, in much the same way that a cumulative sum table can be used to calculate lengths along an anatomical structure. However, incremental slice volumes are more appropriately calculated in the axial direction rather than in the oblique slice direction. This is because the axial slices all lie parallel to one another, whereas the oblique slices (since they are generated from the centerline) do not.

Figures 28, 29:
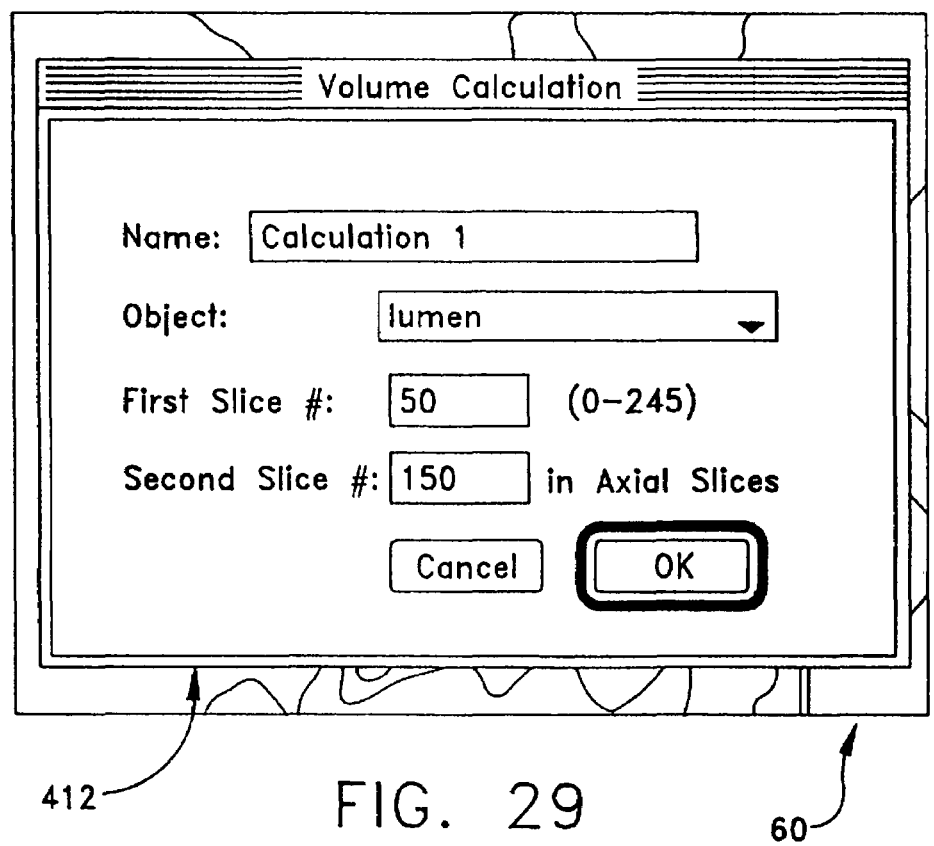
FIG. 28 is a cumulative sum table for calculating volumes with respect to an anatomical structure.
FIG. 29 illustrates a volume calculation dialogue box drawn to a window in a display.
Figure 30:
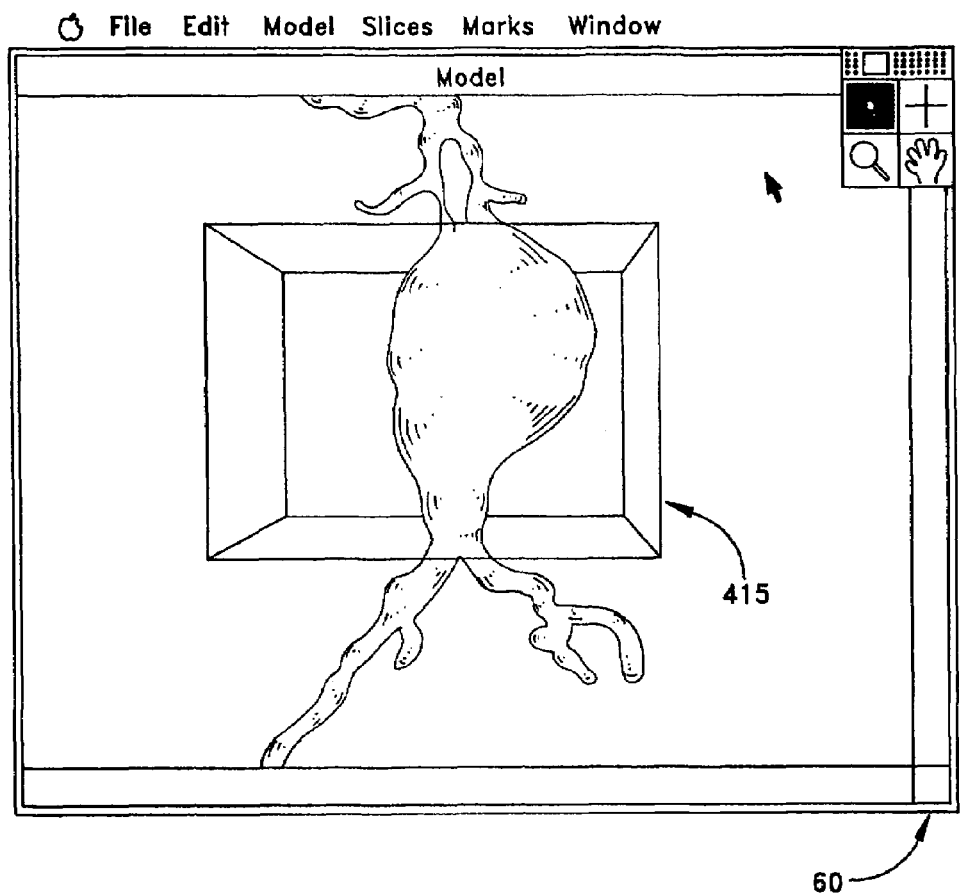
FIG. 30 illustrates a 3-D graphical icon which has been inserted into the 3-D model and which is visible on the display so as to show the volume which has been specified by the physician using the volume calculation dialogue box.

To this end, a computer is used to calculate the volume of each axial slice, $V_i$, by (1) determining the number of pixels in the segmented region of that axial slice, (2) scaling by the appropriate pixel-to-length factor, and then (3) multiplying by the slice thickness. A cumulative sum table is then generated, where the first entry, $C_0$, is $V_0$; the second entry, $C_1=C_0+V_1$; the third entry $C_2=C_1+V_2$; etc. In the present invention, this cumulative sum table can be of the sort shown in FIG. 28. This cumulative sum table is stored in sixth section 410 of data storage device or medium 30. Computer 50 is also programmed so that the user interface presents a volume calculation dialogue box 412 (FIG. 29) to the physician on display 60 that allows the physician to conveniently specify two axial slices as the end points of the volume to be determined. Computer 50 then calculates the volume for the region specified, using the cumulative sum table. Computer 50 is also programmed so as to place a 3-D graphical icon 415 (FIG. 30) in the 3-D model contained in the first section 35 of data storage device or medium 30. This icon represents the volume specified by the physician using the volume calculation dialogue box.

Virtual Grafts

In the preceding description, anatomical 3-D computer models were created from software objects representing anatomical objects (e.g., a first software object to represent a liver, a second software object to represent an aorta, etc.); and additional software objects were created to represent non-anatomical objects (e.g., markers 85, margins 105, boundaries 110 and graphical icon 408); and the various software objects (representing both anatomical and non-anatomical objects) were placed into proper registration with one another using techniques well known in the art so as to form a cohesive database for the application program's image rendering software. Accordingly, the program's image rendering software can render images showing both anatomical objects and non-anatomical objects from various points of view, with the anatomical objects and the non-anatomical objects being in proper registration with one another.

In this respect it should be appreciated that it is also possible to create further software objects, in addition to those anatomical objects (e.g., liver, blood vessels, etc.) and non-anatomical objects (e.g., markers 85, margins 105, boundaries 110 and graphical icon 408) disclosed above, and to place those additional objects the system's database for selective viewing by the system's image rendering software.

Of particular significance is the ability to create software objects representing implantable devices, and to place such software objects in registration with software objects representing a patient's anatomy, in advance of an actual surgery, whereby to enhance appropriate implant selection and facilitate surgical planning.

Figure 31:
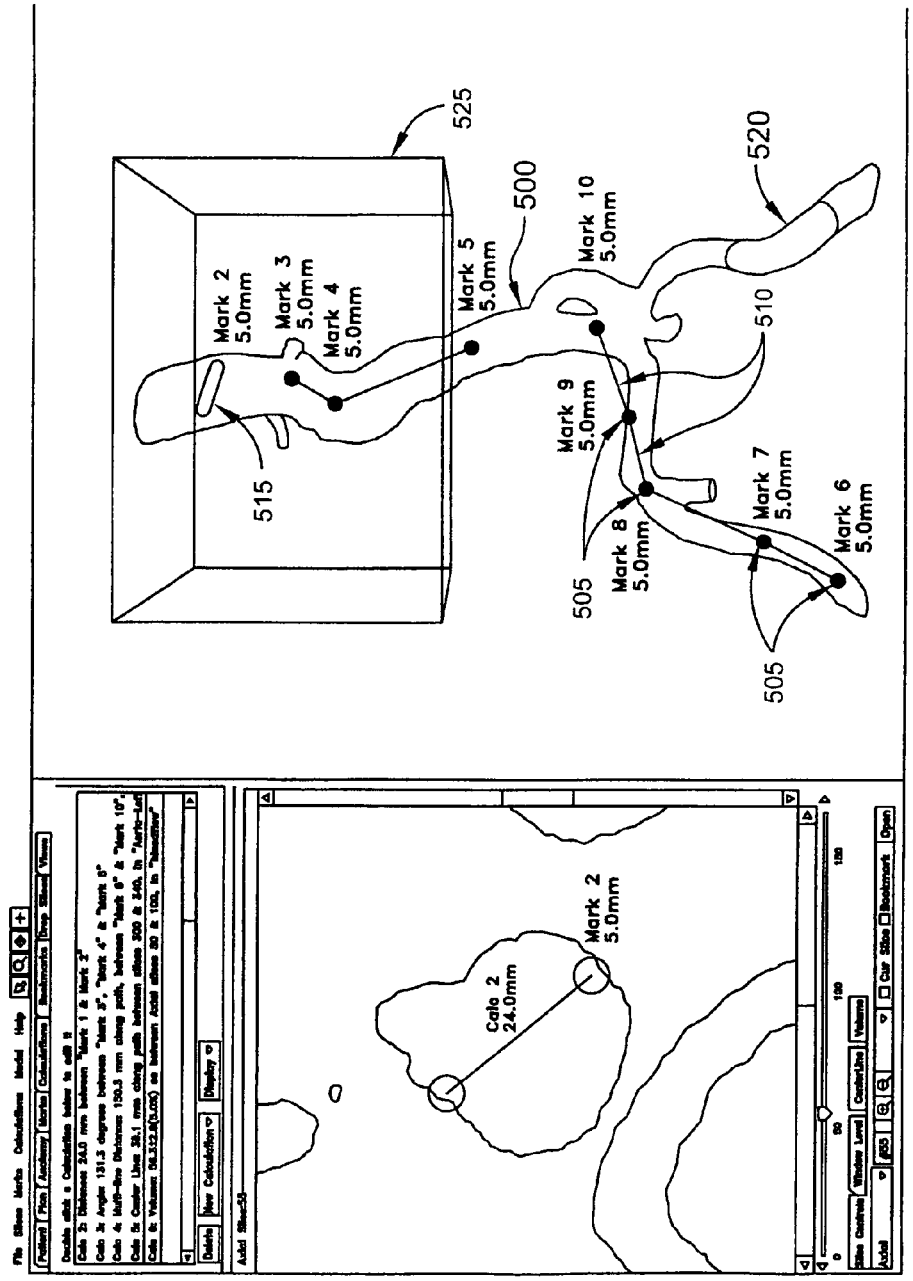
FIG. 31 is a schematic representation of a software object representing the aorta of a patient.

By way of example, and looking now at FIG. 31, there is shown a software object 500 representing the aorta of a patient. Also shown is a series of markers 505 placed into the system (e.g., by a human operator using a mouse) and a series of line segments 510 extending between selected ones of the markers 505. These markers 505 and line segments 510 may be used to plan a surgical procedure, to determine anatomical lengths or angles, etc.

Also shown is a straight tube 515 which may also be used for planning and measurement purposes, etc., a curved tube 520 which may be used for planning and measurement purposes, and a box 525 which may be used for planning and measurement purposes, e.g., for volume calculations.

Figure 32:
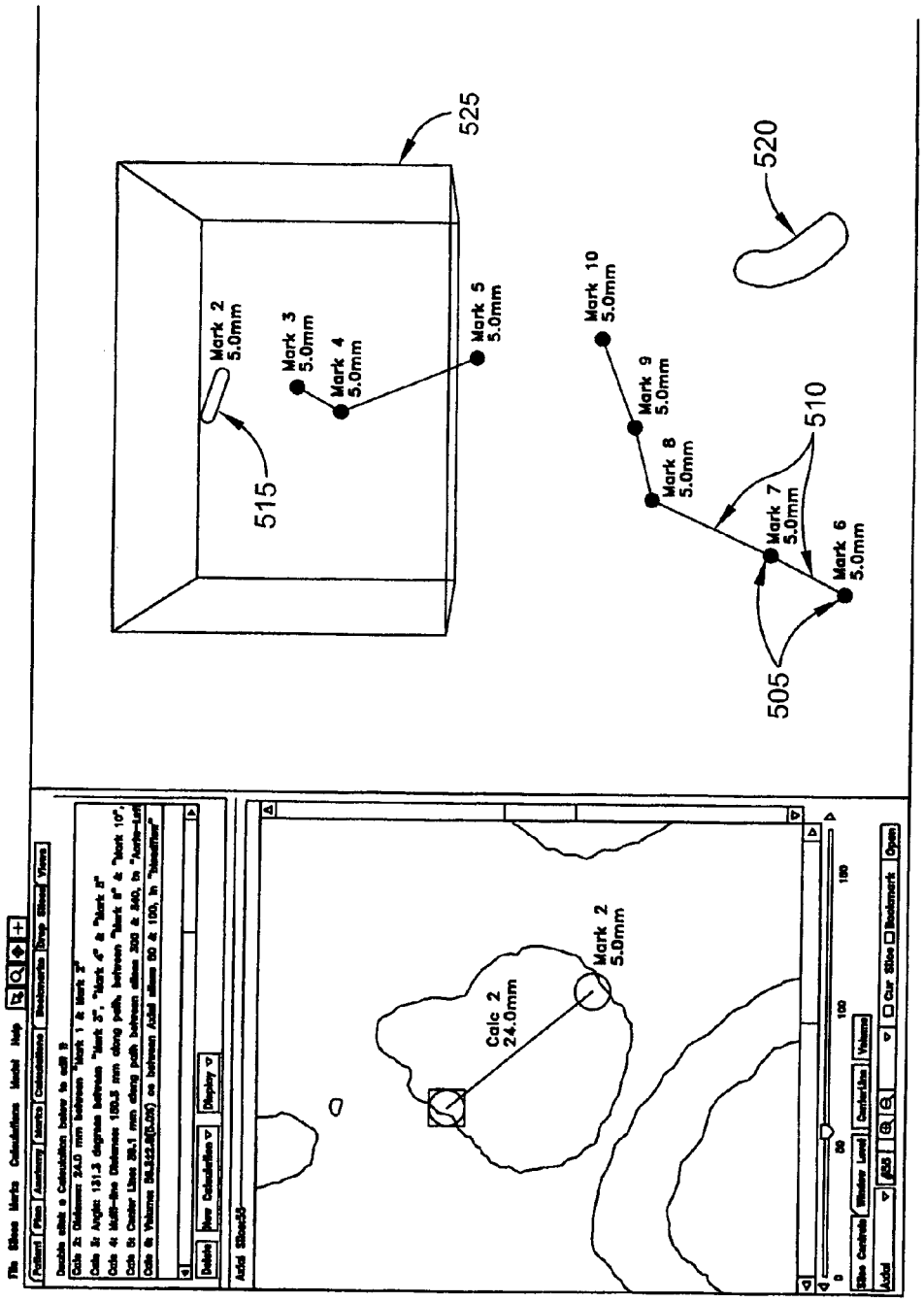
FIG. 32 is a schematic representation of the software object of FIG. 31 in which the aorta has been rendered transparent.

FIG. 32 is similar to FIG. 31, except that aorta 500 has been rendered transparent.

In addition, other geometric elements such as curved lines, intersecting lines, etc. may also be provided for planning and measurement purposes.

Figure 33:
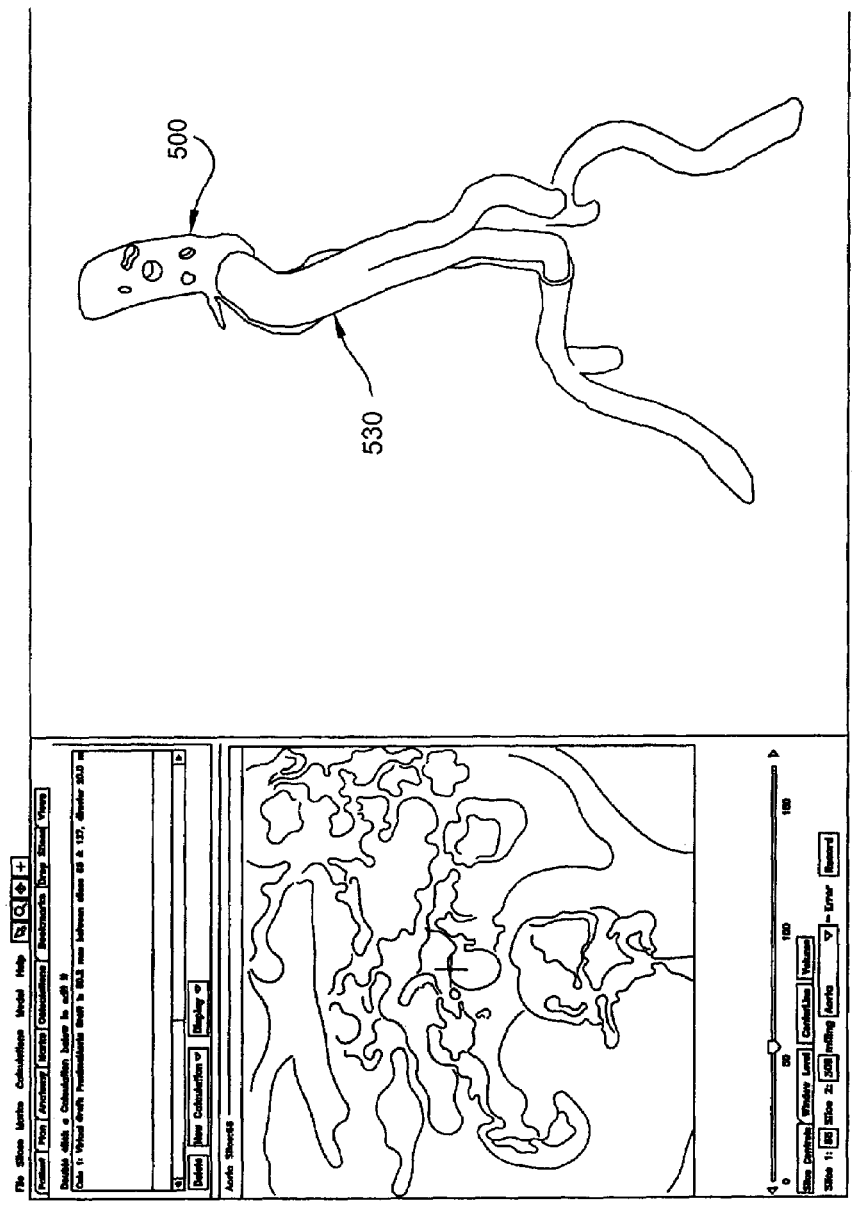
FIG. 33 is a schematic representation of a virtual graft deployed in the aorta of FIG. 31.

Significantly, it is also possible to insert into the system software objects representing virtual grafts, virtual implants, etc. By way of example, in FIG. 33 there is shown a virtual graft 530 which represents an arterial stent which may be deployed in the aorta, e.g., to treat an aortic aneurysm.

Figure 34:
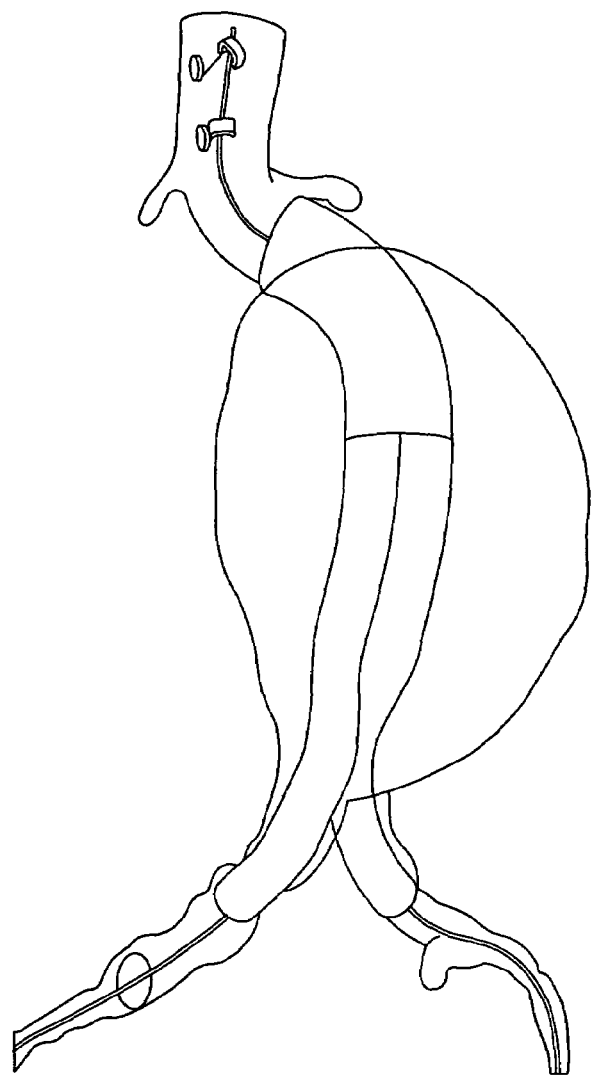
FIG. 34 is a schematic representation of a virtual graft deployed in the aorta.

Virtual Grafts (VG's), Manufacturer Specific Virtual Grafts (MSVG's), Twisteroo™, Native Iliac Rotation (NIR) and TwisterooNIR™ Click-Drag Distance Calculation and Mark Name/Type Dichotomy Virtual Grafts (VG's). Looking next at FIG. 34, in simpler versions of the aforementioned Virtual Graft (VG) for aortic stent applications, users are able to place idealized tubes into the aorta model. The Virtual Graft (VG) helps users visualize what the surgery will look like and stems from the more basic Centerline Calculations discussed above.

In one simple preferred construction, a VG consists of three tubes arranged like a pair of pants. One of these tubes represents the "trunk" of a bifurcated stent graft and the other two tubes represent the legs. Users are able to define the length and diameter of the three tubes but, in this simpler version of the system, must perform calculations on their own to calculate the overlap that is used in placing the parts during surgery. With this form of the invention, it is essential that the doctors be familiar with the dimensions of the product offerings from all Abdominal Aortic Aneurysm (AAA) implant manufacturers, because the doctors must add the lengths of the pieces themselves, account for overlap, etc.

Manufacturer Specific Virtual Graft (MSVG). In a more sophisticated form of the invention, Manufacturer Specific Virtual Graft's (MSVG's) allows users to select and visualize actual stent graft devices within patient-specific 3D anatomy. This MSVG feature simplifies and enhances the vascular surgeon's experience in fitting an endoluminal implant in three principal ways.

(i) Accurate Graft Information. First, the user does not have to remember the graft pieces available from a given manufacturer. With the MSVG graft designer, users simply choose from a list of all available pieces for their chosen manufacturer. For example, rather than having to remember that W. L. Gore Excluders come in a 23 mm by 14 mm by 160 mm size with a product code of "PCT231216", the user will be able to choose this part from a list of all W. L. Gore parts and the software system will both display the correct piece and keep track of the selected part number. This feature prevents users from recording the wrong values and speeds their ability to evaluate how different parts will work in the anatomy. The software system internally keeps a catalog of manufacturer product codes, part geometries and compatibility criteria from component to component.

Figure 36:
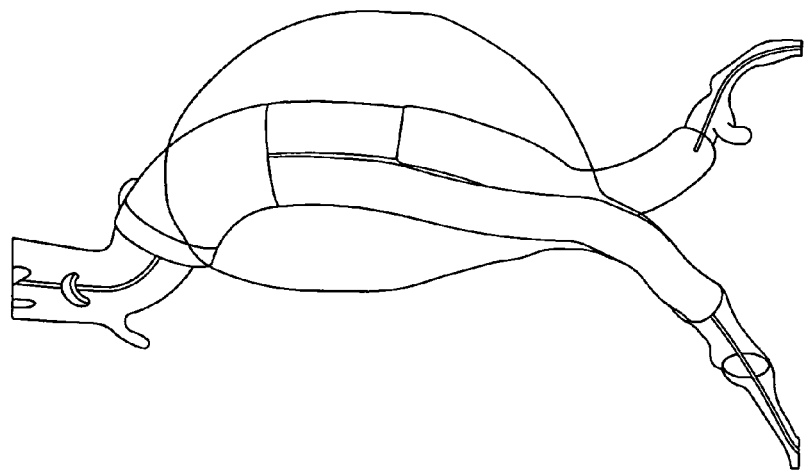
FIG. 36 is a schematic representation of a Manufacturer Specific Virtual Graft (MSVG) after docking of contralateral limb.
Figure 35:
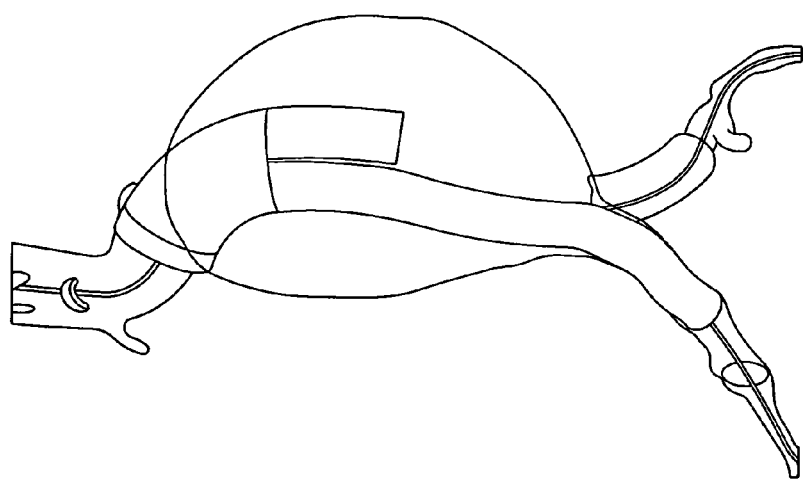
FIG. 35 is a schematic representation of a Manufacturer Specific Virtual Graft (MSVG) before docking of contralateral limb.

(ii) Detailed Graft Visualization. A second, and perhaps most important advance with the MSVG, is the more detailed representation of the grafts. Because endovascular AAA repair is a surgery that generally requires more than one surgical device to be implanted in the anatomy, the MSVG feature is also able to model multiple graft parts at one time, as well as the interaction of their overlap. AAA surgery usually requires, at the minimum, a separate stent graft or "docking limb" to be inserted up the contralateral side of the patient and deployed inside the previously-deployed bifurcated piece. See FIGS. 35 and 36, which show an MSVG before and after docking of a contralateral limb.

For most endovascular surgeries with docking limbs, it is important for the doctor to understand how much the pieces overlap because this distance is important to reduce the risk of slippage and/or endoleak. Each manufacturer will typically specify the amount of overlap that is required to safely deploy a given component pair. The software system is, in one preferred embodiment, able to model up to 9 different graft devices in the same patient, specifically: 1 bifurcated piece, 1 contralateral leg, 6 extenders and 1 aortic extender. To represent this aspect of surgery, the MSVG feature colors the pieces differently based on the amount they overlap each other and their respective sizes. See FIG. 37. The "yellow zone" in the figures represents "over-sizing" which is similar to the physical overlap but is, in some ways, a more accurate way to understand the interaction. More particularly, it can be a more useful indicator because it represents the amount of surface-to-surface contact that the pieces will have when deployed and this over-sizing is often what actually holds the pieces together.

Figure 37:
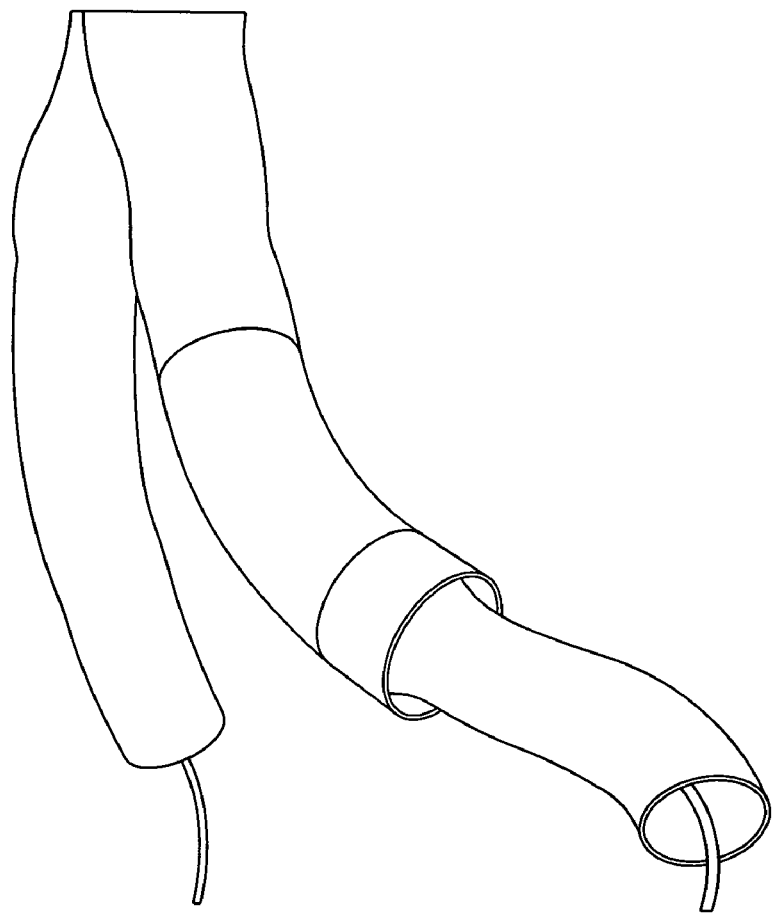
FIG. 37 is a schematic representation of a Manufacturer Specific Virtual Graft (MSVG), with the yellow zone representing "oversizing"

The difference between overlap and "over-sizing" can be been in FIG. 37. Here there is a contralateral leg with a smaller, tapered, extender. Again, the yellow zone represents overlap, but note that the yellow zone does not extend all the way to the bottom of the leg. This is because the extender piece that has been inserted tapers to a diameter smaller than the enclosing piece. When this occurs, the extender piece will not actually press against the inside walls of the enclosing piece and thus will not be over-sized.

There are three additional significant improvements to the graft representations in a preferred MSVG feature. First, the grafts can have variable diameters along their lengths. These increasing or decreasing tapers come directly from the manufacturer specifications and are quite detailed. For example, a bifurcated piece such as the one in FIG. 35 can have a diameter change along the length of its leg, allowing for a "bell-bottomed" or tapered leg. While not all manufacturers' pieces will include such a diameter change, those that do are now modeled more precisely.

The last two visualization features are the inclusion of a representation for graft hooks and the ability to make a graft transparent. Graft hooks, which are typically metal prongs used to secure a graft to the blood vessel, can be displayed using the MSVG simulator as a red circle around the end of the graft. This allows doctors to judge the hook's location relative to the anatomy. Finally, transparent grafts can be used with a visible anatomy to judge the "over-sizing" of a graft relative to both the blood flow anatomy and the thrombus.

(iii) Increased Reliability. The third way that the MSVG enhances the user's experience is through the increased reliability of the system. From beginning to end, the user is aided in choosing the right parts and is less prone to transcription errors from planning to surgery, or problems that can arise due to incompatible parts.

Figure 38:
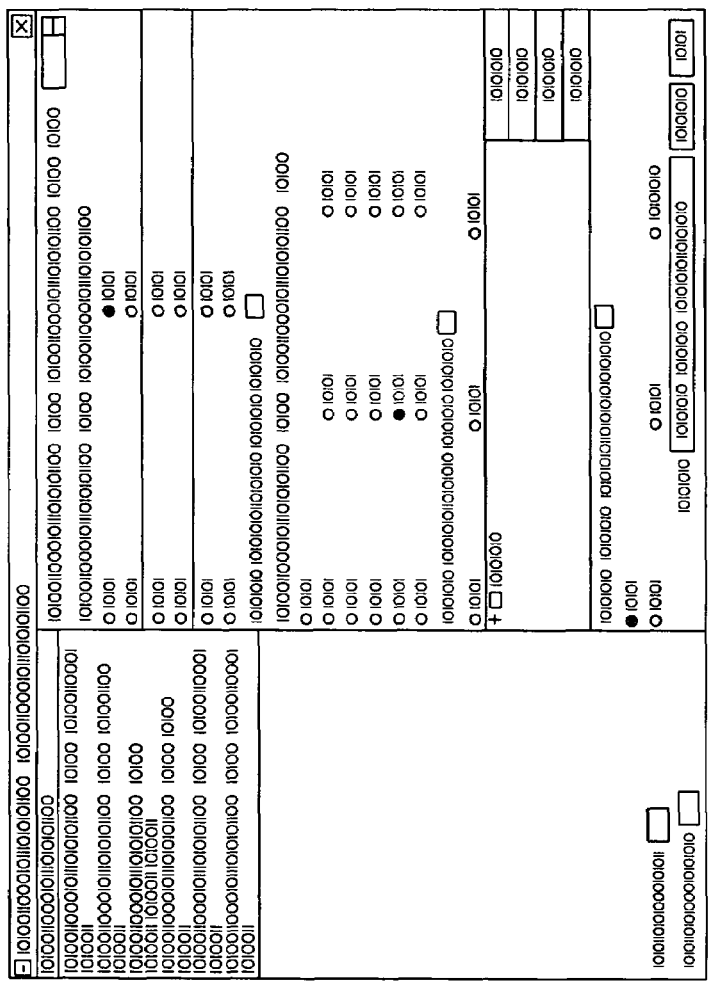
FIG. 38 is a schematic representation of a Manufacturer Specific Virtual Graft (MSVG) Designer.

Increased reliability starts with the new MSVG Designer (see FIG. 38). First of all, the Designer displays all of a user's relevant measurements from their session in the left hand pane. In the right hand pane, there is a list of bifurcated pieces sorted horizontally by length, vertically by iliac diameter and sectioned vertically by aortic diameter. There is also a list of contralateral legs and a tree for iliac extenders. All of the buttons dynamically change their enabled status depending on the user's selections. This interaction implies that checking is performed to make sure that all selected sizes are compatible. The MSVG Designer also checks to make sure that all of the indicated overlaps are within the manufacturer's guidelines for required overlap. The Designer software adds up the length of both the contralateral and ipsilateral sides, subtracting overlaps and displays this number in the two length boxes at the bottom left hand side of the measurement panel. The MSVG also includes a cascading list for selecting the amount of "Twisteroo™" for the graft. This feature is discussed in detail below.

After the user clicks "Build", the program runs final checks to make sure that the selected grafts will display properly in the anatomy. If these pass, it is then on to the visualization module, where the product codes are turned into images and used as texture maps for the 3D creation of the graft. In this way, the vascular surgeon can tell immediately by looking at the Model Window which manufacturer components are being displayed.

In the Product Listing page (see FIG. 39), the user can add any more parts to include in their plan. Different endovascular devices require different sized sheaths for deployment, so users can also include these in the Product Listing dialog. Because all surgeries generally require these sheaths, this page will of course warn users of any attempt to continue without ordering sufficient and correctly sized sheaths.

Figure 40:
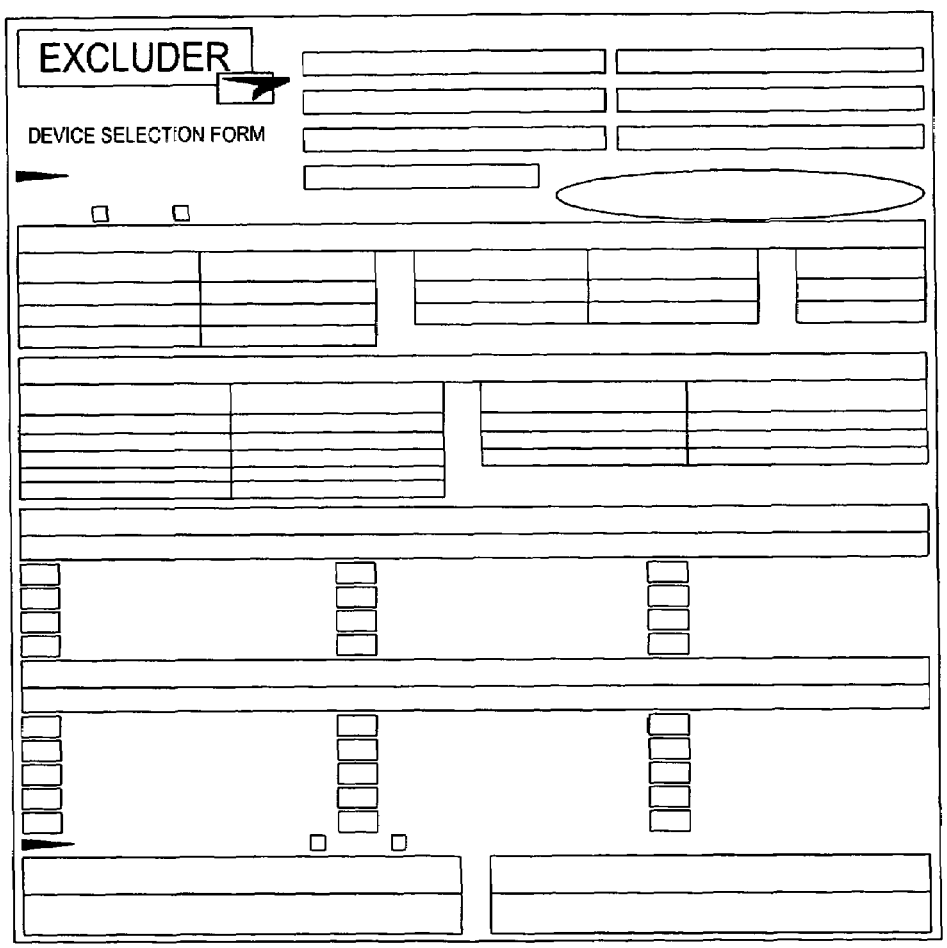
FIG. 40 is a schematic representation of an Order Form PDF.

Finally, the desired graft component quantities are transferred via the Internet to a remote server where they are inserted into an Adobe PDF form (see FIG. 40) which is then kept with the model information on a remote server. This form is accessible over the Internet so that users can print it out and send it in, or use it for later reference.

This order form is the completion of the validated and reliable transfer of information from the graft manufacturers' internal specifications, to the MSVG Designer, to the visualization module and finally to component order fulfillment. This entire process has been designed to prevent the errors caused by either working with incorrect data, not understanding specifications properly and/or mistyping or otherwise confusing catalog items, from start to finish.

Twisteroo™. During endovascular AAA repair, a common surgical technique is to rotate the proximal end of the bifurcated endoprosthesis before it is deployed and then to pass the contralateral leg, either anterior or posterior, to the bifurcated leg before docking it. This technique is popular for many reasons. In some anatomies, it allows for a straighter shot out of the iliacs, making for an easier surgery. Some doctors also feel that it can either improve the device seal or can reduce the pressure from the blood flow on the graft. It can also simply be a useful method of deploying a graft to take up some of the "slack" in the limbs. By forcing a graft into a twisted configuration, it will presumably take a longer path, effectively shortening its run down the iliacs. This can be especially pertinent when occlusion of the internal iliac artery is a concern.

Previously, there has been no way for a surgeon to model this technique in a pre-operative effort to visualize the resultant graft paths or to gauge the effective "shortening" that this technique will have on the overall length of the graft. With the Twisteroo™ feature, users now have a tool to model various degrees of graft twist within a 3D reconstruction of the anatomy.

Figure 42:
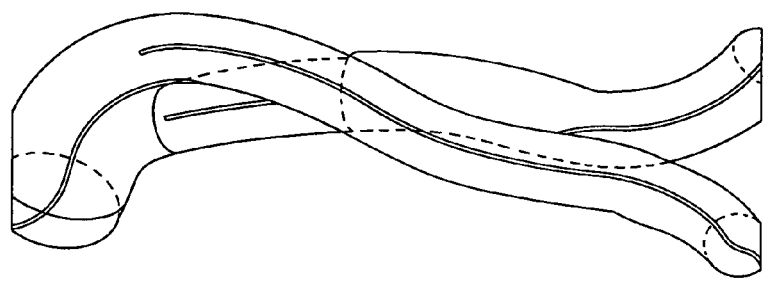
FIG. 42 is a schematic representation of a resultant MSVG.
Figure 41:
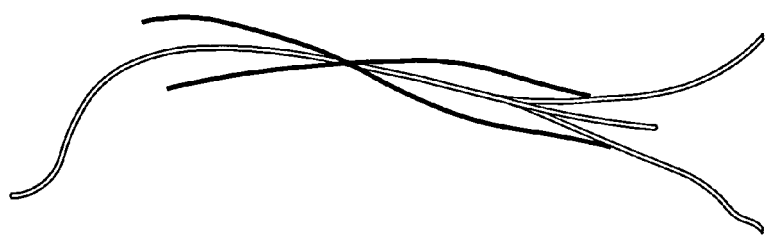
FIG. 41 is a schematic representation of "Twist Lines"

The Twisteroo™ calculation. From a high level view, the basic idea of the twist calculation is to create two new "twist lines", one for each iliac, which begin at the end of the graft trunk and continue until the original centerline splits. At this point, the graft will switch tracks and jump back onto the pre-existing right iliac leg (RIL) and left iliac leg (LIL) centerlines. The existing centerlines are preferably used because they are a reviewed and validated system to predict the general path a graft will take though the anatomy. The twist lines start at the end of the graft trunk because the trunk will simply follow regular centerlines. Once the twist calculation are finished, the grafts begin using the regular RIL and LIL centerlines again, because they will correctly model the behavior of a graft leg through a tortuous anatomy. Thus, the Twisteroo™ is meant to model twisting primarily in the aneurismal sac. FIG. 41 is an example of two twist lines created for a 180-degree twist and FIG. 42 is an example of the Virtual Graft once it has followed the twist.

In this Twisteroo™ product, the iliac branches are assumed to lie in the coronal plane.

The first calculation made in the creation of a twist is to calculate the "spread" variable. This is how far the two legs will be pushed off the centerline as spiraling down. This spread=½ (Left leg diameter/Right leg diameter) which comes from either the MSVG device sizes or a user's generic device parameters. This calculation accounts for potentially different leg diameters for each leg.

The second calculation made is to determine where the twist lines should end. This is calculated for each side, and is termed the "attachment" site. In FIG. 41 above, this is the point on the green line, where the gray line ends. This point is calculated by running down the centerline until the RIL and LIL cubes are separated by a distance greater than the "spread". This is where the graft is stopped from following the twist lines and jumps back onto the regular centerline. It is related to the spread because once the centerlines are that distance apart, the graft limbs are no longer capable of intersecting each other.

Figure 43:
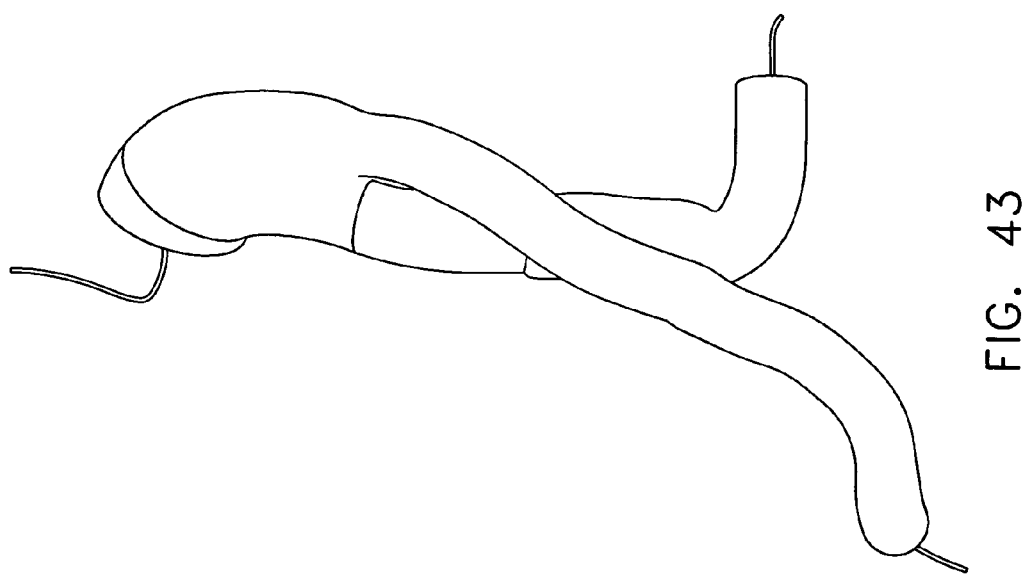
FIG. 43 is a schematic representation of MSVG spline creation.

Spline Creation. Looking next at FIG. 43, splines are a way of connecting points or interpolating between points in a smooth and continuous manner. To do this, a spline takes into account a curve's energy and tries to connect the points in a smooth way. Catmull-Rom spline formulation is preferably used because it interpolates through all of the given control points and is resistant to kinking.

Six control points are used per side to create the spline. With the "septum" defined as the end of the graft trunk, there is one control point set proximal to the septum by 25 mm, one point at the septum, two mid-aneurysm control points each ⅓ of the way from the septum to the sides attachment, and finally one point at the attachment and one 25 mm distal to the attachment. The two points located 25 mm away from the ends of the graft are there to influence the path of the graft above. Their location along the centerline influences the endpoint tangents of the resulting splines so that the curve continues smoothly out of the iliac artery.

The next step is to add the "spread" into the equation in a way that naturally twists the graft down the length of the sac. To do this the most proximal 4 controls points are translated away from the basic centerline. Through basic trigonometry, the degree of twist is plotted on the unit circle and the x and y components of the resulting vector obtained. It is known that at the bottom it is desirable to be directly on the centerline, so the amount of rotation is reduced smoothly as the centerline proceeds distally. Thus, for a 180 degree twist, the first two control points will be translated directly away from their eventual location, while the middle control points will be translated at 120 and then 60 degrees away. All translations are performed in the plane of the centerline cube that they are based on. With these 6 control points, a Catmull-Rom spline is created and the results stored.

Figure 44:
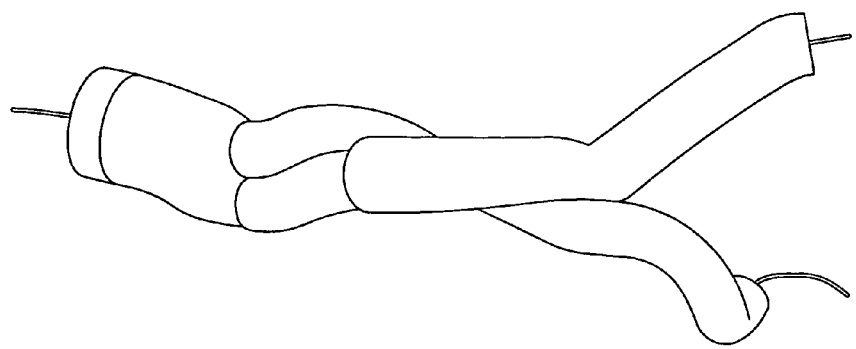
FIG. 44 is a schematic representation of an MSVG contact model.

Contact. Looking next at FIG. 44, the resulting splines can still end up running through each other, because each side has so far been created in isolation. Therefore, the next step is to implement a simple contact model. A preferred contact model is basically a function that increments down each of the twists, finding the nearest neighbor in the other twist line. Once it finds this neighbor, it then calculates the distance between them and then pushes the two points away from each other until they are at least the "spread" value apart. Any contact that is not removed from the legs via this algorithm is modeled later during the visualization process by calculating the distance from leg to leg, and then adjusting the geometry of the graft limbs to "ovalize" them with a minor axis in the direction of the opposite leg.

Filter. Finally, the point locations are convolved through a large triangle filter (30-way) which smoothes out any irregularities left behind by the twisting and contact process described above. This smoothing can result in reducing the distance between the two legs below the "spread" distance, which is actually a desirable effect because it allows the "ovalizing" process above to partially model the graft's actual deformation.

Completion. Finally the files TwistLineRIL.asc and TwistLineLIL.asc are written out in an .asc format. Because the orientation of the resulting cubes is important for texturing and visualization purposes, a function is used to orient the cubes until they both face each other, but also line up smoothly with the corresponding first and last cubes on the original centerlines. Because these are two distinct orientation constraints, a function is used to blend the effect of each method based on where the cube is on the centerline. Preferably a polynomial function is used, such as $y=x^8$, which produces a graph with a characteristically wide base and highly sloped sides. Thus, the first and last cubes are more heavily weighted at the beginning and end of the twist line, but almost all orienting is done towards the neighboring cube through the middle of the twist line.

The MSVG can now be drawn along the twist lines. The most important benefit of this feature is that it can actually model the shortening that a twisted graft's legs will undergo relative to their final location in the iliacs. Previously there was no good way to account for this, and was often simply assumed that it would shorten the graft by several millimeters.

Native Iliac Rotation (NIR) and TwisterooNIR™. In an improved version of the system, the system is capable of recognizing Native Iliac Rotation (NIR) and provides a TwisterooNIR™ product which takes Native Iliac Rotation (NIR) into account when conducting twist calculations.

Native Iliac Rotation (NIR). During the development of the original Twisteroo™, it was noticed that, for some anatomies, the "neutral" amount of twist (or 0 degrees) was actually not the most natural fit for the graft, since the bifurcation of the iliac arteries does not always occur in the coronal plane. Instead, it was found that in some anatomies, the bifurcation of the iliac arteries occurs at an angle from the coronal plane, i.e., the iliac arteries branch off in a twisted fashion, with one iliac more anterior than the other. For the purposes of the present invention, the term Native Iliac Rotation (NIR) can be used to describe the degree of twist of the iliac arteries away from the coronal plane.

Figure 45:
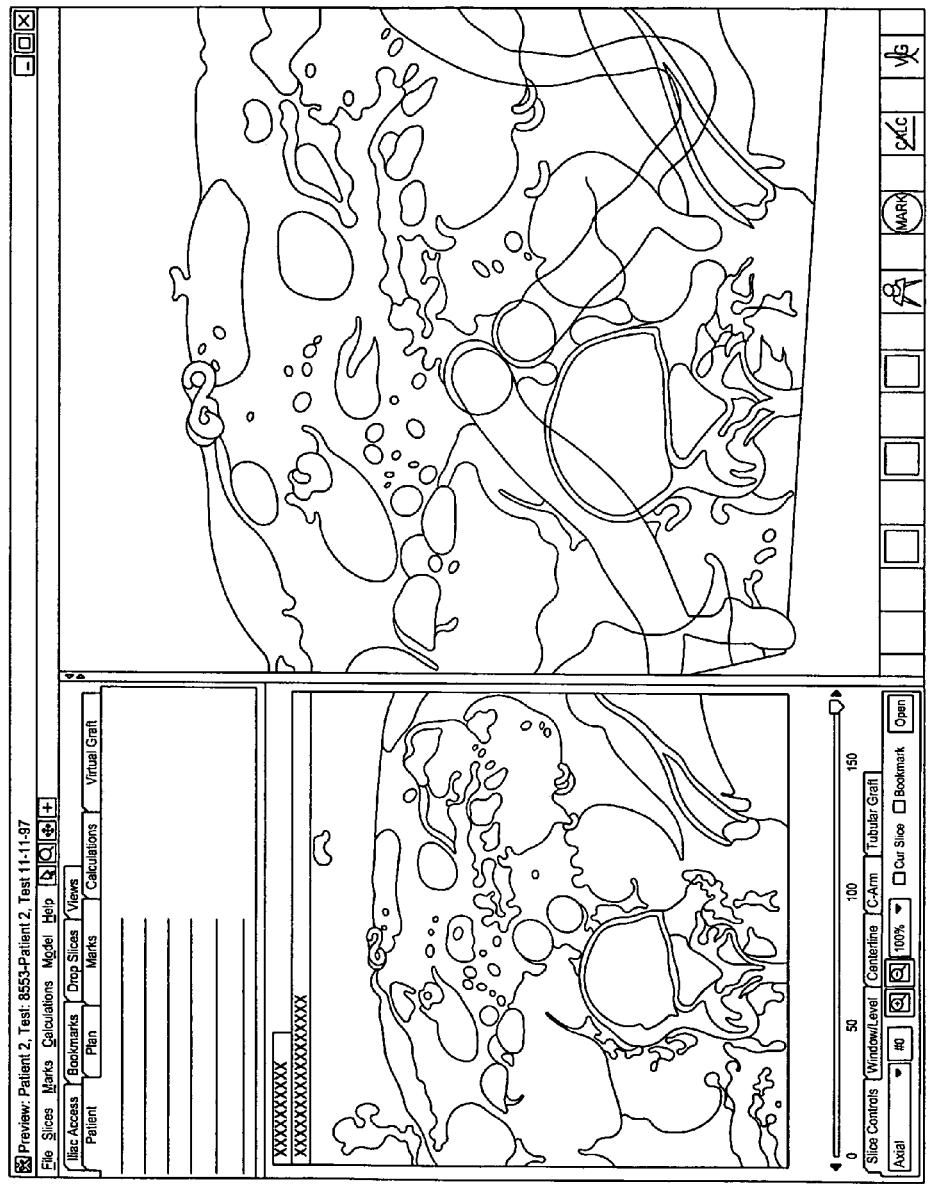
FIG. 45 illustrates a screen display from one preferred construction of the present invention, wherein the display simultaneously provides a 2-D slice window and a 3-D model window, and further wherein the images illustrate Native Iliac Rotation departing from the coronal plane.

Looking now at FIG. 45, there is shown an axial CT scan slice (left side of figure) just below the bifurcation point, and a virtual 3D model (right side of figure) showing the iliac branches extending out of this slice plane. These images show how the two iliac arteries may branch off from one another. More particularly, FIG. 45 shows an example of an anatomy wherein one branch of the iliac artery is significantly more posterior (i.e., closer to the backbone or bottom of the image) than the other branch.

Since the branching of the iliacs does not always happen strictly to the left and right of the anatomy (i.e., with a 0 degree twist off the coronal plane), the aforementioned Twisteroo™ technique for calculating the virtual graft twist does not always result in an accurate assessment of the optimal twist for some patient-specific anatomies.

Accordingly, in one preferred embodiment of the present invention, sometimes hereinafter referred to as the TwisterooNIR™ product, there is provided a new technique for measuring the NIR (i.e., the degree of rotation off the coronal plane) of the iliac arteries, which is then used to increase the accuracy of the aforementioned twist calculation and other tools and measurements.

Calculating Native Iliac Rotation (NIR). This technique begins by simplifying the anatomy into two centerlines, as was previously discussed above. These centerlines are formulated to travel down the center of each vessel as a series of cubes. From this formulation it is easy to determine the XYZ location of any of the cubes in 3-D space.

In order to measure the Native Iliac Rotation (NIR) of a patient-specific anatomy, 3 different centerlines are first produced: (i) a left iliac (LIL) centerline; (ii) a right iliac (RIL) centerline; and (iii) an aorta (AO) centerline (which is coincident with the other two centerlines down through the aneurismal sac until the LIL and RIL centerlines begin to diverge down the left and right sides of the bifurcation, at which point, the AO centerline continues to proceed down the center of the anatomy, directly through the bifurcation and out a short way below the bifurcation.

Next, the XY positions (in the axial plane) of one point from the LIL centerline and one point from the RIL centerline are compared to determine how much the points rotate away from the horizontal. In other words, the two points are compared to see how much each point is rotated away from the coronal plane. It will be appreciated that the compared points from the LIL centerline and the RIL centerline preferably are at the same position in the Z-axis (i.e., along the coronal plane). In one preferred embodiment of the present invention, the left and right iliac centerlines are compared at points approximately one half centimeter below the bifurcation.

Figure 46:
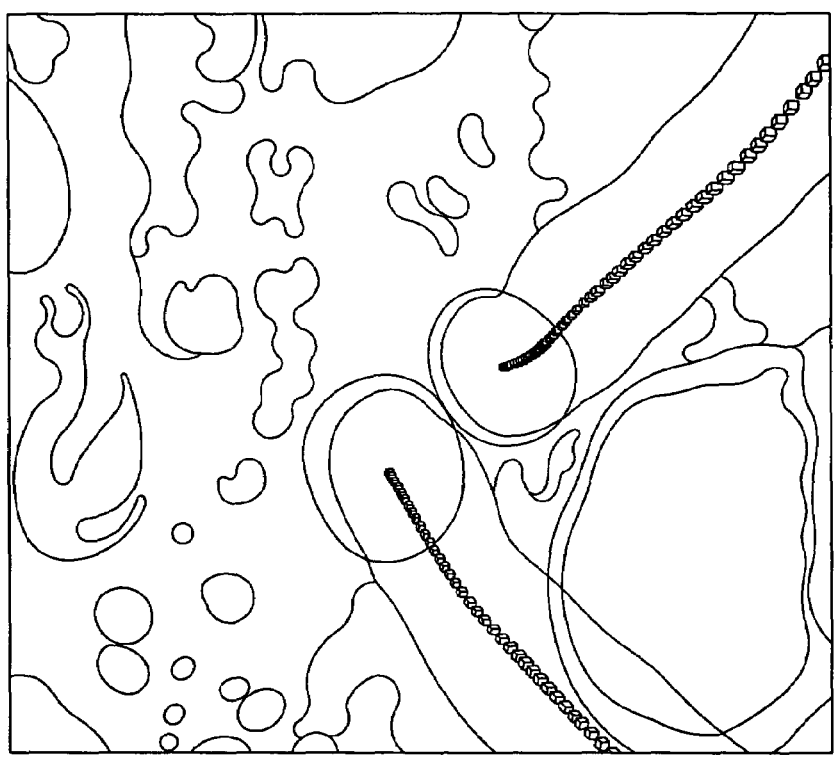
FIG. 46 is a schematic representation of the centerlines for the left iliac (LIL) branch, the right iliac (RIL) branch and the aorta (AO)
Figure 47:
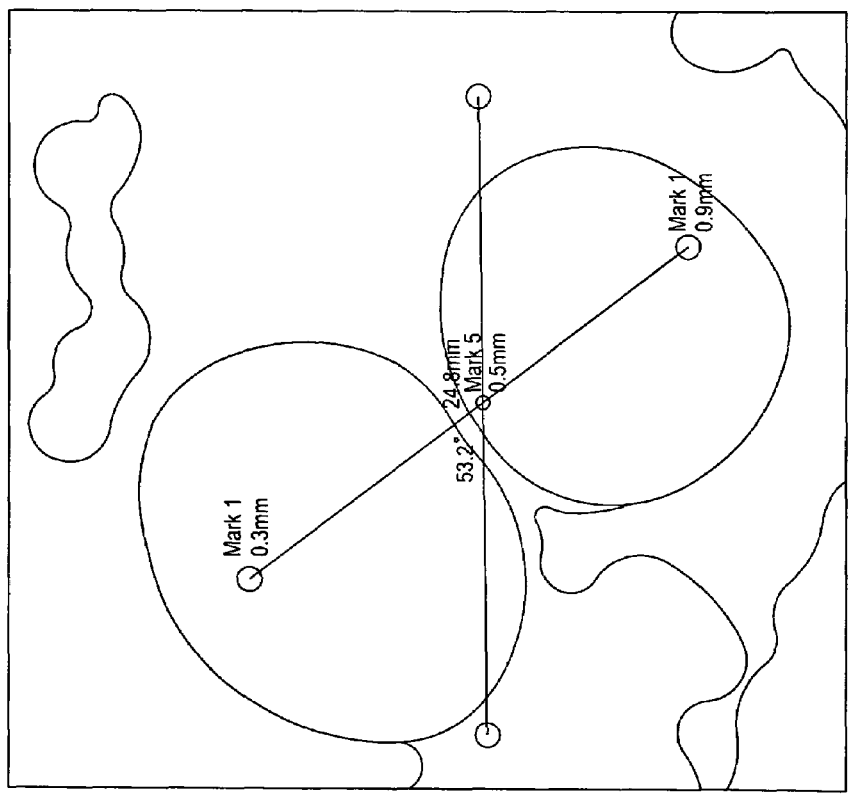
FIG. 47 is a schematic representation showing the calculation of Native Iliac Rotation off the coronal plane.

In another embodiment of the present invention, the length of the centerline is used as a guide to tell a user what part of the LIL and RIL centerlines to compare, since the AO centerline is always of a length defined to just make it past the bifurcation. More particularly, and looking now at FIG. 46, the total number of cubes in the AO centerline is first determined, and then the same number of cubes is used to index into the left and right centerlines. Thus, if there are N cubes in the AO centerline, the $n^{th}$ cube of the LIL centerline (LIL[N]), and the $n^{th}$ cube of the RIL centerline (RIL[N]), are compared. For each of these cubes (i.e., LIL[N] and RIL[N]), the X and Y positions (in 3-D space) are determined. This method is further illustrated in FIG. 47, where a diagonal line has been drawn to extend through a centerline cube from both the left (LIL) and the right (RIL) centerline, and the horizontal line represents the coronal plane. Next, the differences (in X,Y terms) of the two points is calculated, and then the inverse tangent of their quotient is calculated. The angle thus derived from these calculations is the Native Iliac Rotation (NIR) of the two iliacs away from the coronal plane.

TwisterooNIR™. Finding the Native Iliac Rotation (NIR) of a patient-specific anatomy allows the calculation of a more natural twist of the virtual graft for each specific patient. Previously, and as noted above, the Twisteroo™ assumed that the natural state of the rotation was at precisely 0 degrees (i.e., Twisteroo™ assumed that every patient had a "neutral" Native Iliac Rotation). This meant that if the physician wanted to simulate a 180 degree twist, Twisteroo™ would simulate the graft legs twisting from 180 degrees all the way back to 0 degrees. In accordance with the present invention, there is now provided the TwisterooNIR™ product, which uses the previously-calculated Native Iliac Rotation (NIR) when calculating for twist. TwisterooNIR™ simulates the virtual graft legs twisting from the given degree of twist desired back to the patient-specific Natural Iliac Rotation. TwisterooNIR™ provides a more accurate simulation of the natural position at which the virtual graft legs would be as they enter the iliac arteries. In particular, this is an advantageous method of simulating the twist of a graft because, in an anatomy with a high degree of native twist (e.g., a large Natural Iliac Rotation), the graft's twist would end up turning too quickly and in effect overshooting the target, or doing the reverse and not twisting fast enough.

Previously, and as noted above, an algorithm would attempt to rotate the virtual graft from an inputted degree of twist to 0 degrees, by building a spline along two control points spaced between the start and end points. The control points would be set so that ⅓ of the twist would be achieved by the first point, ⅔ of the twist would be achieved by the second point and the rest of the twist would be achieved between the second point and the end point, where the graft centerline rejoins the regular graft centerline. Thus, to achieve a 90 degree twist of the virtual graft, the Twisteroo™ product would space control points at 66 degrees and 33 degrees of twist. As mentioned above, this creates an undesired path in some instances. Specifically, in the case where a patient's iliac limbs are rotated 50 degrees relative to the coronal plane (i.e., the patient has a 50 degree Native Iliac Rotation) and a 90 degree twist of the virtual graft is desired, the final point will be at 50 degrees, and the control points will proceed thus: 90 degrees, 66 degrees, 33 degrees, and 50 degrees, leaving an S-curve.

The TwisterooNIR™ performs its twist calculations by placing two control points in between the beginning and end points just as the Twisteroo™ algorithm did. However, the TwisterooNIR™ calculates the amount to twist desired as:

Total Twist Desired−Native Iliac Rotation=Amount To Twist The Virtual Graft

For the example noted above, the TwisterooNIR™ calculation comes out to 90 degrees−50 degrees=40 degrees. The TwisterooNIR™ then divides the Amount To Twist The Virtual Graft (i.e., 40 degrees) by 3 and performs an interpolation to give control points at: 90 degrees, 76 degrees, 63 degrees, and 50 degrees, leaving a much smoother curve than the S-curve described above.

Figure 48:
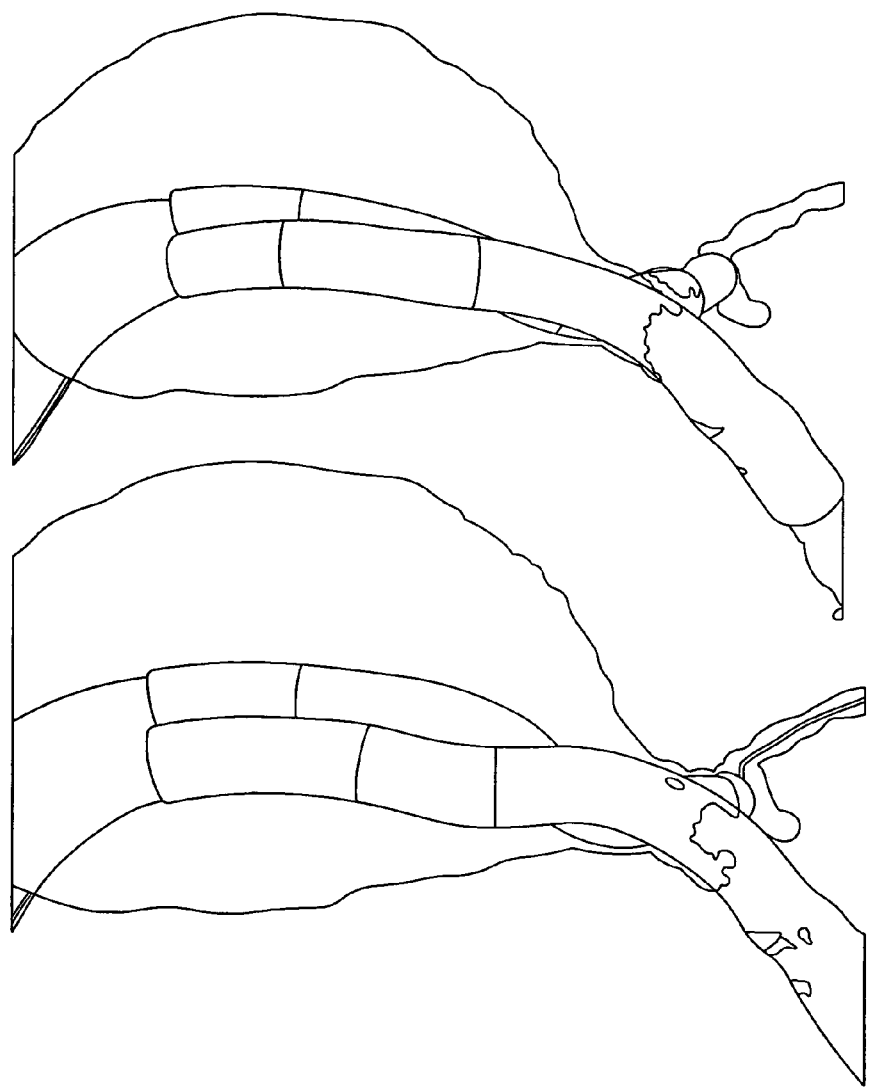
FIG. 48 is a schematic representation comparing the Twisteroo™ and the TwisterooNIR™ products for a patient having a 53 degree Native Iliac Rotation.

Looking now at FIG. 48, another example of the aforementioned problem is illustrated. This example illustrates a problem which may occur even when the graft is set to 0 degrees of twist. The Twisteroo™ product is on the left and the TwisterooNIR™ product is on the right. The degree of twist for both of these grafts is 0 degrees and the Native Iliac Rotation is 53 degrees. In the first case (i.e., the case on the left utilizing the Twisteroo™ product), the control points are at: 0 degrees, 0 degrees, 0 degrees, and 53 degrees. Since the algorithm cannot predict where the final point will be, it cannot approach this point gradually. This produces an unnatural "jerk" at the end of the graft. In the TwisterooNIR™ product, the control points are at: 0 degrees, 17 degrees, 35 degrees, and 53 degrees. These control point calculations produce a smooth and more realistic curve for the graft path.

Figure 49:
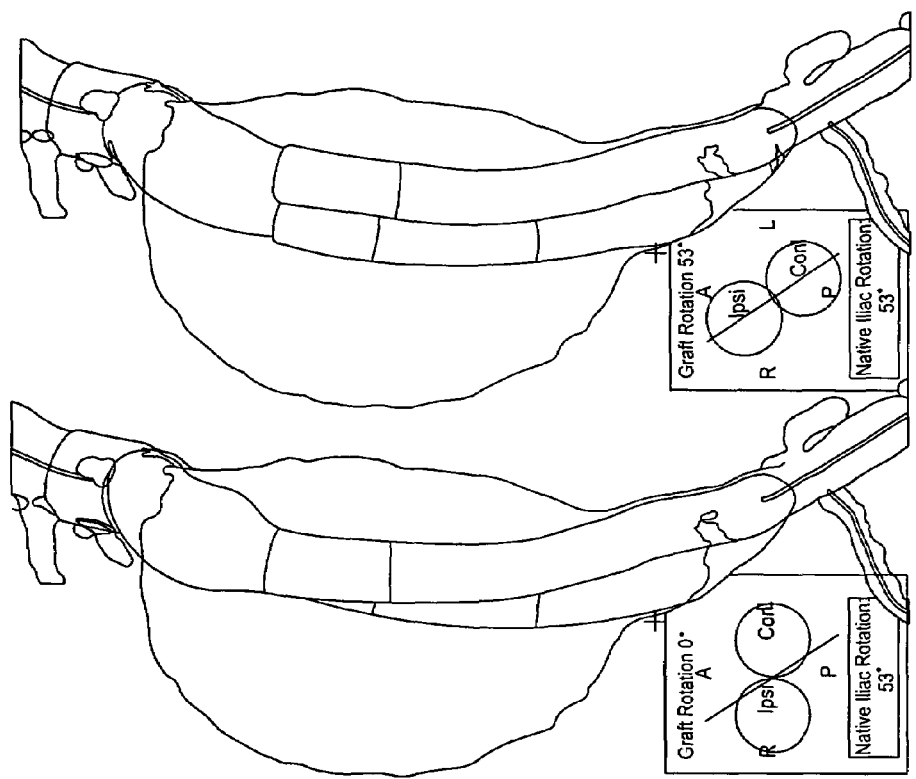
FIG. 49 is another schematic representation comparing the Twisteroo™ and the TwisterooNIR™ products for a patient having a 53 degree Native Iliac Rotation.

Because the grafts will be inserted in a manner that conforms to the twist of the anatomy, the TwisterooNIR™ product reports the Native Iliac Rotation to the user so that they may consider simulating the graft deployment in what has been calculated to be the natural state of the anatomy. Looking now at FIG. 49, this example shows how rotating the graft to the Native Iliac Rotation can produce a subtly different simulation of the way that a surgery may actually proceed. FIG. 49 illustrates how the graft legs are not required to do as much twisting when their rotation is adjusted to the Native Iliac Rotation (see the image on the right) and FIG. 49 further illustrates how these two simulations actually predict that the graft will terminate at a slightly different place in the iliacs due to the difference in the graft path.

"Click-Drag" Distance Calculations. This new feature is a method for creating distance calculations. A distance calculation is defined at the distance across the anatomy from one user-defined "Mark" to another. In simpler versions of the software system, a distance calculation can be defined by selecting 'New Distance Calculation' from a menu. This opens a Dialog through which beginning and ending points can be selected for the calculation from a list of all available Marks. This process has become much easier with the new method. To perform a "Click-Drag" distance calculation, the user simply has to click on the Slice Window, hold down the mouse button, and then drag the mouse to the desired endpoint. The system software will then check to make sure that both Marks of the calculation are within the slice volume and, if so, create two marks with a distance calculation between them. The system software will also automatically change the size of the marks created for the start and end points to be of a small size in order to reduce clutter on the screen. One final feature of the "click-drag" distance calculation is that, if the user drags the mouse back within a minimum distance of the start point, the program will no longer perform a distance calculation if the mouse is released and it will automatically return the size of the mark to normal.

Standard Mark And Calculation Types and the Name/Type Dichotomy. Another preferred new feature of the system is standardized Mark and Calculation types. In simpler versions of the system, Marks and Calculations could have names but these were user-defined and had to be manually typed in for every instance. A simple user-defined name is inherently problematic when trying to compare one user's calculations to someone else's.

This simple naming scheme has been extended by adding a new standard "type" field to all Calculations and Marks. This new "name-type" dichotomy allows users to classify their measurements according to a standardized system while still adding their own names if they would like. This can be particularly useful in the context of the software system where the same measurement can be made in different ways. The "Maximum AAA Diameter" type, for example, could be measured using either a mark diameter or a distance calculation. For this case the user would give all the measurements the same type, but different names.

As far as the interface is concerned, the first step after creating a mark should be to select its type from menu. This menu is a drop-down list with cascading submenus for aortic types, as well as right and left iliac types. Once the user selects a type, the program will automatically create an abbreviated version of name as the measurements name. The user is then free to modify this name if they would like to. The program will not overwrite any name that the user has already chosen. When a calculation is edited and the type changed, the program will only change the name of the measurement if the old name was one of the abbreviated ones created by the program.

A list of all standard mark and calc types can be found in Appendix A attached hereto.

Preview® Product of Medical Metrx Solutions

Numerous of the foregoing features are implemented in the Preview® product offered by Medical Metrx Solutions (formerly Medical Media Systems) of West Lebanon, N.H.

Further Modifications

It is also to be understood that the present invention is by no means limited to the particular construction herein disclosed and/or shown in the drawings, but also comprises any modifications or equivalents within the scope of the claims.

What is claimed is:

1. A method for calculating a Native Iliac Rotation of a patient, the method comprising:
   determining a left iliac centerline;
   determining a right iliac centerline;
   choosing a left iliac point on the left iliac centerline;
   choosing a right iliac point on the right iliac centerline;
   determining the line extending between the left iliac point and the right iliac point;
   calculating the Native Iliac Rotation, wherein the Native Iliac Rotation is expressed as a function of the line position relative to the coronal plane of the patient; and
   displaying the calculated Native Iliac Rotation to a user.

2. A method according to claim 1 wherein the left iliac point and the right iliac point are chosen to be a selected distance below the bifurcation of the aorta into the iliac branches.

3. A method according to claim 1 wherein the left iliac point and the right iliac point are chosen to be a selected distance along the coronal plane.

4. A method according to claim 1 wherein the left iliac point and the right iliac point are chosen to be a selected distance along the centerlines.

5. A method according to claim 1 wherein the method further comprises determining an aorta centerline and further wherein the left iliac point and the right iliac point are determined as a function of the aortic centerline.

6. Apparatus for calculating a Native Iliac Rotation of a patient, the apparatus comprising:
- apparatus for determining a left iliac centerline;
- apparatus for determining a right iliac centerline;
- apparatus for choosing a left iliac point on the left iliac centerline;
- apparatus for choosing a right iliac point on the right iliac centerline;
- apparatus for determining the line extending between the left iliac point and the right iliac point;
- apparatus for calculating the Native Iliac Rotation, wherein the Native Iliac Rotation is expressed as a function of the line position relative to the coronal plane of the patient; and
- apparatus for displaying the calculated Native Iliac Rotation to a user.

* * * * *